(12) United States Patent
Shankman

(10) Patent No.: US 8,865,113 B2
(45) Date of Patent: Oct. 21, 2014

(54) FACILE SYNTHESIS OF GRAPHENE, GRAPHENE DERIVATIVES AND ABRASIVE NANOPARTICLES AND THEIR VARIOUS USES, INCLUDING AS TRIBOLOGICALLY-BENEFICIAL LUBRICANT ADDITIVES

(75) Inventor: Richard S. Shankman, Boca Raton, FL (US)

(73) Assignee: Peerless Worldwide, LLC, Boca Raton, FL (US)

( * ) Notice: Subject to any disclaimer, the term of this patent is extended or adjusted under 35 U.S.C. 154(b) by 67 days.

(21) Appl. No.: 13/583,507

(22) PCT Filed: Mar. 15, 2012

(86) PCT No.: PCT/US2012/029276
§ 371 (c)(1),
(2), (4) Date: Sep. 7, 2012

(87) PCT Pub. No.: WO2012/125854
PCT Pub. Date: Sep. 20, 2012

(65) Prior Publication Data
US 2014/0134092 A1 May 15, 2014

Related U.S. Application Data

(60) Provisional application No. 61/596,936, filed on Feb. 9, 2012, provisional application No. 61/579,993, filed (Continued)

(51) Int. Cl.
*C09C 1/56* (2006.01)
*C01B 31/04* (2006.01)
*B82Y 40/00* (2011.01)

(52) U.S. Cl.
CPC ............ *C01B 31/0438* (2013.01); *B82Y 40/00* (2013.01); *C01B 31/0453* (2013.01); *Y10S 977/755* (2013.01)

USPC ................... 423/460; 423/445 B; 252/378 R; 977/755

(58) Field of Classification Search
CPC ............ C01B 31/0438; C01B 31/0446; C01B 31/0453; C01B 31/0423; B82B 1/00; B82B 3/00; B82Y 99/00; C10M 125/02; C10M 113/00; C10M 13/02; C10M 125/00
USPC ................... 423/415.1, 460, 445 B; 977/755; 252/378 R See application file for complete search history.

(56) References Cited

U.S. PATENT DOCUMENTS 7,071,258 B1 7/2006 Jang et al.
7,186,474 B2 3/2007 Jang (Continued)

OTHER PUBLICATIONS

Pinault, M., et al. "Carbon nanotubes produced by aerosol pyrolysis: growth mechanisms and post-annealing effects." Diamond and related materials 13.4 (2004): 1266-1269.*

(Continued)

*Primary Examiner* — Richard M Rump
(74) *Attorney, Agent, or Firm* — Finnegan, Henderson, Farabow, Garrrett & Dunner LLP; Ernest F. Chapman, Esq.; Nancy J. Flint, Esq.

(57) ABSTRACT

Methods of ex situ synthesis of graphene, graphene oxide, reduced graphene oxide, other graphene derivative structures and nanoparticles useful as polishing agents are disclosed. Compositions and methods for polishing, hardening, protecting, adding longevity to, and lubricating moving and stationary parts in devices and systems, including, but not limited to, engines, turbos, turbines, tracks, races, wheels, bearings, gear systems, armor, heat shields, and other physical and mechanical systems employing machined interacting hard surfaces through the use of nano-polishing agents formed in situ from lubricating compositions and, in some cases, ex situ and their various uses are also disclosed.

20 Claims, 36 Drawing Sheets

Related U.S. Application Data on Dec. 23, 2011, provisional application No. 61/568,957, filed on Dec. 9, 2011, provisional application No. 61/546,368, filed on Oct. 12, 2011, provisional application No. 61/541,637, filed on Sep. 30, 2011, provisional application No. 61/538,528, filed on Sep. 23, 2011, provisional application No. 61/503,203, filed on Jun. 30, 2011, provisional application No. 61/491,633, filed on May 31, 2011, provisional application No. 61/452,781, filed on Mar. 15, 2011.

(56) References Cited

U.S. PATENT DOCUMENTS

| | | | |
|---|---|---|---|
| 7,566,410 | B2 | 7/2009 | Song et al. |
| 7,623,340 | B1 | 11/2009 | Song et al. |
| 7,662,321 | B2 | 2/2010 | Guo et al. |
| 7,745,047 | B2 | 6/2010 | Zhamu et al. |
| 7,758,783 | B2 | 7/2010 | Shi et al. |
| 7,785,492 | B1 | 8/2010 | Jang et al. |
| 7,790,285 | B2 | 9/2010 | Zhamu et al. |
| 7,824,651 | B2 | 11/2010 | Zhamu et al. |
| 7,842,271 | B2 | 11/2010 | Petrik |
| 7,875,219 | B2 | 1/2011 | Zhamu et al. |
| 7,887,927 | B2 | 2/2011 | Jang et al. |
| 7,892,514 | B2 | 2/2011 | Jang et al. |
| 7,948,739 | B2 | 5/2011 | Zhamu et al. |
| 7,993,780 | B2 | 8/2011 | Jang et al. |
| 7,999,027 | B2 | 8/2011 | Zhamu et al. |
| 8,114,373 | B2 | 2/2012 | Jang et al. |
| 8,114,375 | B2 | 2/2012 | Jang et al. |
| 8,119,288 | B2 | 2/2012 | Zhamu et al. |
| 8,132,746 | B2 | 3/2012 | Zhamu et al. |
| 8,216,541 | B2 | 7/2012 | Jang et al. |
| 8,222,190 | B2 | 7/2012 | Zhamu et al. |
| 8,226,801 | B2 | 7/2012 | Zhamu et al. |
| 2007/0292698 | A1 | 12/2007 | Gause |
| 2011/0201739 | A1 | 8/2011 | Beall |

OTHER PUBLICATIONS

Wiersum, U. et al., "The Formation of Polyaromatic Hydrocarbons, Fullerenes and Soot in Combustion: Pyrolytic Mechanisms and the Industrial and Environmental Connection", pp.

Nakka, R., Amateur Experimental Rocketry, vol. 7, self-published on CD, available at http://www.nakka-rocketry.net/cdrom.html, Jan. 2011.

Ravindra et. al., "Atmospheric polycyclic aromatic hydrocarbons: Source attribution, emission factors and regulation", Atmospheric Environment, vol. 42, pp. 2895-2921, 2008.

Brinley, B.R., Rocket Manual for Amateurs, Ballantine Books, New York, New York, 1960.

Sakakura et al., "Transformation of Carbon Dioxide", Chem. Rev., vol. 107, pp. 2365-2387, 2007.

Shafir et al., Kinetics and Products of the Self-Reaction of Propargyl Radicals, J. Phys. Chem. A, vol. 107, pp. 8893-8903, 2003.

Shukla et al., "Role of Methyl Radicals in the Growth of PAHs", J. Am. Soc. Mass Spectrom., vol. 21, pp. 534-544, 2010.

Si et al., "Synthesis of Water Soluble Graphene", Nano Lett., vol. 9, pp. 1679-1682, 2008.

Wang et al., "Facile Synthesis and Characterization of Graphene Nanosheets", J. Phys. Chem. C, vol. 112, pp. 8192-8195, 2008.

Su et al., "New insight into the soot nanoparticles in a candle flame", Chem. Commun., vol. 47, pp. 4700-4702, 2011.

Sun et al., "ZrOCl2•8H2O: An Efficient, Cheap and Reusable Catalyst for the Esterification of Acrylic Acid and Other Carboxylic Acids with Equimolar Amounts of Alcohols", Molecules, vol. 11, pp. 263-271, 2006.

Tang et al., "An Optimized Semidetailed Submechanism of Benzene formation from Propargyl Recombination", J. Phys. Chem. A, vol. 110, pp. 2165-2175, 2006.

Tian et al., "Nanosized Carbon Particles From Natural Gas Soot", Chem. Mater., vol. 21, pp. 2803-2809, 2009.

Tiefenauer et al., "In vivo evaluation of magnetite nanoparticles for use as a tumor contrast agent in MRI", Magnetic Resonance Imaging, vol. 14, No. 4, pp. 391-402, 1996.

Tomlinson et al., "Adsorption Properties of Succinimide Dispersants on Carbonaceous Substrates", Carbon, vol. 38, pp. 13-28, 2000.

Udeye et al., "Ethanol heterogeneous azeotropic distillation design and construction", Internat. J. of Phys. Sci., vol. 4, pp. 101-106, 2009.

Vander Wal et al., "Flame Synthesis of Carbon Nanotubes using Catalyst Particles Prepared by Laser Ablation", Am. Chem. Soc., Div. Fuel Chem., vol. 49, pp. 879-880, 2004.

Wang, "Synthetic and Characterization of Ethylene Carbonate Modified Polyisobutylene Succinimide Dispersants", University of Waterloo Masters Thesis, 2010.

Wellmann et al., "Growth of graphene layers on HOPG via exposure to methyl radicals", Surface Science, vol. 542, pp. 81-93, 2003.

Won et al., "Effect of Temperature on Carbon-Black Agglomeration in Hydrocarbon Liquid with Adsorbed Dispersant", Langmuir, vol. 21, pp. 924-932, 2005.

Wu et al., "Synthesis of high-quality graphene with a pre-determined number of layers", Carbon, vol. 47, pp. 493-499, 2009.

Ye et al., "Synthesis of Sugar-Containing Amphiphiles for Liquid and Supercritical Carbon Dioxide", Ind. Eng. Chem. Res., vol. 39, pp. 4564-4566, 2000.

Yoon et al., "Synergistic effect of mixing dimethyl ether with methane, ethane, propane, and ethylene fuels on polycyclic aromatic hydrocarbon and soot formation", Combustion and Flame, vol. 154, pp. 368-377, 2008.

Yoon et al., "Targeted medication delivery using magnetic nanostructures", J. Phys.: Condens. Matter, vol. 19, 9 pages, 2007.

Yu et al., "Is There a Stable Bucky-diamond Structure for SiC Cluster", submitted to the Journal of Chemical Physics on Aug. 24, 2011.

Yu et al., "Copper- and copper-N-heterocyclic carbene-catalyzed C—H activating carboxylation of terminal alkynes with CO2 at ambient conditions", PNAS, vol. 107, pp. 20184-20189, 2010.

Zhang et al., "Synthesis and interfacial properties of sophorolipid derivatives", Colloids and Surfaces A: Physicochem. Eng. Aspects, vol. 240, pp. 75-82, 2004.

Zhou et al., "Controlled Synthesis of Large-Area and Patterned Electrochemically Reduced Graphene Oxide Films", Chem.-Eur. J., vol. 15, pp. 6116-6120, 2009.

Zhu et al., "Graphene and Graphene Oxide: Synthesis, Properties, and Applications", Adv. Mater., vol. 22, pp. 3906-3924, 2010.

Zhu et al., "Transparent self-assembled films of reduced graphene oxide platelets", Appl. Phys. Lett., vol. 95, pp. 103,104-1-103,104-3, 2009.

Blanchet, T.A., L Lauer, Y.-F. Liew, S.J. Rhee and W.G. Sawyer, Solid lubrication by decomposition of carbon monoxide and other gases, Surface and Coatings Technology, 68/69 (1994) 446-452.

Semrau, "Practical process design of particulate scrubbers", Chem. Eng., vol. 84, pp. 87-91, 1977.

Lunge, D., Coal-Tar and Ammonia, 5th ed., Part I, D. Van Nostrand Co., New York, 1916, p. 374.

Osawa, E., "Single-Nano Buckydiamond Particles, Synthesis Strategies, Characterization Methodologies and Emerging Applications", Ch. 1, Nanodiamonds: Applications in Biology and Nanoscale Medicine, Ho, D. (ed.), Springer Science + Business Media, LLC, New York, 2010.

Dekkers, Rob, Chapter 5: "Deoxidation in Low Carbon Steel Killed with Aluminum", Ph.D. Thesis, Katholieke Universiteit Leuven, Leuven, pp. 43-65, Belgium, 2002).

Alavi et al., "Alkaline-Earth Metal Carbonate, Hydroxide and Oxide Nano-Crystals Synthesis Methods, Size and Morphologies Consideration", Nanocrystal, Dr. Yoshitake Masuda (Ed.), ISBN: 978-953-307-199-2, Intech, available from http://www.intechopen.com/books/nanocrystal/alkaline-earth-metal-carbonate-hydroxide-and-oxide-nano-crystals-synthesis-methods-size-and-morpholo as of Jan. 21, 2013.

Andreozzi et al., "Iron(III) (hydr)oxide-mediated photooxidation of 2-aminophenol in aqueous solution: a kinetic study", Water Research, vol. 37, pp. 3682-3688, 2003.

(56) References Cited

OTHER PUBLICATIONS

Baby et al., "Enhanced Convective Heat Transfer Using Graphene Dispersed Nanofluids", Nanoscale Research Letters, vol. 6, No. 289, 2011.

Barar et al., "Freidel-Crafts Cross-Linking for Polystyrene Modification", Ind. Eng. Chem. Prod. Res. Dev., vol. 22, pp. 161-166, 1983).

Barnard et al., "Substitutional Nitrogen in Nanodiamond and Bucky-Diamond Particles", J. Phys. Chem. B, vol. 109, pp. 17107-17112, 2005.

Barnard et al., "Coexistence of Bucky-diamond with nanodiamond and fullerene carbon phases", Physical Review B, vol. 68, 073406, 2003.

Blodgett, "Films built by depositing successive monomolecular layers on a solid surface", J. Amer. Chem. Soc., vol. 57, pp. 1007-1022, 1935.

Bohme, "PAH and Fullerene Ions and Ion/Molecule Reactions in Interstellar and Circumstellar Chemistry", Chem. Rev., vol. 92, pp. 1487-1508, 1992.

Botta et al., "Mechanochemical synthesis of hercynite", Materials Chemistry and Physics, vol. 76, pp. 104-109 (2002).

Brodie, "On the Atomic Weight of Graphite", Proc. of the Royal Soc. of London, vol. 10, p. 249, 1859.

California Code of Regulations, Title 13, Div. 3, Chapter 14. Verification Procedure, Warranty and In-Use Compliance Requirements for In-Use Strategies to Control Emissions from Diesel Engines.

Cao et al., "Synthesis and characterization of graphene encapsulated iron nanoparticles", Nanoscience, vol. 12, No. 1, pp. 35-39, 2007.

Chen et al., "Synthesis of hercynite by reaction sintering", Journal of the European Ceramic Society, vol. 31, pp. 259-263, 2011.

Christova et al., "Rhamnolipid Biosurfactants Produced by *Renibacterium salmoninarum* 27BN During Growth on n-Hexadecane", Zeitschrift fur Naturforschung Teil C Biochemie Biophysik Biologie Virologie, vol. 59, pp. 70-74, 2004.

Chuvilin et al., "Direct transformation of graphene to fullerene", Nature Chemistry, vol. 2, pp. 450-453, 2010.

Dato et al., "Substrate-Free Gas-Phase Synthesis of Graphene Sheets", Nano Lett., vol. 8, pp. 2012-2016, 2008.

Dreyer et al., "The chemistry of graphene oxide", Chem. Soc. Rev., vol. 39, pp. 228-240, 2010.

Fan et al., "Deoxygenation of Exfoliated Graphite Oxide under Alkaline Conditions: A Green Route to Graphene Preparation", Adv. Mater., vol. 20, pp. 4490-4493, 2008.

Fenimore, "Interfacial Self-assembly of Sugar-based Amphiphiles: Solid- and Liquid-core Capsules", University of Cincinnati Ph.D. thesis dated Oct. 16, 2009.

Frenklach et al., "Aromatics Growth beyond the First Ring and the Nucleation of Soot Particles", Preprints of the 202nd ACS National Meeting, vol. 36, pp. 1509-1516, 1991.

Gao et al., "Hydrazine and Thermal Reduction of Graphene Oxide: Reaction Mechanisms", J. Phys. Chem. C, vol. 114, pp. 832-842, 2010.

Gautam et al., "Effect of Diesel Soot Contaminated Oil on Engine Wear—Investigation of Novel Oil Formulations", Tribology International, vol. 32, pp. 687-699, 1999.

Gazi et al., "A Modelling Study of Allene and Propyne Combustion in Flames", Proceedings of the European Combustion Meeting, 2011.

Geim, et al., "The Rise of Graphene", Nat. Mater., vol. 6, pp. 183-191, 2007.

Germaneau, "Amphiphilic Sugar Metal Carbenes: From Fischer Type to N-Heterocyclic Carbenes (NHCs)", Ph.D. Dissertation, UniversitéPierre et Marie Curie—Paris 6, Place Jussieu, 75005 Paris, France; Kekulé-Institut für Organische Chemie und Biochemie, Rheinischen Friedrich-Wilhelms-Universität Bonn, 4 Gerhard-Domagk-Strasse 1, 53121 Bonn, Deutschland (Sep. 10, 2007).

Hiteshkumar et al., "Self-assembly in sugar-oil complex glasses", Nature Materials, 6, pp. 287-290, 2007.

Bracmort, "Biochar: Examination of an Emerging Concept to Sequester Carbon", Encyclopedia of Earth, National Council for Science and the Environment, Washington, D.C., 2011.

Hummers et al., "Preparation of Graphitic Oxide", J. Am. Chem. Soc., vol. 80, p. 1339, 1958.

Marcano et al., "Improved Synthesis of Graphene Oxide", ASC Nano, vol. 4, pp. 4806-4814, 2010.

Jadhav et al., "Sugar-Derived Phase-Selective Molecular Gelators as Model Solidifiers for Oil Spills", Angew. Chem. Int. Ed., vol. 49, pp. 7695-7698, 2010.

Jao et al., "Soot Characterisation and Diesel Engine Wear", Lubrication Science, vol. 16, pp. 111-126, 2004.

Jiang et al., "Turning carbon dioxide into fuel", Phil. Trans. R. Soc. A, vol. 368, pp. 3343-3364, 2010.

Jung et al., "Self-Assembling Structures of Long-Chain Sugar-Based Amphiphiles Influenced by the Introduction of Double Bonds", Chem. Eur. J., vol. 11, pp. 5538-5544, 2005.

Katritzky et al., "Aqueous High-Temperature Chemistry of Carbo- and Heterocycles. 20. Reactions of some Benzenoid Hydrocarbons and Oxygen-Containing Derivatives in Supercritical Water at 460° C.", Energy & Fuels, vol. 8, pp. 487-497, 1994.

Kim et al., "Magnetic properties of the spinel phase for $FexCu1-xRh2Se4$", J. Appl. Phys., vol. 64, 342190, 1988.

Liu et al., "Super polishing of stainless steel mould insert for high quality optical lens fabrication", SIMTech Technical Reports, vol. 8, No. 3, pp. 142-148, Jul.-Sep. 2007.

Mansurov, "Formation of Soot from Polycyclic Aromatic Hydrocarbons as well as Fullerenes and Carbon Nanotubes in the Combustion of Hydrocarbon", Journal of Engineering Physics and Thermodynamics, vol. 84, pp. 125-159, 2011.

Mcallister et al., "Single Sheet Functionalized Graphene by Oxidation and Thermal Expansion of Graphite", Chem. Mater., vol. 19, pp. 4396-4404, 2007.

McEnally et al., "Computational and Experimental Study of Soot Formation in a Coflow, Laminar Ethylene Diffusion Flame", 27th Symposium (International) on Combustion, pp. 1497-1505, 1998.

Meima et al., "Catalyst deactivation phenomena in styrene production", Applied Catalysis A: General, vol. 212, pp. 239-245, 2001.

Mkhoyal et al., "Atomic and Electronic Structure of Graphene-Oxide", Nano Lett., vol. 9, pp. 1058-1063, 2009.

Mochalin et al., "The properties and applications of nanodiamonds", Nature Nanotechnology, vol. 7, pp. 11-23, 2012.

Palacios et al., "Effect of superplasticizer and shrinkage-reducing admixtures on alkali-activated slag pastes and mortars", Cement and Concrete Research, vol. 35, pp. 1358-1367, 2004.

Paleta et al., "Novel amphiphilic fluoroalkylated derivatives of xylitol, D-glucose and D-galactose for medical applications: hemocompatibility and co-emulsifying properties", Carbohydrate Research, vol. 337, pp. 2411-2418, 2002.

Pan et al., "Synthesis and growth mechanism of carbon nanotubes and nanofibers from ethanol flames", Micron, vol. 35, pp. 461-468, 2004.

Pinault et al., "Carbon nanotubes produced by aerosol pyrolysis: growth mechanisms and post-annealing effects", Diamond and Related Materials, vol. 13, pp. 1266-1269, 2004.

Pope et al., "Exploring Old and New Benzene Formation Pathways in Low-Pressure Premixed Flames of Aliphatic Fuels", Proceedings of the Combustion Institute, vol. 28, pp. 1519-1527, 2000.

Pulgarin et al., "Iron Oxide-Mediated Degradation, Photodegradation, and Biodegradation of Aminophenols", Langmuir, vol. 11, pp. 519-526, 1995.

Putz et al., "Evolution of Order During Vacuum-Assisted Self-Assembly of Graphene Oxide Paper and Associated Polymer Nanocomposites", ASC Nano, vol. 5, pp. 6601-6609, 2001.

Aitcin et al., "Superplasticizers: How they Work and Why the Occasionally Don't", Concrete International, vol. 16, pp. 45-52, 1994.

Belleville et al., "Crystallization of ferric hydroxide into spinel by adsorption on colloidal magnetite", Journal of Colloid and Interface Science, vol. 150, pp. 453-460, 1992.

Boehm et al., "Das Adsorptionsverhalten sehr dünner Kohlenstoff-Folien", Z. Anorg. Allg. Chem., vol. 316, pp. 119-127, 1962, English translation of Abstract.

(56) References Cited

OTHER PUBLICATIONS

Coppalle et al., "Experimental and Theoretical Studies on Soot Formation in an Ethylene Jet Flame", Combust. Sci. and Techn., vol. 93, pp. 375-386, 1993.

Ryason et al., "Polishing Wear by Soot", Wear, vol. 137, pp. 15-24, 1990.

Soroushian et al., "Mechanical Properties of Concrete Materials Reinforced With Polyproplene or Polyethylene Fibers", ACI Materials Journal, Nov.-Dec. 1992, pp. 535-540.

Sun et al., "Growth of graphene from solid carbon sources," Nature, Nov. 25, 2010, vol. 468, pp. 549-552, Macmillan Publishers Limited.

Yamaguchi et al., "Soot Wear in Diesel Engines", Journal of Engineering Tribology, vol. 220, pp. 463-469, 2006.

\* cited by examiner

FACILE SYNTHESIS OF GRAPHENE, GRAPHENE DERIVATIVES AND ABRASIVE NANOPARTICLES AND THEIR VARIOUS USES, INCLUDING AS TRIBOLOGICALLY-BENEFICIAL LUBRICANT ADDITIVES

REFERENCE TO RELATED APPLICATIONS

This application claims the benefit of U.S. Provisional Patent Application No. 61/596,936, filed Feb. 9, 2012 and titled Tribologically Beneficial Carbonaceous Materials and Nano-Abrasive Lubricant Molecules From Intentional In-Situ Pyrolysis of Sacrificial Cyclic Carbon Constituents; U.S. Provisional Patent Application No. 61/579,993, filed Dec. 23, 2011 and titled Graphene and Graphene Derivatives Synthesis By Dehydration or Pyrolysis of Carbonaceous Materials, Vapor Exfoliation or PAH Formation, and Subsequent Hydrophobic Self-Assembly; U.S. Provisional Patent Application No. 61/568,957, filed Dec. 9, 2011 and titled Synthesis of Graphene, Graphene Derivatives, Carbon-Encapsulated Metallic Nanoparticles, and Nano-Steel, and the Use of Sequestered Carbonaceous Wastes and Greenhouse Gases in Such Synthesis Methods; U.S. Provisional Patent Application No. 61/546,368, filed Oct. 12, 2011 and titled Combustion Synthesis of Graphene Oxide and Graphene; U.S. Provisional Patent Application No. 61/541,637, filed Sep. 30, 2011 and titled Lubricating Additives, Polishing Compositions, Nanoparticles, and Tribological Coatings, and Uses Thereof, and Methods of Nanoparticle, Graphene, and Graphene Oxide Synthesis; U.S. Provisional Patent Application No. 61/538,528, filed Sep. 23, 2011 and titled Lubricating Additives, Polishing Compositions, Nanoparticles, and Tribological Coatings, and Uses Thereof, and Methods of Nanoparticle, Graphene, and Graphene Oxide Synthesis; U.S. Provisional Patent Application No. 61/503,203, filed Jun. 30, 2011 and titled Lubricating Additives, Polishing Compositions, and Nanoparticles, and Methods and Uses Thereof, and Methods of Nanoparticle Synthesis; U.S. Provisional Patent Application No. 61/491,633, filed May 31, 2011 and titled Lubricating Compositions, Lubricant Additives, Methods of Lubrication, and Methods of Polishing Surfaces; and U.S. Provisional Patent Application No. 61/452,781, filed Mar. 15, 2011 and titled Lubricating Compositions, Lubricant Additives, and Methods of Lubrication, wherein the contents of each are hereby incorporated herein by reference in their entirety.

BACKGROUND OF THE INVENTION

1. Field of the Invention

The invention pertains to methods of industrially-scalable ex situ synthesis of graphene, graphene oxide, reduced graphene oxide, and other graphene derivative structures, and nanoparticles and the uses therefor, including but not limited to composites, composite fabrication and coatings, the fields of tribology, nanotechnology, surface finishing, machining and tooling, boring, drilling, tunneling, ballistics, anti-ballistics, heat shielding, heat absorption, lubricant additives, lubricating compositions, coatings, methods of lubrication, methods of polishing hard surfaces, and methods of cutting, drilling, hardening, protecting, and fabricating steel and other hard surfaces. The invention further pertains to the use of abrasive nanoparticles in lubricating compositions for polishing, hardening, protecting, adding longevity to, and lubricating moving and stationary parts in devices and systems, including, but not limited to, engines, turbos, turbines, tracks, races, wheels, bearings, gear systems, and other physical and mechanical systems employing machined interacting hard surfaces, where the abrasive nanoparticles are formed in situ from the lubricating compositions or, in some cases, formed ex situ and then added to lubricants before their use.

2. Description of Related Art

Synthesis of Graphene and Graphene Derivatives.

Single-layer graphene, as a result of its observed and theoretical physical properties, including a large specific surface area, high intrinsic mobility, high Young's modulus (~1.0 TPa), high thermal conductivity (~5000 $Wm^{-1}K^{-1}$), high optical transmittance (~97.7%), low gas permeability, and high electron transport capacity, has been the subject of considerable study, research, and discussion in recent years (see, for example, Geim, et al., "The Rise of Graphene", *Nat. Mater.*, Vol. 6, pp. 183-191, 2007; and Zhu et al., "Graphene and Graphene Oxide: Synthesis, Properties, and Applications", *Adv. Mater.*, Vol. 22, pp. 3906-3924, 2010). Based on these properties of graphene, it has been considered for use in numerous applications such as photocatalysis, energy storage, solar cells, transparent electrodes, semiconductors, high strength/low weight composite materials, protective coatings, and field emission. Large-scale and economical production methods have, however, remained elusive.

Pure graphene is a planar polycyclic single atomic layer of pure carbon in a honeycomb-like lattice of six-membered $sp^2$-hybridized carbon rings. Graphene is theoretically a single pure layer of graphite, although the term graphene is conventionally also used to apply to a material with several stacked atomic layers of graphite or a graphitic layer with minor defects still having material properties similar to pure graphene. Graphene is relatively hydrophobic and is conventionally formed either by exfoliation of graphite, which may be done using supercritical carbon dioxide or by micromechanical cleavage, or by epitaxial growth on silicon carbide or certain metal substrates. Graphene may also be formed in the gas phase by passing liquid droplets of ethanol into argon plasma in an atmospheric-pressure microwave plasma reactor (Dato et al., "Substrate-Free Gas-Phase Synthesis of Graphene Sheets", *Nano Lett.*, Vol. 8, pp. 2012-2016, 2008).

Graphene nanotube synthesis has also been reported by an aerosol pyrolysis method (Pinault et al., "Carbon nanotubes produced by aerosol pyrolysis: growth mechanisms and post-annealing effects", *Diamond and Related Materials*, Vol. 13, pp. 1266-1269, 2004). A solution of 2.5-5 wt % of ferrocene in toluene or cyclohexane was aerosolized with argon and pyrolyzed at 800-850° C. The early stages of carbon nanotube formation were observed. A layer of nanoparticles believed to include iron was first formed on a solid substrate. An ordered carpet of nanotubes grew from this nanoparticle layer, with one nanotube growing from each of the nanoparticles. High-temperature annealing of the samples led to removal of iron from within the nanotubes and improved order in the nanotubes.

Several recent publications have reported the formation of graphene bonds under combustion conditions. In one case, minute quantities of nanoparticles of all four forms of carbon, namely diamond, graphite, fullerene, and amorphous, were detected in a paraffin candle flame (Su et al., "New insight into the soot nanoparticles in a candle flame", *Chem. Commun.*, Vol. 47, pp. 4700-4702, 2011). In another earlier case, small amounts of nanoparticle graphitic carbon were found upon acid treatment of the soot from a methane flame (Tian et al., "Nanosized Carbon Particles From Natural Gas Soot", *Chem. Mater.*, Vol. 21, pp. 2803-2809, 2009). In another earlier case, highly graphitic hollow nanotubes were formed from an ethanol flame (Pan et al., "Synthesis and growth mechanism of carbon nanotubes and nanofibers from ethanol flames", *Micron*, Vol. 35, pp. 461-468, 2004). Similarly, carbon nanotubes have been synthesized using $CO/H_2/He/C_2H_2$ gas mixtures burnt with an acetylene flame in the presence of laser-ablated iron or nickel nanoparticle catalysts (Vander Wal et al., "Flame Synthesis of Carbon Nanotubes using Catalyst Particles Prepared by Laser Ablation", *Am. Chem. Soc., Div. Fuel Chem.*, Vol. 49, pp. 879-880, 2004).

Polycyclic aromatic hydrocarbons (PAHs) form as part of the airborne "soot" contained in the residual particulate matter (PM) of incomplete combustion, pyrolysis, or other low-oxygen thermal degradation of hydrocarbons. As these PAHs are usually deemed undesirable byproducts of imperfect combustion, numerous studies have focused on how to minimize or eliminate altogether the formation of "soot" in combustion processes (see, for example, Coppalle et al., "Experimental and Theoretical Studies on Soot Formation in an Ethylene Jet Flame", *Combust. Sci. and Techn.*, Vol. 93, pp. 375-386, 1993).

PAHs have a substantially planar structure of fused aromatic carbon rings with hydrogen atoms bound to the peripheral carbon atoms of the matrices. PAHs may be thought of as miniature nanoscopic scales of graphene.

Graphene derivatives include structures having graphitic bonds partially incorporating heteroatoms such as oxygen or other structural imperfections in the carbon lattice. Graphene derivatives, as described herein, also include structures such as nanotubes, nanobuds, fullerenes, nano-peapods, endofullerenes, nano-onions, graphene oxide, lacey carbon, and other non-graphene forms of graphitic carbon which may contain structural or chemical imperfections.

Graphene oxide (GO) is a family of impure oxidized forms of graphene that includes hydroxyl and epoxide groups bonded to various carbon atoms in the lattice matrix. The structural properties of GO have been extensively studied (see Mkhoyal et al., "Atomic and Electronic Structure of Graphene-Oxide", *Nano Lett.*, Vol. 9, pp. 1058-1063, 2009), yet the exact chemical structure of GO is still the subject of much debate and considerable variability, at least in terms of hydroxyl and epoxide group frequency and location observed in the various samples studied.

GO is also known to include carboxylic acid groups believed to be located at the edges of the carbon sheets. These various functional groups permit further chemical functionalization of GO. Recently, the conversion of carboxyl groups to hydroxyl groups in a graphene derivative has been reported to produce a material that has been called "graphenol". Various complex and multi-step methods to convert this graphenol to graphene via pyrolysis have been reported, yet these methods include the use of toxic chemicals such as hydrazine (see U.S. Pat. App. Pub. No. 2011/0201739, by Beall, entitled Method and System for Producing Graphene and Graphenol and published on Aug. 18, 2011).

Not unlike graphene, GO is conventionally formed from exfoliated graphite oxide or by oxidation of graphene itself. GO sheets may be purposefully formed in a wide range of oxidation levels with measured oxygen-to-carbon ratios as high as around 1:2. As graphene oxide has its own unique physical and chemical characteristics apart from graphene, its structural variability has made it less attractive for many experimental studies. As opposed to graphene, GO is hydrophilic and an electrical insulator of high stiffness and high strength (see Dreyer et al., "The chemistry of graphene oxide", *Chem. Soc. Rev.*, Vol. 39, pp. 228-240, 2010).

Graphene oxide was first prepared by the treatment of graphite with potassium chlorate and fuming nitric acid (see Brodie, "On the Atomic Weight of Graphite", *Proc. of the Royal Soc. of London*, Vol. 10, p. 249, 1859). A somewhat more efficient process employed sulfuric acid, sodium nitrate, and potassium permanganate to convert graphite to graphene oxide (see Hummers et al., "Preparation of Graphitic Oxide", *J. Am. Chem. Soc.*, Vol. 80, p. 1339, 1958). Recently, a still more efficient method was reported using sulfuric acid, phosphoric acid, and potassium permanganate (see Marcano et al., "Improved Synthesis of Graphene Oxide", *ASC Nano*, Vol. 4, pp. 4806-4814, 2010).

Colloidally-dispersed GO in water may be chemically reduced to graphene using hydrazine monohydrate. Other chemical reductants for GO include hydroquinone, gaseous hydrogen, and strongly basic solutions. Thermal exfoliation and reduction of GO occurs upon heating to 1050° C. with extrusion to remove the generated byproduct of carbon dioxide gas. Finally, electrochemical reduction of GO may be accomplished by placing electrodes at opposite ends of a GO film on a non-conductive substrate, followed by the application of an electrical current to the film.

Although to date a complete reduction of GO to graphene has not been reported in the literature, GO may be reduced by a number of different processes to produce so-called "rGO" (reduced graphene oxide) with measured oxygen-to-carbon ratios as low as about 1:24.

It is noteworthy that rGO has been observed to exhibit many chemical, physical, and electrical properties more similar to those of graphene than to those of GO.

Graphene and its many derivatives are currently the subject of numerous studies and widespread research, in part because of their many potential applications, including but not limited to lubricants, molecular level coatings for composite reinforcement, heat shielding, ballistic transistors, integrated circuits and reinforced fibers and cables.

Use of Sequestered Waste Carbon in Graphene Production.

Various forms of carbon waste sequestration are known to the art, including, but not limited to, the conversion of carbonaceous wastes to things like "biochar" or synthetic methanol from carbon dioxide (see, for example, Hogan et al., "Biochar: Concept to Sequester Carbon", *Encyclopedia of Earth, National Council for Science and the Environment*, Washington, D.C., 2011; Jiang et al., "Turning carbon dioxide into fuel", *Phil. Trans. R. Soc. A*, Vol. 368, pp. 3343-3364, 2010), yet the beneficial use of such sequestered or captured carbon wastes as carbonaceous feedstock or promoters in the synthesis of graphene remains unreported.

Implantable Medical Prosthetic Devices.

An important factor in the success of implanted medical prostheses is the uniformity of the friction surfaces, both for longevity and prevention of infection purposes. Asperities on the surface of medically implanted metallic devices provide a location to harbor bacteria. For metallic devices in the vasculature or circulatory system, they also provide a location for dangerous platelet aggregation that can lead to heart attack or stroke. The nanopolishing of such implantable medical prosthetic devices to near atomic-level perfect smoothness would greatly advance the safety and efficacy of such devices.

Nano-Pharmaceuticals, Oncology, and Medical Imaging.

Improvements in the targeting of radiation or chemotherapeutic drugs to a cancer site and the ability to provide contrast for medical imaging are areas of active research in the medical field. Magnetite nanoparticles have been used as a tumor contrast agent for magnetic resonance imaging (see, for example, Tiefenauer et al., "In vivo evaluation of magnetite nanoparticles for use as a tumor contrast agent in MRI", *Magnetic Resonance Imaging*, vol. 14, no. 4, pp. 391-402, 1996). There is considerable current study and research into the use of "functionalized" buckyballs as a means to deliver targeted drug therapies to tumors in the body (see, for example, Yoon et al., "Targeted medication delivery using magnetic nanostructures", *J. Phys.: Condens. Matter*, vol. 19, 9 pages, 2007).

Steel Production.

Pits and asperities on the surface of steel provide a surface for the formation of destructive oxidation in the form of ferric oxide, also known as rust. The reduction or elimination of these pits and asperities would increase the longevity of such steel structures.

Graphene and GO Reaction Environments.

In some embodiments of the invention, graphene and graphene oxide structures are used in various solvents to act as reaction envelopes, which create a nano-environment for reactions to occur that are thermodynamically or otherwise unfavorable similar to the way enzymes work in biological systems. These graphene reaction envelopes (GREs) and graphene oxide reaction envelopes (GOREs) permit chemical reactions and atomic reformations, such as restructuring atoms into crystals, to occur which would not normally occur outside the reaction envelope. The GRE or GORE serves as a "micro- or nano-reaction vessel" and then may pinch off part of the envelope into a nanoabrasive or other nanoparticle, thereby becoming part of the reaction product. In one embodiment, the envelope acts as a nano-blast furnace for the production of nano-steel from iron.

Steel may take on a number of different forms, including, but not limited to ferrite, austenite, pearlite, martensite, bainite, ledeburite, cementite, beta ferrite, hexaferrum, and any combination of these, depending on the conditions under which it is made. Nano-steels of the invention formed in GREs or GOREs may be in the form of ferrite, austenite, pearlite, martensite, bainite, ledeburite, cementite, beta ferrite, hexaferrum, and any combination of these.

Nanosteel, Nanorobotics and Nanomachine Fabrication.

Nano-crystalline metallic alloy synthesis is known in the art (Alavi et al., "Alkaline-Earth Metal Carbonate, Hydroxide and Oxide Nano-Crystals Synthesis Methods, Size and Morphologies Consideration", pp. 237-262 in *Nanocrystals*, ed. by Matsuda, InTech, Rijeka, Croatia, 2011). Synthesis of steel-reinforced nanoparticles, nano-onions, and methods of producing neat nano-steel crystals and nanoscopic metal sheets, however, remain unreported.

Nanorobotics commonly refers to the science of nanotechnology engineering and fabrication of mechanical devices in the range of 0.1 to 10 µm in size from nanoscale components. Other common names for these theoretical devices are nanobots, nanoids, nanites and nanomites. It is postulated that future developments in this field will allow the construction of, among other things, tiny remotely operated surgical instrumentation and nanoscale electronic devices. Easy and inexpensive methods of nano-fabrication of tiny steel crystals or billets would likely advance this science considerably.

Concreting and Asphalting Technology.

Concrete and asphalt concrete are two common composite materials used in construction. Concrete is a composite formed minimally of a cementitous material, a fine aggregate, a coarse aggregate, and water. Asphalt concrete is a composite typically formed minimally of asphalt, a highly viscous, sticky black tar-like substance present in some crude petroleums and natural deposits, and a coarse aggregate. Many types of admixtures and additives have been developed over the years in an attempt to increase the strength of these materials.

The most pervasive of these concrete "additives" fall into two general categories: water-reducing superplasticizers (also known as high-range water reducers) and synthetic reinforcing fibers used to produce fiber-reinforced concrete (FRC). The superplasticizers, including the latest generation of polycarboxylate ether based superplasticizers (PCEs) and polypropyleneglycol-derivative admixtures, serve to reduce the amount of water required to form the composite. Superplasticizers also improve the rheology (flow characteristics) of the concrete slurry, thereby improving workability prior to cure (see Palacios et al., "Effect of superplasticizer and shrinkage-reducing admixtures on alkali-activated slag pastes and mortars", *Cement and Concrete Research*, Vol. 35, pp. 1358-1367, 2004; Aitcin et al., "Superplasticizers: How they Work and Why The Occasionally Don't", *Concrete International*, Vol. 16, pp. 45-52, 1994).

In the case of FRC, the synthetic fibers (typically polypropylene fibers), are intended to increase the strength of the matrix and improve the concrete's deformability. Concrete reinforcing fibers are meant to bridge micro-cracks in concrete and reduce separation, thereby allowing the concrete to maintain its ability to support its load without failure from complete separation along cracks (see Soroushian et al., "Mechanical Properties of Concrete Materials Reinforced With Polyproplene or Polyethlene Fibers", *Materials Journal*, Vol. 89, pp. 535-540, 1992).

In practice, neither type of "additive" has shown dramatic increases in the strength of the concrete or asphalt concrete products or systems. It is believed that graphene and certain graphene derivatives could be used as reinforcing "additives" to concrete and asphalt in lieu of the methods of the current state of the art.

Military and Ballistics Science.

According to recent research at Columbia University (New York, N.Y., United States), graphene is identified as the strongest material on Earth. The inordinate strength of graphene is attributed by the Columbia researchers to its covalent carbon-carbon bond matrix. The graphene samples tested were defect-free monolayers of graphene. Testing of the samples revealed that a single sheet of graphene has an intrinsic strength of 42 $Nm^{-1}$.

Modern anti-ballistics science seeks to develop ever-increasing thinner means of providing protection from ballistic projectiles and shrapnel. Towards this end, new means for molecular reinforcement of polymer-matrix-composites (PMCs) are continually being investigated. The current state of the art employs several varieties of high-performance ballistic yarns and fibers, including S-glass, aramids (e.g., Kevlar® 29, Kevlar® 49, Kevlar® 129, Kevlar® KM2, Twaron®), highly oriented ultra high molecular weight polyethylene (e.g., Dyneema®, Spectra®), PBO (e.g., Zylon®) and Polypyridobisimidazole (PIPD) (referred to as M5®) etc.

Typical characteristics of these fibers are very low density and high tensile strength, with correspondingly high energy absorption capacity. In the case of polymer matrix composite (PMC) ballistic panels, the fibers' force-dispersing deformation ability is severely hampered by the surrounding resin of the composite, which leads to failure under conditions of fracture and delamination of the resin matrix upon impact from a projectile. Graphene and its derivatives, incorporated into textile composite ballistic panels, would not suffer from the same limitations as typical PMC resin-matrices.

Graphene and its derivative structures represent a unique opportunity and material for anti-ballistics. Graphene and its derivatives have particularly high elastic moduli and tensile strength, with a Young's modulus of ~1000 Gpa and a strength of around 13-53 Gpa. In comparison to traditional anti-ballistic fibers and composites, the potential of graphene and its derivatives far outshine the methods of the current state of the art.

A company known as Nanocomp Technologies Inc. (Concord, N.H., United States), working in conjunction with the U.S. Army's Natick Soldier Center, is seeking to develop a new generation of lightweight ballistic armor based on carbon nanotube (CNT) technology. In April of 2009, the company reportedly demonstrated that a ~5 mm thick CNT-composite ballistic panel was able to stop a 9 mm bullet. Additional advancements in industrially-scalable graphene and graphene-derivatives synthesis would undoubtedly move this technology closer to commercialization.

Lubrication of Mechanical Systems.

All mechanical systems involve friction between interacting constituent parts. Such interaction can be as simple as a ball bearing sliding along a race, a piston ring moving against a cylinder sleeve, or the contact between the lobe of a camshaft and its cam follower. In all of these examples, friction between the interacting surfaces is a factor to be considered. Friction in any system is the cause of stress, fatigue, wear, heat, noise, vibration, and eventually failure. The other common enemy of the aforementioned metal-containing mechanical systems is corrosion.

In most circumstances, engineering science seeks to reduce the friction inherent in physical and mechanical systems with interacting surfaces by machining and finishing those surfaces to the highest practical smoothness. No current friction surface is perfectly smooth, that is to say, completely free of asperities. Interaction of these uneven surface asperities increases friction. As needed, interacting components of physical and mechanical systems are machined and polished to required tolerances to permit proper performance and reduce inherent friction. Marked reduction in friction through so-called "super-polishing" of components to high tolerances ($R_a$<50 nm) to date has meant substantial additional production time and costs. Generally, modern machining science is forced to trade machining exactitude for economy.

Additionally, all internal combustion engines, including gasoline and diesel, both normally aspirated and turbocharged, turbines, and other gear-containing systems require lubrication for proper operation. Various attempts at providing optimum lubrication of these machines have been made in the field of engine and gear lubrication since their inception. The first such attempts at lubrications, such as olive oil and certain carbolic soaps, have since been replaced with more sophisticated hydrocarbon-based lubricants, many containing even more sophisticated additive packages and each such additive attempting to address various inherent problems in lubricating these systems.

The current state of the art for lubrication of metal-containing mechanical systems, such as internal combustion engines, is the use of elasto-hydrodynamic lubrication (EHL) techniques that utilize methods and materials to "deal with" the problem of asperities on interacting metallic surfaces of mechanical systems by employing incompressible fluids and barrier coatings to prevent metal-to-metal contact. None of these methods affect the so-called $R_a$ (Roughness Average) values of the interacting metallic component surfaces and do nothing to ameliorate the friction-causing effects of the asperities themselves.

To preserve and protect metal friction surfaces and the systems that include them, various lubricant additives are used for a variety of purposes, such as dispersants, corrosion inhibitors, viscosity improvers, seal swell agents, pour point depressants, foam inhibitors, anti-wear agents, and antioxidants. Some lubricant additives that have been developed to reduce friction include the following: triorthocresyl phosphate (TOCP, or simply TCP), popular in aviation lubricants but known to slowly attack elastomer gaskets and seals; naphthenic hydrocarbon detergents, known to combine with the products of incomplete combustion to form hydrochloric acid; zinc dialkyldithiophosphates (ZDDPs), problematic to vehicles equipped with catalytic converters; chlorinated paraffins, identified globally as extremely harmful to aquatic life; suspended solids such as polytetrafluoroethylene (PTFE, trade name Teflon®), considered undesirable for lubrication by many; graphite powder, considered by many to be undesirable in systems employing bearings; molybdenum, a metal reported to reduce fuel economy; tungsten disulphide nano-onions, a temporary barrier solution; Buckminsterfullerenes, another expensive and temporary solution, and nanodiamonds suspended in graphite to discourage typical aggregation of the abrasive particles, again invoking complaints by those who object to graphite employed in systems containing bearings. Lubricant additives often also contain phosphates and sulfides that upon decomposition, can contribute to the production of noxious gases.

Carbonaceous deposits within mechanical systems are almost universally considered undesirable, so many modern lubricants are specifically designed and formulated to inhibit and/or prevent the formation of any carbonaceous deposits. Conventional EHL wisdom suggests that internal combustion engine oil lubricants must be formulated to be as physically and chemically stable as possible to resist thermal degradation of the base lubricant and its additives by incomplete combustion and pyrolysis, not encourage it; this because the products of such thermal breakdown of conventional lubricants produce harmful carbonaceous deposits (such as sludge) that tend to clog valves, coat piston rings and generally decrease the operating efficiency and life expectancy of an engine. Dispersants are commonly used in lubricants to prevent the aggregation of sludge (see, for example, Won et al., "Effect of Temperature on Carbon-Black Agglomeration in Hydrocarbon Liquid with Adsorbed Dispersant", *Langmuir*, Vol. 21, pp. 924-932, 2005; Tomlinson et al., "Adsorption Properties of Succinimide Dispersants on Carbonaceous Substrates", *Carbon*, Vol. 38, pp. 13-28, 2000; Wang, "Synthetic and Characterization of Ethylene Carbonate Modified Polyisobutylene Succinimide Dispersants", University of Waterloo Masters Thesis, 2010). Blow-by soot from the engine that is the result of incomplete combustion has been shown to be highly abrasive and capable of damaging metal parts (see, for example, Jao et al., "Soot Characterisation and Diesel Engine Wear", *Lubrication Science*, Vol. 16, pp. 111-126, 2004; Ryason et al., "Polishing Wear by Soot", *Wear*, Vol. 137, pp. 15-24, 1990; Yamaguchi et al., "Soot Wear in Diesel Engines", *Journal of Engineering Tribology*, Vol. 220, pp. 463-469, 2006; Gautam et al., "Effect of Diesel Soot Contaminated Oil on Engine Wear—Investigation of Novel Oil Formulations", *Tribology International*, Vol. 32, pp. 687-699, 1999). "Ashless" engine oils are another example of products supporting the notion that lubricating formulations must be kept as free of carbon particles as possible and that all carbonaceous engine deposits are harmful and bad. Under the current EHL paradigm, thermal degradation and pyrolysis of lubricant additives resulting in the formation of carbonaceous soot and deposits is universally deemed undesirable.

The current testing standards for lubricants and their additives are further evidence of, and support this, lubrication paradigm. The Noack Volatility Test (ASTM D5800) measures vaporization of the lubricant formulation as a function of temperature, because formulations become more viscous with increased vaporization. The test involves putting a mass of motor oil into a Noack device at 250° C. with a constant flow of air over the sample for 1 hour. Then the sample then is weighed to determine loss of mass due to loss of volatile organic compounds (VOCs). The acceptable loss in mass is to be no greater than ~13 to 15%. A lubricant must pass this test to earn approval under the API CJ-4 motor oil standard (United States) or the ISLAC GF-4 motor oil standard (European Union).

Other lubricant industry evaporation tests include ASTM D972 and ASTM D2595. ASTM D972 tests the lubricant formulation at temperatures between 100 and 150° C. with a constant flow of air (2 L/min) over the sample. ASTM D2595 tests the lubricant formulation at temperatures between 93 and 316° C. with a constant flow of air (2 L/min) over the sample.

The modern lubricant industry almost exclusively uses a base lubricant of linear or branched chain hydrocarbons in EHL lubricating formulations, along with relatively small amounts of a combination of comparatively expensive additives, including, in some cases, cyclic-carbon containing additives such as certain antioxidant "hindered" phenols, certain salicylates, and certain amines. Most often, use of cyclic-carbon containing lubricant antioxidant additives in the prior art is limited to efforts to improve or protect the underlying base lubricant mostly by inhibiting its oxidation from the radicals of in situ formed peroxides.

The entire aforementioned EHL lubrication paradigm and the industry testing standards are based upon the premise that carbonaceous products of incomplete combustion or pyrolysis are universally harmful and undesirable inside of engines and mechanical systems. This suggests that the optimal result of use of lubricants containing detergents, dispersants, and boundary films is to maintain the lubricated internals of a mechanical system as perfectly clean and free of carbonaceous deposits and free of abrasive wear as possible.

Production and Use of Fullerenes in Lubrication.

Fullerenes, first discovered in 1985 and named after the late geodesic dome architect Buckminster Fuller, are a class of molecules with outer shells composed entirely of carbon rings. The basic spherical variety of fullerene is buckminsterfullerene or simply, a "buckyball". Buckyballs can be endohedral in nature, with various atoms, ions, or complexes trapped inside their hollow cores. Endohedral metallofullerenes, which contain metallic ions, are the subject of significant current scientific inquiry and study.

In mathematical terms, a buckyball is a trivalent convex polyhedron comprised of pentagonal and hexagonal carbon rings. Buckyballs follow Euler's polyhedron formula, in that V−E+F=2, where V, E, and F are the number of vertices, edges, and faces on the exterior of the ball. In terms of the non-isomorphic fullerenes, there are some 214,127,713 different varieties. Pure simple buckyballs are commercially available in $C_{60}$ and $C_{70}$ configurations, but are quite expensive; generally, $900 to $1,000 per 100 mg of material.

Bucky-diamonds are nanoscale carbon complexes of a diamond core within a fullerene or fullerene-like outer shell (see, for example, Barnard et al., "Coexistence of Bucky-diamond with nanodiamond and fullerene carbon phases", *Physical Review B*, Vol. 68, 073406, 2003). This structure is now believed to be an intermediary structure between the interconversion of nano-onions and nanodiamonds. Barnard et al. predict Bucky-diamonds to be a metastable form of carbon as the coexistence of nanodiamond and fullerene in a size range of ~500 to 1,850 atoms (~1.4 to 2.2 nm in diameter).

Barnard et al. ("Substitutional Nitrogen in Nanodiamond and Bucky-Diamond Particles", *J. Phys. Chem. B*, Vol. 109, pp. 17107-17112, 2005) present that it is possible to incorporate heteroatoms, such as nitrogen in this case, into the Bucky-diamond structure. Recently, Yu et al. ("Is There a Stable Bucky-diamond Structure for SiC Cluster", submitted to the *Journal of Chemical Physics* on Aug. 24, 2011) proposed a stable $Si_{68}C_{79}$ Bucky-diamond structure based on computer molecular modeling. In the stable state, the nanodiamond core and the fullerene-like shell are not believed to be chemically bonded to each other. The Yu et al. modeling predicted that upon heating of this Si—C structure, the 35-atom core would decompose at a lower temperature than the 112-atom shell, the core then becoming incorporated into the shell to form a larger retained fullerene-like shell structure upon cooling.

Fullerenes are a promising new nanotechnology in lubrication science. There have been many attempts to use fullerenes as barrier lubricants to fill asperities and provide a tribological film on moving parts. Unfortunately, large-scale and commercially-viable means for the production of useful fullerenes has proven elusive. Again, the current state of the art in tribology has focused on tribological films and coatings on the surfaces of moving parts. However this old paradigm does not address the underlying cause of friction itself, the asperities on the interacting metal parts.

The advent of nanotechnology and the science of tribology have introduced several new approaches to lubrication through the use of various nanoparticles. U.S. Patent Application Publication No. 2007/0292698, entitled "Trimetaspheres as Dry Lubricants, Wet Lubricants, Lubricant Additives, Lubricant Coatings, Corrosion-Resistant Coatings and Thermally-Conductive Materials" by Gause and published Dec. 20, 2007, discloses the use of scandium-containing metallofullerene buckyballs as a suspended solid lubricant, in place of simple carbon fullerenes or "buckyballs", which rapidly degrade at elevated temperature.

The use of externally separated singular nano-Buckydiamonds (SNBDs) as lubricant additives has been postulated, however these molecules are inherently difficult to separate from undesired agglomerates, a necessary step to make them useful in lubrication and other applications (See for example, Ho, D. (ed.), *Nanodiamonds: Applications in Biology and Nanoscale Medicine*, Ch. 1, "Single-Nano Buckydiamond Particles, Synthesis Strategies, Characterization Methodologies and Emerging Applications", by Ōsawa, E., Springer Science+Business Media, LLC, New York, 2010).

NanoMaterials, Ltd. (Nes Ziona, Israel) has produced a series of tungsten disulfide nanopowder-containing lubricants. These black tungsten sulfide onion structures are intended to fill surface asperities and shed layers to act as a low-friction interaction barrier surface between interacting metal engine components.

NanoLube, Inc. (Lombard, Ill., United States) claims to produce non-abrasive carbon nanospheres, under the name DiamondLube™, that are introduced into lubricants to reduce friction. The NanoLube™ product appears to be expensive but simple fullerenes suspended in lightweight oil.

PlasmaChem GmbH (Berlin, Germany) markets an additive for motor oils under the trademark ADDO®, which is claimed to contain diamond and graphite nanoparticles formed by detonation synthesis capable of polishing internal engine parts to mirror-like smoothness. The graphite is presumably added to the suspension to reduce agglomeration of the nanodiamonds.

Detonation nanodiamond is a nanodiamond product typically formed by explosive detonation of an oxygen-deficient mixture of trinitrotoluene and hexogen (see, for example, Mochalin et al., "The properties and applications of nanodiamonds", *Nature Nanotechnology*, Vol. 7, pp. 11-23, 2012). The resulting nanodiamonds are usually in the form of 1-1 μm clusters of 5 nm diamondoid particles, each nanoparticle comprising a diamond core with a layer of surface functional groups.

Other methods of forming nanodiamonds use non-detonation techniques, such as laser ablation, high-energy ball milling of diamond microcrystals, plasma-assisted chemical vapor deposition, autoclave synthesis, chlorination of carbides, ion irradiation of graphite, electron irradiation of carbon nano-onions, and ultrasound cavitation. These resulting non-detonation nanodiamonds have a tendency to cluster upon synthesis, and much effort has been devoted to developing processes to cleanly separate the agglomerated nanodiamond products.

The common element in the majority of these solutions to friction reduction, as well as the current state of the art, is the use of elasto-hydrodynamic lubrication (EHL) techniques that utilize methods and materials to "deal with" the problem of asperities on interacting metallic surfaces of mechanical systems, not to remove or "solve" the root cause of the problem—the asperities themselves. Those methods and materials that do attempt to address polishing and reduction of asperities do so by employing externally added nanodiamond abrasives that must be suspended in materials employed to prevent their agglomeration into undesirably large clusters. None of the aforementioned methods and materials involve techniques or the means for in situ formation of beneficial carbonaceous tribological particles or nano-abrasives from liquid precursors, a novel approach that addresses the inherent problem in the current state of the art of undesired particle agglomeration from externally-added nanodiamond lubricant abrasives.

SUMMARY OF THE INVENTION

The invention relates to methods for the facile synthesis of graphene, graphene derivatives and nanoparticles and their use as tribologically-beneficial lubricant additives. The products of the methods of the invention have numerous applications in many fields, including, but not limited to, tribology, nanotechnology, machining and tooling, lubrication, metalworking, drilling, mining, paint manufacturing, anti-corrosion coating manufacturing, rock tunneling, routing, mould fabrication, optical lens manufacturing, military engineering, gem cutting and polishing, aerospace engineering, automotive engineering, high-speed rail, marine engineering, medicine, nuclear medicine, medical imaging and diagnostics, trucking, cranes and heavy equipment manufacturing, farm equipment manufacturing, motorcycle manufacturing, electric motor fabrication, cable and wire manufacturing, sanding, nuclear, solar, wind and conventional electric power generation, hydroelectric power generation, electronics, integrated circuit technology, battery technology, polishing compound manufacturing, steel manufacturing, metal polishing, and chemical hardening of metal surfaces.

The invention further relates to lubricating compositions comprising a lubricant and at least one additive selected to serve as a sacrificial carbon source in the in situ formation of tribologically-useful graphitic carbon structures under normally operating locally pyrolytic conditions. Additionally, methods for ex situ synthesis of graphene, graphene oxide, reduced graphene oxide, and other graphene derivative structures and abrasive nanoparticles are disclosed. The means for separating the ex situ synthesis products are further revealed by use of a "dynamic furnace" apparatus.

Additionally, the invention is particularly useful as it pertains to lubricating compositions and methods for polishing, hardening, and lubricating moving parts in engines, turbos, turbines, tracks, races, wheels, bearings, shafts, transmissions, gear systems, and other physical and mechanical systems employing machined interacting hard surfaces. In one embodiment, the methods and lubricating compositions provide, among other things, near frictionless perfection in metallic interacting surfaces.

In one embodiment, the lubricating composition of the invention allows the engine, turbo, or turbine to produce greater useful horsepower and torque than when lubricated with a conventional lubricant because friction is decreased through the lubricating and polishing effect of the lubricating compositions and methods. Efficiency indicators such as engine horsepower and torque are observed to increase over a time period of days, to weeks, to months of normal use after the initial introduction of the lubricating composition to the engine. In some embodiments, the benefits from the methods and lubricating composition disclosed herein include formation of a tribological boundary of nanoparticles or nanosheets on the surfaces of lubricated moving parts, where such nanoparticles or nanosheets serve to actively remove oxidation from the metal surface, encapsulate it, and make beneficial use of the oxidation molecules in the performance of an intended role in friction reduction.

In the case of medicine, nuclear medicine, medical imaging, and diagnostics, the invention produces highly inert, safe and infinitesimally small vectors for delivering radioactive isotopes, other metal ions, or other therapeutic agents bound to ions, to locations within the body for therapeutic reasons or to enhance the resolution of magnetic or other diagnostic images. Additionally, these magnetic or paramagnetic spheroids may be used to eradicate tumors and cancer cells in an artificially-induced strong magnetic field, such as in magnetic resonance imaging (MRI), to force the spheroids to rotate or oscillate violently, thereby producing heat sufficient to thermally obliterate the targeted cells or tissues from within.

In one embodiment, the invention comprises an economical dehydration reaction or reflux pyrolysis to form graphitic carbon from a carbonaceous material carbon source. The methods are upscalable for industrial production. The carbon source is preferably a sugar or other 6 carbon ring-containing structure, although other carbonaceous materials may be subjected to dehydration, pyrolysis, oxidation or incomplete combustion to serve as the carbon source. The carbon source is subjected to reflux pyrolysis, oxidation/reduction, incomplete combustion or acid dehydration to form the graphitic carbon reactant starting material. In one embodiment, graphitic carbon is subjected to a refluxing with a liquid solvent, and graphene/graphene oxide (GO) is emitted as nanoscopic scales or "nanoscales" suspended in a vapor/steam. In one embodiment, a graphitic carbon source can be subjected to physical attack by a highly-pressurized liquid or vapor to produce mechanically exfoliated graphene scales without the need for a pyrolysis, dehydration, or oxidation step. The resulting graphene/GO scales can travel in the vapor and be collected either by direct deposition onto a solid substrate in physical contact with the emitted vapor, or by applying the particle-containing vapor to an aqueous solution or liquid used to promote "hydrophobic self-assembly" of the scales into larger graphene/GO sheets.

In one embodiment, the reaction environment is controlled to limit the amount of ambient oxygen ($O_2$) in the chamber, discouraging complete combustion of the reactants during heating. In one embodiment, the reaction is carried out in the presence of an added solvent. In one embodiment, the produced GO is converted to reduced graphene oxide (rGO) or graphene sheets suspended in a heated or unheated liquid collection medium. The resulting rGO or graphene sheets can be used to produce a wide range of useful products, including, but not limited to, protective coatings, and low weight/high strength graphene-reinforced composites, wires, and fibers.

In one embodiment, a carbonaceous starting material is subject to a dehydration reaction or pyrolysis to form graphitic carbon. In one embodiment, the carbonaceous source is graphitic. The graphitic carbon is subjected to refluxing in the presence of a solvent causing graphene/GO scales or reflux synthesized polycyclic aromatic hydrocarbons (PAHs) to be emitted in a resulting vapor upon heating. The graphene/GO scales or PAHs are collected either by deposition onto a solid substrate in physical contact with the emitted vapor or by applying the vapor to an aqueous liquid pool for graphene/GO hydrophobic self-assembly. The process is industrially-scalable. In some embodiments, the produced GO is converted to reduced graphene oxide (rGO) sheets suspended in a heated or unheated liquid medium.

In one embodiment, the invention relates to the production of abrasive nanoparticles useful as polishing agents. Abrasive nanoparticles, according to this embodiment, can be created by the addition of a metal oxide or nanodiamonds to the reaction mixture.

In one embodiment, the resulting graphene sheets may be used to produce a range of useful products, including, but not limited to, low-weight, high-strength, graphene-reinforced composites.

In one embodiment, suitable additives to conventional lubricants promote the in situ formation of tribologically-useful graphitic carbon-containing nanoparticles or microparticles in tribologically-effective amounts. In one embodiment, the additive comprises a chemical structure having at least one carbon ring. In one embodiment, the nanoparticles are abrasive nanoparticles that act as nano-polishing agents to nano-polish friction surfaces to a high smoothness by reduction or removal of asperities, thereby reducing the friction between the wear surfaces. In one embodiment, the additive to the lubricant comprises a form of graphitic carbon which is formed ex situ prior to addition to the lubricant to form a lubricating composition.

In one embodiment, the additive to the lubricant comprises an iron complex molecule. In one embodiment, the additive comprises nanoparticles of carbon-containing particulate matter. In one embodiment, the additive is dissolved in the lubricant to form the lubricating composition. In one embodiment, the additive is miscible with the lubricant to form the lubricating composition. In one embodiment, a carbon-containing precursor molecule in the form of one or more sugar or sugar-like amphiphiles, is employed to provide a sugar or sugar-like component in the lubricating composition that does not tend to congeal or clog internal components of the system. In one embodiment, cyclic carbon-containing precursor molecules are added to the lubricant in the form of an existing commercially available solution that already contains such precursors. The synthesized graphitic carbon does not improve the inherent physical lubricating properties of the conventional base lubricant, but rather acts to transfer and absorb heat, form tribological coatings on internal parts, and convert into nano-abrasives that promote nano-polishing of metal surfaces of the lubricated system resulting in friction reduction.

In one embodiment, further reduction of friction and increased efficiency in lubrication is achieved by using a conventional lubricant having a lower viscosity than other conventional lubricants. The effective elimination of asperities by nano-polishing eliminates the need to use viscous formulations that are typically intended to adhere to the asperities under high sheer. The smoothness of the wear surfaces also allows operation of an engine with a thinner film of lubrication, which results from using a lower viscosity fluid, between two wear surfaces without damaging the metal parts. The lower-viscosity base fluid provides less resistance to moving parts, thereby improving the efficiency of the lubricating system and mechanical system it is lubricating.

In one embodiment, the methods deliver and produce a friction-reducing film or coating to internal mechanical system parts via the circulating lubricating composition while additionally making use of naturally occurring engine combustion products to produce a film or coating. In other embodiments, the methods deliver and produce a friction-reducing film or coating via the circulating lubricant alone.

In one embodiment, the lubricating compositions improve engine, turbo, turbine, gear, or other component or system performance. In one embodiment, the lubricating compositions provide tribological friction-reducing films and coatings to automotive and aerospace lubricating oil compositions and applications, including the lubrication of gear, bearing, or journal systems. In some embodiments, the lubricating compositions reduce the friction between wear surfaces by micro-polishing the wear surfaces to a lower surface roughness over time while lubricating the system during operation.

In one embodiment, the lubricating compositions combine with naturally-occurring combustion products and by-products by chemical reaction to provide tribological friction-reducing films and coatings to friction surfaces of automotive and aerospace mechanical parts. In one embodiment, additives in the lubricating compositions combine by chemical reaction with each other to provide tribological friction-reducing films and coatings to friction surfaces of automotive and aerospace mechanical parts.

In one embodiment, the invention comprises a method of synthesis of graphene comprising refluxing a reaction mixture comprising at least one solvent and at least one carbonaceous material promoting polycyclic aromatic hydrocarbon formation under conditions that inhibit complete combustion of the carbonaceous material, thereafter collecting vapors produced by the reflux of the reaction mixture, directing the vapors to a substrate, whereupon graphene is deposited on the surface of the substrate; and recovering graphene from the surface of the substrate.

In one embodiment, the invention comprises a method of graphene oxide production comprising refluxing a reaction mixture comprising at least one solvent, at least one oxidizer and at least one compound promoting polycyclic aromatic hydrocarbon formation under conditions to prevent the complete combustion of the carbon source into carbon dioxide or carbon monoxide, thereafter collecting a vapor stream produced by the reflux of the reaction mixture, thereafter directing the vapor stream to a substrate, whereupon graphene oxide is deposited on the surface of the substrate and recovering graphene oxide from the surface of the substrate.

A lubricating composition comprising a base lubricant and at least one carbon-containing additive that forms, under locally pyrolytic conditions, a tribologically-effective amount of at least one graphitic carbon-containing structure.

In one embodiment, the invention comprises a lubricating composition comprising a base lubricant and graphene, wherein the graphene was formed prior to combination with the base lubricant.

In one embodiment, the invention comprises a lubricating composition comprising a base lubricant and one or more Bucky diamonds, wherein at least some of the Bucky diamonds comprise iron or an iron-containing molecule.

In one embodiment, the invention comprises a method of lubricating a mechanical system comprising at least one internal friction surface having asperities, the method comprising operating the mechanical system with a lubricating composition comprising a nano-polishing agent to remove the asperities from the internal friction surface, wherein the lubricating composition comprises at least one carbon-containing additive that forms in situ, under locally pyrolytic conditions within the mechanical system, at least one nano-polishing agent.

In one embodiment, the invention comprises a tribological coating comprising graphene oxide.

In one embodiment, the invention comprises a lubricating composition comprising a base lubricant and at least one carbon-containing additive that forms, under locally pyrolytic conditions, a tribologically-effective amount of graphene oxide In one embodiment, the invention comprises a lubricating composition comprising a base lubricant and at least one carbon-containing additive that forms, under locally pyrolytic conditions, a tribologically-effective amount of reduced graphene oxide.

In one embodiment, the invention comprises a method of synthesizing a plurality of surface-graphitized abrasive nanoparticles comprising refluxing a reaction mixture comprising at least one solvent, at least one metal oxide, and at least one compound promoting polycyclic aromatic hydrocarbon formation to form at least one surface-graphitized abrasive nanoparticle and thereafter collecting the surface-graphitized abrasive nanoparticles from the reaction mixture.

In one embodiment, the invention comprises methods of use of graphene in drug delivery formulations, medical imaging contrast formulations, metal prosthetic devices, polishing agents and metal prosthetic devices and steel devices polished by the polishing agent, detergent formulations, and macroscopic solid material comprising surface-graphitized abrasive nanoparticles.

In one embodiment, the invention comprises a nanoparticle comprising a core comprising at least one metal atom and a surface-graphitized shell around the core. In one embodiment, the surface-graphitized shell comprises a fullerene carbon shell.

In one embodiment, the invention comprises a microparticle agglomerate comprising at least one nanoparticle, wherein the nanoparticle comprises a core comprising at least one metal atom and a surface-graphitized shell around the core, and at least one graphitic carbon structure associated with the nanoparticle. In one embodiment, the surface-graphitized shell comprises a fullerene carbon shell and the graphitic structure comprises graphene and/or its derivatives.

In one embodiment, the invention comprises a lubricating composition comprising a base lubricant and a tribologically-effective amount a plurality of nanoparticles comprising a core comprising at least one metal atom and a surface-graphitized shell around the core. In one embodiment, the surface-graphitized shell comprises a fullerene carbon shell.

In one embodiment, the invention comprises an additive formulation for addition to a base lubricant, the additive formulation comprising a base solvent and an effective amount of at least one carbon-containing additive whereupon the carbon-containing additive forms, upon local pyrolysis, a tribologically-effective amount of at least one graphitic carbon-containing structure.

In one embodiment, the invention comprises a coating applied to a surface of a material, the coating comprising at least one nanoparticle comprising a core comprising at least one metal atom and a surface-graphitized shell around the core. In one embodiment, the surface-graphitized shell comprises a fullerene carbon shell.

In one embodiment, the invention comprises a composite material comprising a matrix material and at least one nanoparticle dispersed in the matrix material, the nanoparticle comprising a core comprising at least one metal atom and a surface-graphitized shell around the core. In one embodiment, the surface-graphitized shell comprises a fullerene carbon shell.

In one embodiment, the invention comprises a composite material comprising a material coated with a solution comprising graphene, wherein the solution comprising graphene is made by a process comprising refluxing a reaction mixture comprising at least one solvent and at least one compound promoting polycyclic aromatic hydrocarbon formation under conditions to prevent the complete combustion of the carbon source into carbon dioxide or carbon monoxide, and thereafter applying the reaction mixture to the surface of a composite material.

In one embodiment, the invention comprises a composite material comprising fibers coated with a solution comprising graphene, wherein the solution comprising graphene is made by a process comprising refluxing a reaction mixture comprising at least one solvent and at least one compound promoting polycyclic aromatic hydrocarbon formation under conditions to prevent the complete combustion of the carbon source into carbon dioxide or carbon monoxide, and thereafter applying the reaction mixture to the surface of the fibers that comprise a composite material.

In one embodiment, the invention comprises a composite material comprising a fiber mesh coated with a solution comprising graphene, wherein the solution comprising graphene is made by a process comprising refluxing a reaction mixture comprising at least one solvent and at least one compound promoting polycyclic aromatic hydrocarbon formation under conditions to prevent the complete combustion of the carbon source into carbon dioxide or carbon monoxide, and thereafter applying the reaction mixture to the surface of the a fiber mesh that comprises a composite material.

In one embodiment, the invention comprises a concrete mix mixed with a solution comprising graphene and its derivatives, wherein the solution comprising graphene and its derivatives is made by a process comprising refluxing a reaction mixture comprising at least one solvent and at least one compound promoting polycyclic aromatic hydrocarbon formation under conditions to prevent the complete combustion of the carbon source into carbon dioxide or carbon monoxide, and thereafter mixing the reaction mixture with the concrete mix.

In one embodiment, the invention comprises an asphalt mix mixed with a solution comprising graphene and its derivatives, wherein the solution comprising graphene and its derivatives is made by a process comprising refluxing a reaction mixture comprising at least one solvent and at least one compound promoting polycyclic aromatic hydrocarbon formation under conditions to prevent the complete combustion of the carbon source into carbon dioxide or carbon monoxide, and thereafter mixing the reaction mixture with the asphalt mix.

In one embodiment, the invention comprises fiberglass coated with a solution comprising graphene and its derivatives, wherein the solution comprising graphene and its derivatives is made by a process comprising refluxing a reaction mixture comprising at least one solvent and at least one compound promoting polycyclic aromatic hydrocarbon formation under conditions to prevent the complete combustion of the carbon source into carbon dioxide or carbon monoxide, and thereafter applying the reaction mixture to the surface of the fiberglass.

In one embodiment, the invention comprises plastic coated with a solution comprising graphene and its derivatives, wherein the solution comprising graphene and its derivatives is made by a process comprising refluxing a reaction mixture comprising at least one solvent and at least one compound promoting polycyclic aromatic hydrocarbon formation under conditions to prevent the complete combustion of the carbon source into carbon dioxide or carbon monoxide, and thereafter applying the reaction mixture to the surface of the plastic.

In one embodiment, the invention comprises a mix of polymers configured to prepare a plastic mixed with a solution comprising graphene and its derivatives, wherein the solution comprising graphene and its derivatives is made by a process comprising refluxing a reaction mixture comprising at least one solvent and at least one compound promoting polycyclic aromatic hydrocarbon formation under conditions to prevent the complete combustion of the carbon source into carbon dioxide or carbon monoxide, and thereafter mixing the reaction mixture with a mix of polymers configured to prepare a plastic.

In one embodiment, the invention comprises graphite coated with a solution comprising graphene and its derivatives, wherein the solution comprising graphene and its derivatives is made by a process comprising refluxing a reaction mixture comprising at least one solvent and at least one compound promoting polycyclic aromatic hydrocarbon formation under conditions to prevent the complete combustion of the carbon source into carbon dioxide or carbon monoxide, and thereafter coating the graphite with the reaction mixture.

In one embodiment, the invention comprises wire or cable coated with a solution comprising graphene and its derivatives, wherein the solution comprising graphene and its derivatives is made by a process comprising refluxing a reaction mixture comprising at least one solvent and at least one compound promoting polycyclic aromatic hydrocarbon formation under conditions to prevent the complete combustion of the carbon source into carbon dioxide or carbon monoxide, and thereafter coating the wire or cable with the reaction mixture.

In one embodiment, the invention comprises a method of synthesizing nano-steel comprising refluxing a reaction mixture comprising at least one solvent, at least one metal oxide, and at least one compound promoting polycyclic aromatic hydrocarbon formation to form at least one surface-graphitized abrasive nanoparticle, thereafter collecting a vapor stream produced by the reflux of the reaction mixture containing the surface-graphitized abrasive nanoparticle and subjecting the collected vapor stream to an annealing treatment.

In one embodiment, the invention comprises a method of graphene collection comprising refluxing a reaction mixture comprising at least one solvent and at least one compound promoting polycyclic aromatic hydrocarbon formation and thereafter collecting a vapor stream produced by the reflux of the reaction mixture.

In one embodiment, the invention comprises a method of collection of derivative of graphene comprising refluxing a reaction mixture comprising at least one solvent and at least one compound promoting polycyclic aromatic hydrocarbon formation and thereafter collecting a vapor stream produced by the reflux of the reaction mixture.

In one embodiment, the invention comprises a collection assembly configured to collect the vapor produced by refluxing a reaction mixture comprising at least one solvent and at least one compound promoting polycyclic aromatic hydrocarbon formation.

In one embodiment, the invention comprises a hydrophobic self-assembly configured to self-assemble graphene and its derivatives from the vapor produced by refluxing a reaction mixture comprising at least one solvent and at least one compound promoting polycyclic aromatic hydrocarbon formation.

In one embodiment, the invention comprises a method of hydrophobic self-assembly of graphene comprising refluxing a reaction mixture comprising at least one solvent and at least one carbonaceous material promoting polycyclic aromatic hydrocarbon formation under conditions that inhibit complete combustion of the carbonaceous material, thereafter collecting vapors produced by the reflux of the reaction mixture, directing the vapors to an aqueous substrate, whereupon graphene is deposited on the surface of the aqueous substrate; and recovering graphene from the surface of the aqueous substrate.

In one embodiment, the invention comprises a method of production of graphene comprising refluxing a reaction mixture comprising at least one solvent and at least one carbonaceous material promoting polycyclic aromatic hydrocarbon formation under conditions that inhibit complete combustion of the carbonaceous material, thereafter collecting vapors produced by the reflux of the reaction mixture, directing the vapors to a substrate, whereupon graphene is deposited on the surface of the substrate, and recovering graphene from the surface of the substrate.

In one embodiment, the invention comprises a method of lubrication of a mechanical system comprising operating the mechanical system with a lubricating composition comprising an effective amount of at least one carbon-containing additive that promotes the in situ chemical formation of a tribologically-effective amount of at least one tribologically-useful graphitic carbon-containing structure during operation of the mechanical system.

In one embodiment, the invention comprises a method of increasing the efficiency of an engine comprising operating the engine with a lubricating composition comprising an effective amount of at least one carbon-containing additive that promotes the in situ chemical formation of a tribologically-effective amount of at least one tribologically-useful graphitic carbon-containing structure during operation of the mechanical system.

In one embodiment, the invention comprises a method of decreasing the negative horsepower of an engine comprising operating the engine with a lubricating composition comprising an effective amount of at least one carbon-containing additive that promotes the in situ chemical formation of a tribologically-effective amount of at least one tribologically-useful graphitic carbon-containing structure during operation of the mechanical system.

In one embodiment, the invention comprises a method of decreasing the torque of an engine comprising operating the engine with a lubricating composition comprising an effective amount of at least one carbon-containing additive that promotes the in situ chemical formation of a tribologically-effective amount of at least one tribologically-useful graphitic carbon-containing structure during operation of the mechanical system.

In one embodiment, the invention comprises a method of production of a tribological resin, film, coating or lacquer comprising refluxing a reaction mixture comprising at least one solvent and at least one carbonaceous material promoting polycyclic aromatic hydrocarbon formation under conditions that inhibit complete combustion of the carbonaceous material, thereafter mixing the reaction mixture with a resin, film, coating or lacquer prior to application or setting of the resin, film, coating or lacquer.

In one embodiment, the invention comprises a dynamic furnace configured for the production of surface-graphitized abrasive nanoparticles comprising refluxing a reaction mixture comprising at least one solvent, at least one metal oxide, and at least one compound promoting polycyclic aromatic hydrocarbon formation to form at least one surface-graphitized abrasive nanoparticle, thereafter collecting a vapor stream produced by the reflux of the reaction mixture containing the surface-graphitized abrasive nanoparticle and subjecting the collected vapor stream to a high shear environment comprising high speed rotation, high frequency oscillation or vibration, hydrodynamic squeezing, frictional impact with one or more moving parts, high speed stirring, or any combination thereof, and thereafter collecting the surface-graphitized abrasive nanoparticles. In one embodiment, the dynamic furnace further comprises a surface topography comprising fins, rods, bumps, depressions, holes, asperities, tunnels and any combination thereof.

BRIEF DESCRIPTION OF THE DRAWINGS

The invention will be described with reference to the accompanying drawings, in which like elements are referenced with like numerals.

DETAILED DESCRIPTION OF THE INVENTION

Figure 1A:
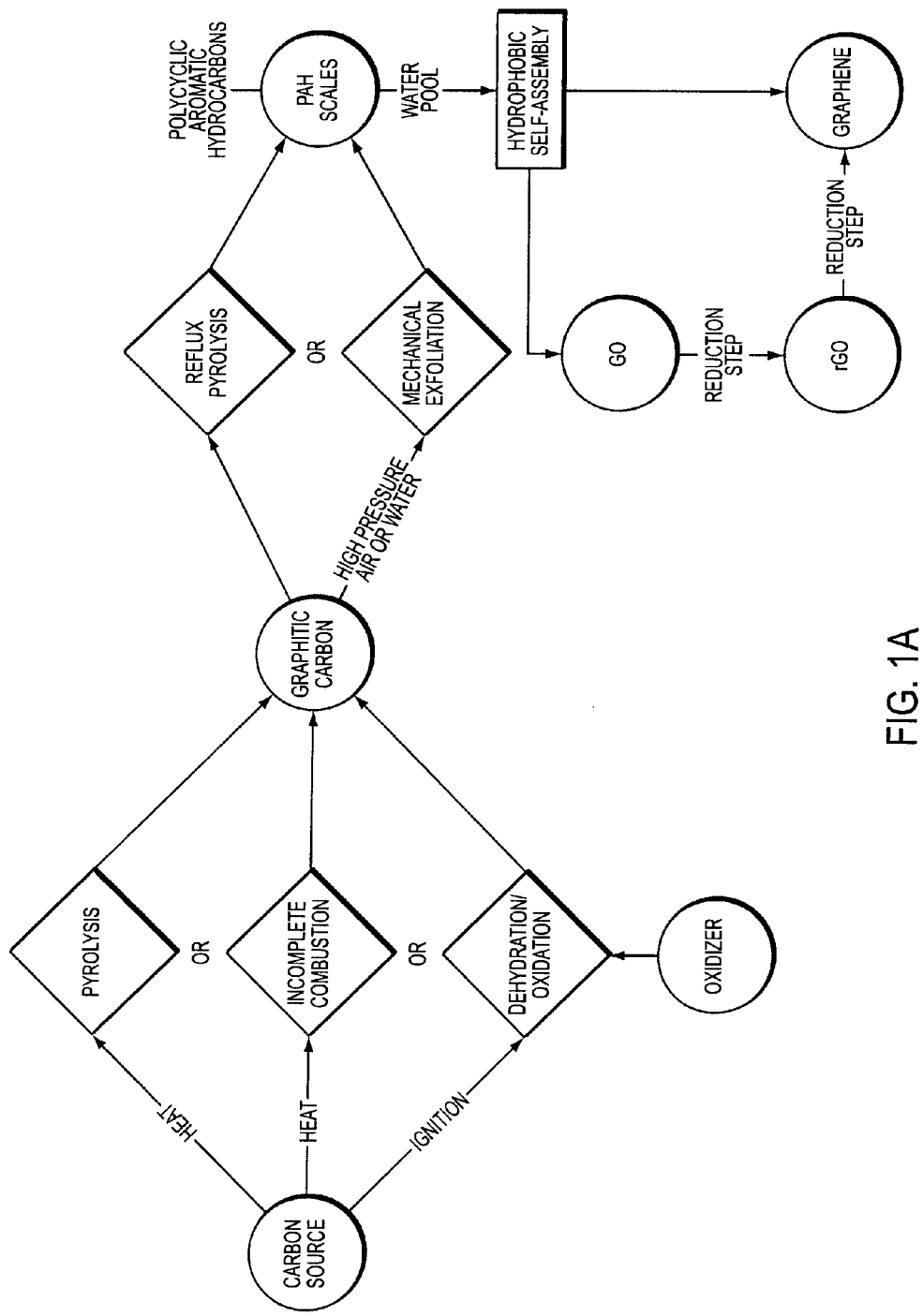
FIGS. 1A and 1B show schematic representations respectively of the graphene/GO and SGAN preparation steps in an embodiment of the invention.
Figure 1B:
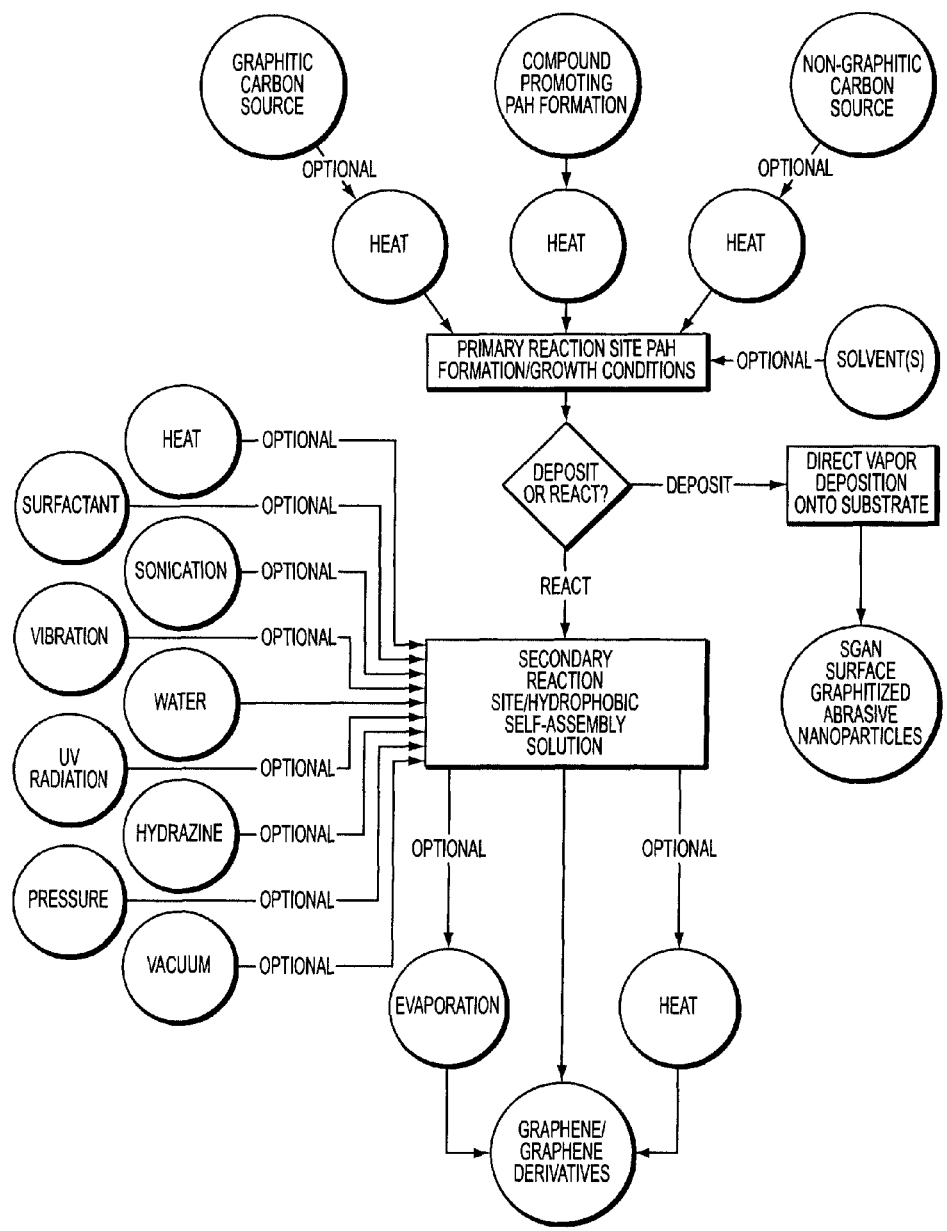

The invention relates to methods for the facile synthesis of graphene, graphene derivatives and nanoparticles, and their use as tribologically-beneficial lubricant additives. The products of the methods of the invention have numerous applications, including but not limited to molecular level coatings for composite reinforcement, heat shielding, ballistic transistors, integrated circuits, reinforced fibers and cables, and nano-polishing agents.

Cyclic, as used herein, refers to any molecule with at least one five-membered, or larger, ring, where at least half of the atoms forming the ring are carbon atoms. The ring may be aromatic or non-aromatic.

Tribologically-effective, as used herein, refers to any amount of additive or amounts of multiple additives to a lubricated system sufficient to be tribologically beneficial to such lubricated system.

Tribologically beneficial, as used herein, refers to any additive that reduces friction in a mechanical system in which it is formed, found or employed.

Tribological agent, as used herein, refers to a molecule that measurably reduces friction in a mechanical system in which it is formed, found, or employed.

Bucky-diamond or nano-Bucky-diamond, as used herein, refers to any nanoparticle having a nano-diamond core that may comprise non-carbon hetero-atoms, and a fullerenic carbon shell formed around the core.

Surface-graphitized abrasive nanoparticle (SGAN), as used herein, refers to any nanosized particle comprising at least one non-carbon hetero-atom enveloped by an outer shell comprising substantially carbon.

Spheroid, as used herein, refers to a particle that is shaped substantially like a sphere but is not necessarily perfectly round.

A matrix material, as used herein, refers to any material forming a continuous phase in a composite of two or more materials.

A spinel structure, as used herein, refers to any cubic mineral crystal of the general formula $A^{2+}B_2^{3+}O_4^{2-}$ with the oxide anions (O) arranged in a cubic close-packed lattice, the A cations occupying all of the tetrahedral sites, and the B cations occupying all of the octahedral sites in the lattice.

An inverse spinel structure, as used herein, refers to any cubic mineral crystal of the general formula $A^{2+}B_2^{3+}O_4^{2-}$ with the oxide anions arranged in a cubic close-packed lattice, the A cations occupying half of the octahedral sites, and the B cations occupying half of the octahedral and all of the tetrahedral sites in the lattice.

Graphitic carbon, as used herein, refers to any structure having a carbon lattice matrix, including, but not limited to, graphite, graphene, graphene oxide, fullerene, fullerene-like structure, endo-fullerene, nano-onion, nano-peapod, nano-tube, nanobud, reduced graphene oxide, lacy carbon, and polycyclic aromatic compounds.

Carbon lattice matrix, as used herein, refers to, any 2-dimensional polycyclic carbon structure formed of $sp^2$- or $sp^3$-hybridized carbon atoms.

Dynamic furnace, as used herein, refers to a heated nanoparticle synthesis furnace apparatus that employs an agitative, sonic, centrifugal, centripetal, compressive or shearing force, or a combination of these forces, during the synthesis stage of the nanoparticle product formation.

Ex Situ Method for Synthesis of Graphene, Graphene Oxide, Reduced Graphene Oxide and Other Graphene Derivative Structures and Nanoparticles.

In one aspect, the invention relates to an ex situ method for synthesis of graphene, graphene oxide, reduced graphene oxide, and other graphene derivative structures and nanoparticles. An economical dehydration reaction or reflux pyrolysis can be used to form graphitic carbon from a carbonaceous material carbon source. The methods disclosed are industrially-scalable for industrial production. The carbon source is preferably a sugar containing a 6-membered ring structure, although many other carbonaceous materials may be subjected to dehydration, pyrolysis, or oxidation and used. The carbon source is subjected to reflux pyrolysis, oxidation/reduction, or acid dehydration to form a graphitic carbon reactant starting material. In other embodiments, the dehydration/oxidation/pyrolysis synthesis step to produce suitable graphitic carbon is bypassed and graphitic carbon itself is used as the reactant starting material. The graphitic carbon can be subjected to refluxing with a liquid solvent, and graphene/graphene oxide (GO) can be emitted as nanoscopic scales or "nanoscales" suspended in vapor/steam. Alternatively or additionally, a graphitic carbon source may be subjected to a highly-pressurized liquid or vapor to produce graphene scales without pyrolysis, dehydration, or oxidation step. The resulting graphene/GO scales travel in the vapor and are collected either by direct deposition onto a solid substrate in physical contact with the emitted vapor, or by applying the particle-containing vapor to an aqueous solution or liquid used to promote "hydrophobic self-assembly" of the scales into larger graphene/GO sheets.

In one embodiment, the reaction environment is controlled to limit the amount of ambient oxygen ($O_2$) in the chamber, thereby discouraging combustion of the reactants during heating. In one embodiment, the reaction is carried out without the use of an added solvent. In one embodiment, the produced GO is converted to reduced graphene oxide (rGO) or graphene sheets suspended in a heated or unheated liquid collection medium. The resulting large hydrophobically self-assembling sheets are easily reduced to rGO or graphene, which may be used in industry to produce a range of useful products, including, but not limited to, protective coatings, and low weight/high strength graphene-reinforced composites, wires, and fibers.

Turning to the figures, FIG. 1A depicts a schematic representation of the graphene/GO preparation steps in an embodiment of the invention in which a reaction mixture, including an essentially non-graphitic carbonaceous material carbon source, is reacted to form graphitic carbon by pyrolysis, dehydration, an oxidation/reduction reaction, or incomplete combustion. In one embodiment, a graphitic carbon starting material is used, eliminating the need for a pyrolysis or dehydration reaction step.

In one embodiment, the reaction mixture is refluxed to form a vapor stream. Graphene/graphene oxide (GO) nanoscales are carried away in the resulting vapor stream emitted during heating of the slurry or solution. The graphene/GO scales are collected, preferably by bubbling the vapor through a liquid that traps and suspends the scales. Alternatively graphene/GO scales form on the surface of the liquid when the vapor stream is directed to the surface. In a process referred to herein as "hydrophobic self-assembly," individual graphene/GO scales join to form sheets of graphene/GO layers at the surface of the liquid.

In one embodiment, the carbon source is heated directly by an external heating source in a pyrolysis or dehydration reaction to form graphitic carbon and water. In one embodiment, the carbon source is sucrose. In one embodiment, the resulting formed water serves as a solvent to permit refluxing of the reaction products. In one embodiment, the reaction to form graphitic carbon proceeds as essentially represented in Equation 1:

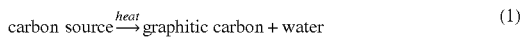

(1)

In one embodiment, the carbon source is exposed to an acid in a pyrolysis or dehydration reaction to form graphitic carbon and water. In one embodiment, the carbon source is sucrose and the acid is concentrated sulfuric acid. In one embodiment, the resulting formed water serves as a solvent to permit refluxing of the reaction products. In one embodiment, the reaction product is a graphitic foam. In one embodiment, the reaction product is a graphitic slurry. In one embodiment, the reaction to form graphene proceeds as essentially represented in Equation 2:

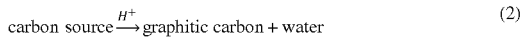

(2)

In one embodiment, the carbon source is reacted with an oxidizer to form graphitic carbon in the form of a graphene oxide. In one embodiment, the reaction to form GO proceeds as essentially represented in Equation 3:

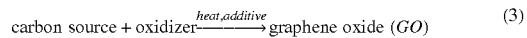

where the applied heat drives the reaction and the optional additive serves to catalyze the reaction and/or improve the yield of the desired reaction product.

A GO reaction product is schematically shown as Molecule (1) below:

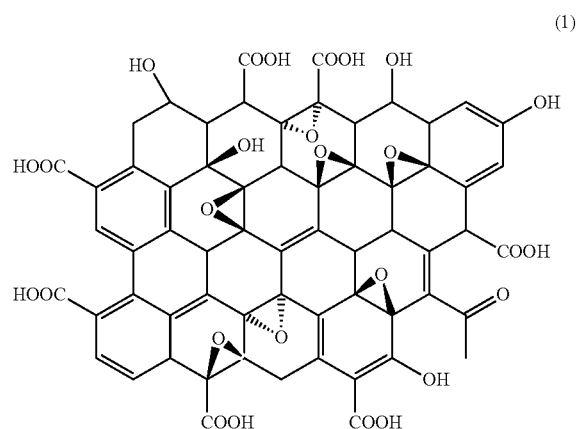

In the above embodiments, the reaction conditions are selected such that the reaction does not lead to complete combustion of the carbon source into carbon dioxide or an incomplete combustion to form carbon monoxide. The reaction conditions are rather designed, preferably by control of the reaction atmosphere, to form graphitic carbon-carbon bonds. In some embodiments, a portion of the carbon source is purposefully combusted to provide the heat required for conversion of another portion of the carbon source to form the desired graphitic bonds. In some embodiments, the reaction occurs under non-ideal combustion conditions, such as pyrolysis or smoldering.

Pyrolysis, as used herein, refers to the decomposition of a carbon source at an elevated temperature with low oxygen or other oxidizer levels.

Smoldering, as used herein, refers to a slow, low-temperature, flameless reaction sustained by the heat from oxygen directly reacting with the surface of a solid or liquid fuel.

Scales or nanoscales, as used herein, refer to discrete sections of graphene or graphene derivative.

Efforts to improve combustion efficiency have obscured the true value of compounds previously thought of as useless waste, such as the carbonaceous "phlegm" of early coal furnaces (see, for example, *Coal-Tar and Ammonia*, 5$^{th}$ ed., by Lunge, D. Van Nostrand Co., New York, 1916), that actually contains graphitic material, including graphene. Likewise, modern combustion advances have overlooked the value of many old processes, now deemed outmoded, that are actually capable of adaptation to purposeful maximization of soot particulates formation ultimately into graphene, a graphene derivative, a carbon-encapsulated metallic nanoparticle, or nano-steel.

Although the formation of PAHs in carbonaceous particulates "soot" as a product of incomplete combustion is known, the usefulness of such PAHs has heretofore been minimal due to their limited size and tendency, as reported in the current art, to typically drift away from the synthesis conditions necessary for continued growth. Wiersum et al. ("The Formation of Polyaromatic Hydrocarbons, Fullerenes and Soot in Combustion: Pyrolytic Mechanisms and the Industrial and Environmental Connection", pp. 143-194 in *Gas Phase Reactions in Organic Synthesis*, ed. by Vallée, Gordon and Breach Science Publishers, Amsterdam, 1997) report a number of different gas phase reactions to form PAHs. None of the known gas-phase PAH synthesis methods to date produce graphene or any form of planar graphitic carbon greater than 222 carbon atoms in size.

In one embodiment, the methods and processes disclosed herein promote PAH production through extended exposure to favorable synthesis conditions by collecting and trapping product vapors of the reaction mixture, permitting resulting PAHs to grow to sizes exhibiting the general properties of graphene. Other embodiments, methods, and processes disclosed herein are designed to specifically promote continued PAH growth conditions by their self-assembly in steam-rich or aqueous solution conditions into large graphene sheets. These processes permitting graphene synthesis, either from compounds promoting PAH formation alone or from compounds promoting PAH formation and carbonaceous or graphitic reactant materials, are scalable to meet industrial production volumes.

In one embodiment, one or more compounds that promote the formation or growth of PAHs are used in the production of graphene, graphene derivatives, carbon-encapsulated metallic nanoparticles, or nano-steel. These compounds may include, but are not limited to, chemicals that are known intermediates in PAH formation and chemicals that form intermediates of PAH formation.

In one embodiment, the initial reactions occur in a solvent system under reflux conditions to promote the synthesis of PAH units that later self-assemble into larger graphene sheets. In some embodiments, the reflux conditions are azeotropic reflux conditions (see, for example, Udeye et al., "Ethanol heterogeneous azeotropic distillation design and construction", *Internat. J. of Phys. Sci.*, Vol. 4, pp. 101-106, 2009; Sun et al., "ZrOCl$_2$.8H$_2$O: An Efficient, Cheap and Reusable Catalyst for the Esterification of Acrylic Acid and Other Carboxylic Acids with Equimolar Amounts of Alcohols", *Molecules*, Vol. 11, pp. 263-271, 2006). In some reflux conditions, a promoter is added. In some embodiments, the promoter is a form of graphitic carbon. In some embodiments, the promoter is biochar, coal phlegm, nano-coal, an activated form of nano-coal, activated charcoal, graphite particles, soot particulate matter, or another sequestered carbonaceous waste form.

A sequestered carbonaceous waste, as used herein, is any carbonaceous waste product of synthesis, pyrolysis, or incomplete combustion, which is typically collected and isolated to prevent conversion into or release as an atmospheric greenhouse gas. In one embodiment, a sequestered carbonaceous waste can be utilized as a carbon source in the reaction mixture, in which instance the added carbon promotes the reaction, in part, by serving as a thermal conductivity-enhancing heat transfer agent (see, for example, Baby et al., "Enhanced Convective Heat Transfer Using Graphene Dispersed Nanofluids", *Nanoscale Research Letters*, Vol. 6, no. 289, 2011).

The sequestered carbonaceous waste may be collected from the emissions of any process, including but not limited to the emissions of a diesel truck or the emissions of a coal-fired power plant. In some embodiments, a diesel particulate filter is used to collect the carbonaceous waste as part of a "diesel emission control strategy." In other embodiments, a scrubber is used to collect the carbonaceous waste. The California Air Resources Board (CARB) recently enacted legislation requiring reduced particulate and noxious gas emissions, including from diesel trucks and buses, achieved by the addition of a filter to the exhaust systems of trucks (see *California Code of Regulations*, Title 13, Div. 3, Ch. 14 et seq.).

In some embodiments, designed as an alternative to so-called "regenerative" technologies that combust collected soot and continue to release greenhouse gasses to the environment, a reusable filter is employed. When it is time for a truck driver or other user to replace a dirty particulate filter, instead of disposing of the dirty filter and buying a new filter, the user exchanges the contaminated filter for a clean one. The sequestered carbonaceous waste contained in the used filter is preferably removed from the particulate filter or scrubber and used as a carbon source for graphene or graphene derivative synthesis. The filter or scrubber is preferably reused to collect additional carbonaceous waste from emissions as the process is repeated, as the process seeks to incorporate a large portion of the carbon sequestered into the graphene product rather than into greenhouse gas emissions. In some embodiments, the sequestered carbonaceous waste is harvested from the particulate filter or scrubber by being dissolved in an organic solvent. In other embodiments, the sequestered carbonaceous waste is harvested using water, an aqueous mixture, or steam.

PAH-promoting compounds for use in processes include, but are not limited to, dimethyl ether, propyne, propadiene, alcohols, including, but not limited to, propargyl alcohol and isopropanol, acetylene, and compounds that promote $C_1$ to $C_5$ hydrocarbon radical formation.

Methyl radicals ($CH_3$.) are known to promote the growth of both PAHs (see Shukla et al., "Role of Methyl Radicals in the Growth of PAHs", *J. Am. Soc. Mass Spectrom.*, Vol. 21, pp. 534-544, 2010) and graphene (see Wellmann et al., "Growth of graphene layers on HOPG via exposure to methyl radicals", *Surface Science*, Vol. 542, pp. 81-93, 2003).

Dimethyl ether forms methyl radicals and promotes PAH formation under gaseous combustion conditions in the presence of another carbon source (see Yoon et al., "Synergistic effect of mixing dimethyl ether with methane, ethane, propane, and ethylene fuels on polycyclic aromatic hydrocarbon and soot formation", *Combustion and Flame*, Vol. 154, pp. 368-377, 2008). Other hydrocarbon radicals, including, but not limited to, $C_2H$., $C_2H_3$., $C_3H_3$., $C_4H_3$., $C_4H_5$., and $C_5H_3$., are also capable of nucleating and growing PAHs (see Pope et al., "Exploring Old and New Benzene Formation Pathways in Low-Pressure Premixed Flames of Aliphatic Fuels", *Proceedings of the Combustion Institute*, Vol. 28, pp. 1519-1527, 2000).

The propargyl radical ($C_3H_3$') has been proposed as a key intermediary for PAH formation in a number of kinetic studies (see McEnally et al., "Computational and Experimental Study of Soot Formation in a Coflow, Laminar Ethylene Diffusion Flame", 27$^{th}$ *Symposium (International) on Combustion*, pp. 1497-1505, 1998; Shafir et al., Kinetics and Products of the Self-Reaction of Propargyl Radicals", *J. Phys. Chem. A*, Vol. 107, pp. 8893-8903, 2003; Tang et al., "An Optimized Semidetailed Submechanism of Benzene formation from Propargyl Recombination", *J. Phys. Chem. A*, Vol. 110, pp. 2165-2175, 2006).

Propyne and propadiene also promote PAH formation (see Gazi et al., "A Modelling Study of Allene and Propyne Combustion in Flames", *Proceedings of the European Combustion Meeting*, 2011). Acetylene also may play a role in PAH nucleation and growth (see Frenlach et al., "Aromatics Growth beyond the First Ring and the Nucleation of Soot Particles", *Preprints of the 202nd ACS National Meeting*, Vol. 36, pp. 1509-1516, 1991).

Figure 2A:
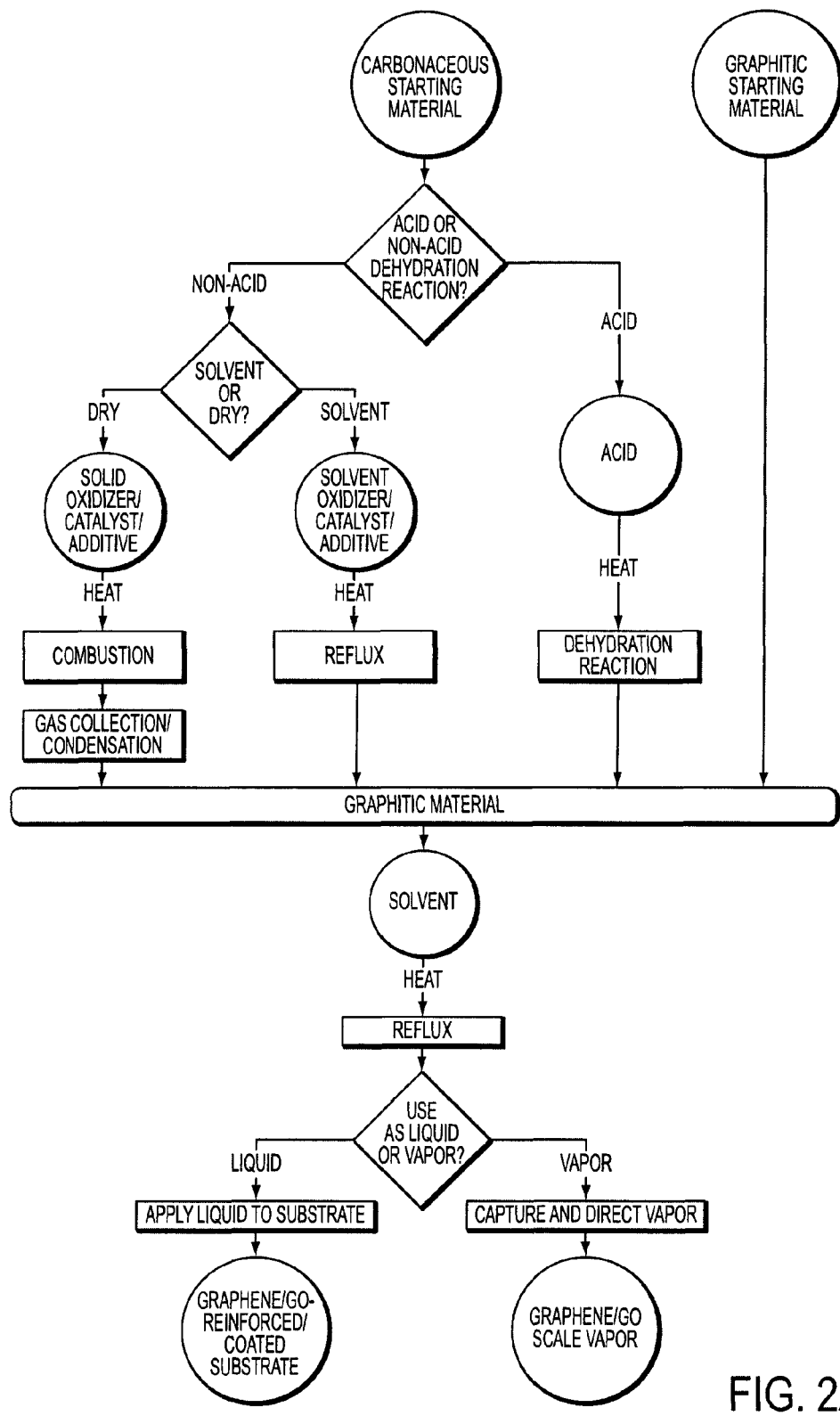
FIG. 2A shows a process flow chart for the formation of a graphene/GO-reinforced/coated substrate or graphene/GO scale vapor from a carbonaceous or graphitic starting material in an embodiment of the invention.
Figure 2B:
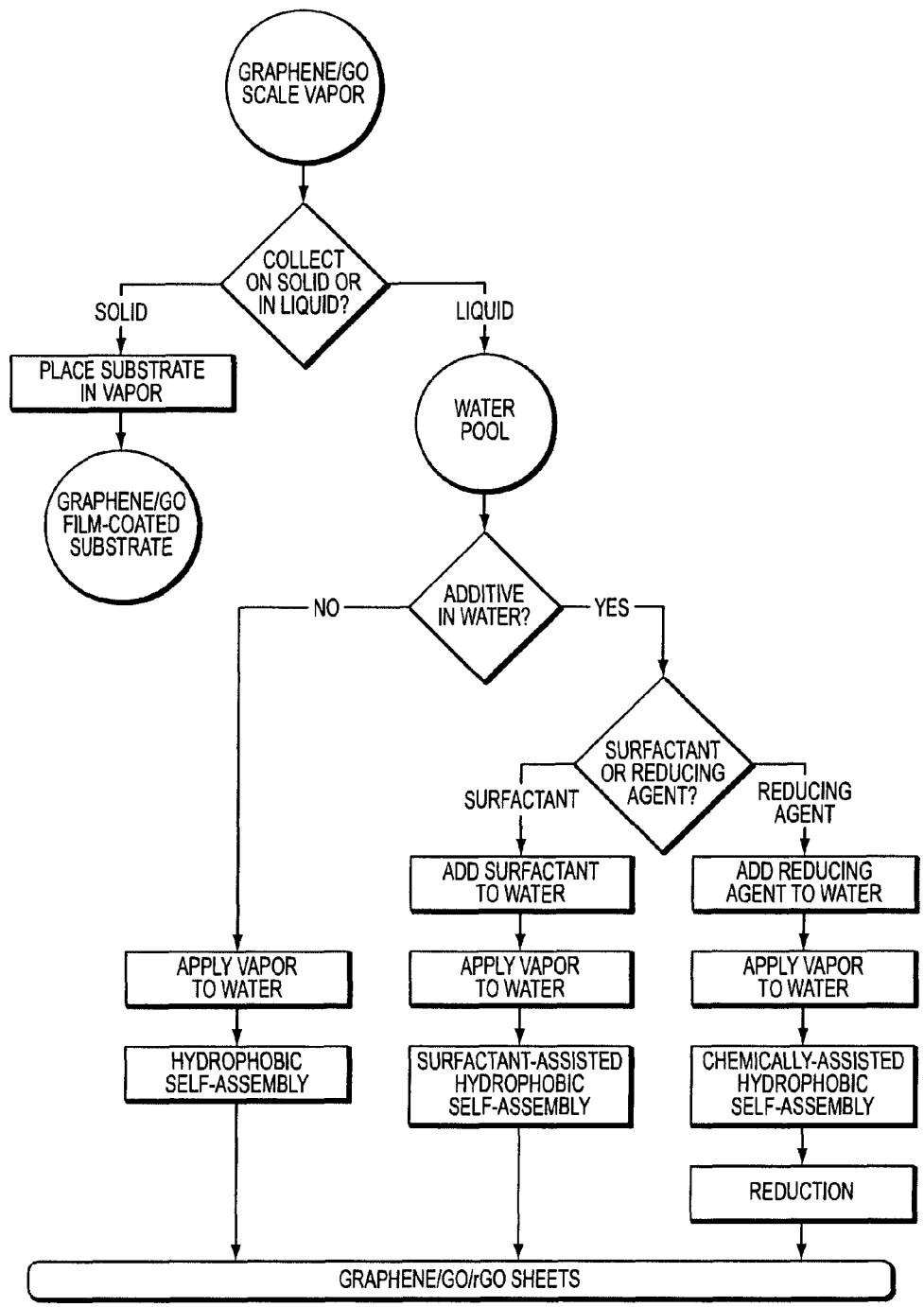
FIG. 2B shows a process flow chart for the formation of a graphene/GO film-coated substrate or a graphene/GO/rGO sheet from a graphene/GO scale vapor in an embodiment of the invention.

FIGS. 2A and 2B show process flow charts for forming various graphene products from either a non-graphitic carbonaceous starting material or a graphitic starting material.

Referring to FIG. 2A, when starting with a non-graphitic carbonaceous starting material, the carbonaceous material may be converted to a graphitic material by several different pathways.

In one embodiment, the carbonaceous material is combined with an acid and converted by a dehydration reaction, either with or without the addition of heat and refluxing of the reagents. In one embodiment, the carbonaceous material is a sugar. In some embodiments, the sugar is sucrose. In one embodiment, the acid is concentrated sulfuric acid.

In one embodiment, the carbonaceous material is heated without a solvent. The carbonaceous material may be heated with or without an additive, which may be an oxidizer, a metal oxide, or a catalyst, optionally followed by collection and condensation of any produced gas or vapor, to form the graphitic material. The use of an oxidizer or metal oxide promotes the formation of GO over graphene, whereas in the absence of an oxidizer or metal oxide, graphene forms preferentially over GO. In one embodiment, the carbonaceous material is preferably heated to a high temperature, such as by a direct or an indirect flame. In one embodiment, the additive is a metal-containing compound. In one embodiment, the metal is iron. In some embodiments, the additive is a metal oxide. In one embodiment, the additive is ferric oxide. In other embodiments, the additive is ferrocene.

In one embodiment, the carbonaceous material is heated in a refluxing solvent to form the graphitic material. The carbonaceous material may be combined with an additive, which may be an oxidizer, a metal oxide, or a catalyst. The use of an oxidizer or metal oxide promotes the formation of GO over graphene, whereas in the absence of an oxidizer or metal oxide, graphene forms preferentially over GO. In one embodiment, the additive is a metal-containing catalytic compound. In some embodiments, the metal is iron. In one embodiment, the additive is a metal oxide. In one embodiment, the metal oxide is ferric oxide. In some embodiments, the additive is ferrocene. In some embodiments, the solvent includes one or more of an alcohol, water, and a mineral oil. The solvent preferably permits a high-temperature refluxing of the reaction mixture. The solvent also preferably helps to dissolve the reactants, to prevent combustion of the reactants, and to promote vapor production for collection of the product. In some embodiments, the use of a solvent improves the reaction yield and increases the interaction between reagents to promote the formation of the graphene or GO products.

In one embodiment, when the carbonaceous material is combined with a metal oxide in the reaction mixture, surface-graphitized abrasive nanoparticles (SGANs), including SGAN spheroids, are formed. The SGANs can be recovered for any use, such as a nano-polishing agent or as an additive to a lubricant. It is contemplated that recovery of the SGANs from the reaction mixture can be accomplished by use of a magnet or externally applied magnetic field. Recovery may also be accomplished by centrifugation. In one embodiment, the reaction mixture comprising the SGANs can be used as an additive to a lubricant.

In one embodiment, a large-scale DC arc-discharge apparatus, a chamber, or a cylinder can be used to promote SGAN formation. In some embodiments, the ferric oxide is provided to the system as a powder to promote SGAN formation. In one embodiment, the ferric oxide comprises a nanopowder. In one embodiment, a high carbon content vapor can be supplied to the system.

In one embodiment, the SGANs can be produced in a high shear environment in a "dynamic furnace". The high shear environment of the "dynamic furnace" may be provided by any method or combination of methods, including, but not limited to, rotating the tube furnace at high speeds, oscillating or vibrating the furnace at high frequencies, employing sonication, hydrodynamic squeezing, frictional impact with one or more moving parts, and stirring the "dynamic furnace" contents at high speeds. In one embodiment, the speed of rotation of the "dynamic furnace" can be on the order of about 1,000 to 11,000 RPM. In one embodiment, the "dynamic furnace" additionally can include a surface topography, which may include, but is not limited to, fins, rods, bumps, depressions, holes, asperities, and tunnels, to provide additional shearing forces, thereby increasing the shearing of the reaction mixture. In one embodiment, reaction gases can be supplied to the "dynamic furnace" apparatus. In one embodiment, SGAN synthesis can occur at elevated temperatures, elevated pressures, or reduced pressures. Temperatures in the "dynamic furnace" can be on the order of ~200 to ~800° F.

In one embodiment, the "dynamic furnace" comprises an incorporated tube furnace for formation of SGANs. An insulating portion can surround two concentric rotatable cylinders. The cylinders can include through-holes that allow material to pass between the area outside an outer cylinder, the area between the two cylinders, and the area inside the inner cylinder. The cylinders can be coaxial and rotatable in opposite directions at high speeds to produce high shearing forces. The dynamic tube furnace can also include a feed line for liquid components and a preheater leading into the main chamber. A separate feed line for gaseous components can also be included. The main chamber may be a single chamber or a two-zone chamber.

The inner surface of the outer cylinder or the outer surface of the inner cylinder may include fins, paddles, rods, bumps, or similar structures to provide shearing to the system. In one embodiment, the tube furnace can be designed in the form of a Wankel engine to provide the frictional contact, sheering, and squeezing to promote SGAN formation. The "dynamic furnace" can include a housing, a rotor, an eccentric wheel, and an inner gear meshing with an outer gear. As the rotor travels around in the "dynamic furnace" housing, frictional contact, sheering, and squeezing of the fluid between the rotor and the housing can promote SGAN formation. In one embodiment, the surfaces of one or more of these structures are electrified or electrifiable. In one embodiment, the electrified surfaces can act as an electrified cathode in the integral tube furnace.

In one embodiment, the carbonaceous material is a non-graphitic carbon source, which may include, but is not limited to, a sugar, sucrose, a sugar amphiphile, a graphene-promoting amphiphile, a sugar substitute, a starch, cellulose, an olefin, an acetate, one or more non-graphitic hydrocarbons, an alkane, an alkene, an alkyne, a ketone, toluene, gasoline, diesel fuel, kerosene, coal, coal tar, coke, or any combination of these. In one embodiment, coal and diesel fuel are preferred carbon sources. In one embodiment the coal is a pulverized coal. In one embodiment the coal is a nano-coal, such as the nano-coal sold by Nano Fuels Technology, LLC (Reno, Nev., United States), having particle sizes in the sub-micron range.

A sugar amphiphile or a sugar-like amphiphile may be any molecule with a hydrophilic sugar portion and a hydrophobic portion, including, but not limited to those described by Fenimore ("Interfacial Self-assembly of Sugar-based Amphiphiles: Solid- and Liquid-core Capsules", University of Cincinnati Ph.D. thesis dated Oct. 16, 2009), Jadhav et al. ("Sugar-Derived Phase-Selective Molecular Gelators as Model Solidifiers for Oil Spills", *Angew. Chem. Int. Ed.*, Vol. 49, pp. 7695-7698, 2010), Jung et al. ("Self-Assembling Structures of Long-Chain Sugar-Based Amphiphiles Influenced by the Introduction of Double Bonds", *Chem. Eur. J.*, Vol. 11, pp. 5538-5544, 2005), Paleta et al. ("Novel amphiphilic fluoroalkylated derivatives of xylitol, D-glucose and D-galactose for medical applications: hemocompatibility and co-emulsifying properties", *Carbohydrate Research*, Vol. 337, pp. 2411-2418, 2002), Germaneau ("Amphiphilic Sugar Metal Carbenes: From Fischer Type to N-Heterocyclic Carbenes (NHCs)", Rheinische Friederich-Wilhems-Universität Bonn Ph.D. thesis, 2007), and Ye et al. ("Synthesis of Sugar-Containing Amphiphiles for Liquid and Supercritical Carbon Dioxide", *Ind. Eng. Chem. Res.*, Vol. 39, pp. 4564-4566, 2000).

A graphene-promoting amphiphile may be any molecule with a hydrophilic graphene-promoting portion and a hydrophobic portion, including, but not limited to those marketed by Dow Chemical Company (Midland, Mich., United States) under the trademarks TRITON™ or TERGITOL™, including, but not limited to, the TRITON X series of octylphenol ethoxylates and the TERGITOL NP series of nonylphenol ethoxylates.

Alternatively, a graphitic starting material may be used. The graphitic material may be any material including graphitic carbon, including, but not limited to, natural graphite, synthetic graphite, one or more polycyclic aromatic hydrocarbons (PAHs), graphene, activated carbon, biochar, coal phlegm, one or more benzenoids, naphthalene, or any combination of these.

Referring to FIG. 2A, the graphitic material in a solvent is heated. In some embodiments, the solvent includes one or more of an alcohol, water, and a mineral oil. In some embodiments, the mixture is heated to a boiling temperature. In some embodiments, the boiling solvent is refluxed.

In one embodiment, liquid graphene product resulting from reflux of the reaction mixture is collected in the reaction vessel itself. The graphene-containing liquid may be applied directly to a material or substrate to form a graphene-reinforced material, a graphene-coated substrate, a GO-reinforced material, or a GO-coated substrate.

Alternatively, the graphene-containing liquid may be further heated to form a vapor containing graphene/graphene derivative scales. A graphene/graphene derivative scale, as used herein, is understood to be one to several layers of graphene or graphene oxide carried in the vapor stream of the refluxing solvent or solvent mixture. The layers in the scale may be mostly planar or they may be crinkled or folded in the vapor stream. The length and width dimensions of the layers are preferably significantly larger than the thickness of the layers.

Referring to FIG. 2B, the graphene/graphene derivative scale-containing vapor may either be applied to a solid or a liquid.

The graphene/graphene derivative scales may be applied to a solid substrate by placing the solid substrate in the vapor stream or by applying the vapor stream to the solid substrate to form a graphene/graphene derivative film coated substrate. Any crinkling or folding in the scale layers is preferably reduced upon deposition on the solid substrate. In some embodiments, the deposited scales are annealed after deposition to improve their uniformity. In some embodiments, the deposited scales are annealed by heating of the substrate. In some embodiments, reactive end groups on neighboring deposited scales react with each other to form larger graphene/graphene derivative sheets. In some embodiments, a reducing agent is used to convert GO to rGO in the layers.

Alternatively, the graphene/graphene derivative scale-containing vapor may be applied to an aqueous pool. The vapor may be applied to the surface of the aqueous pool from above or by bubbling through the aqueous pool.

In one embodiment, the aqueous pool is a water pool with no additives. If the water pool contains no additives, the graphene/graphene derivative scales hydrophobically self-assemble to graphene/graphene derivative sheets at the water surface. In one embodiment, the deposited scales are annealed at the water surface to improve their uniformity. In one embodiment, reactive end groups on neighboring scales react with each other to form larger graphene/graphene derivative sheets at the water surface. In some embodiments, a reducing agent is used to convert GO to rGO in the assembling or assembled layers.

The aqueous pool may include one or more surfactants as an additive to aid in the hydrophobic self-assembly of the graphene/graphene derivative scales to the graphene/graphene derivative sheets at the water surface. Any crinkling or folding in the scale layers is preferably reduced either by interaction with the surfactant or upon arrival at the water surface. In one embodiment, the deposited scales are annealed at the water surface to improve their uniformity. In one embodiment, reactive end groups on neighboring scales react with each other to form larger graphene/graphene derivative sheets at the water surface.

The aqueous pool may include one or more reducing agents to convert GO to rGO during the hydrophobic self-assembly of the GO scales to rGO sheets at the water surface. In one embodiment, the reducing agent is hydrazine. Any crinkling or folding in the scale layers is preferably reduced upon arrival at the water surface. In one embodiment, the deposited scales are annealed at the water surface to improve their uniformity. In one embodiment, reactive end groups on neighboring scales react with each other to form larger graphene/graphene derivative sheets at the water surface.

The graphene/graphene derivative sheets may be applied to a solid by contacting the solid to the graphene/graphene derivative sheets at the surface of the water. The solid surface may be dipped in a vertical, horizontal, or angled orientation into the liquid surface. Alternatively, the solid surface may be located initially in the water and brought upward to the liquid surface in a vertical, horizontal, or angled orientation or the water may be drained to bring the graphene/graphene derivative sheets to the solid surface.

Alternatively, some of the water from the aqueous pool is permitted to evaporate slowly, leaving a viscous gelled graphene or graphene jelly in the upper liquid portion of the pool.

The carbon source may be in numerous forms, including, but not limited to, liquefied, powdered solid, or granular solid. In one embodiment, the carbon source preferably includes at least one essentially non-graphitic carbonaceous material having a chemical structure containing at least one 6-member carbon-containing ring, such as sucrose, the structure of which is shown as Molecule 2:

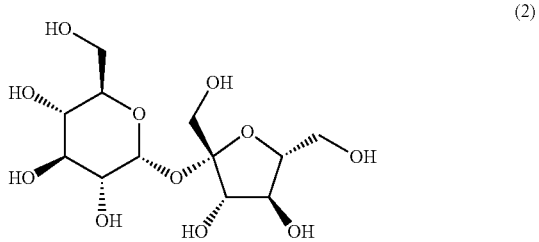 [SMILES: OC[C@H]1O[C@@](CO)(O[C@H]2O[C@H](CO)[C@@H](O)[C@H](O)[C@H]2O)[C@@H](O)[C@@H]1O]

(2)

In one embodiment, the carbon source is of a form having a significant amount of graphitic carbon.

The carbon-containing rings in the carbonaceous material, especially any aromatic carbon rings, are believed to be conserved to some degree in the chemical reactions of the growing carbon-ring matrix of the graphene or GO products; that is to say, the 6-membered carbon ring structure is believed to be retained to some degree in the graphene or GO products themselves.

The essentially non-graphitic carbonaceous material may include one or any combination of the following, but is not limited to:

1. a sugar, including, but not limited to:
   a. a molasses or molasses substitute, including, but not limited to sweet sorghum, sugar beet molasses, pomegranate molasses, mulberry molasses, carob molasses, date molasses, grape molasses, backstrap molasses, black treacle, maple syrup or corn syrup, including, but not limited to high-fructose corn syrup;
   b. an invert sugar, including, but not limited to, inverted sugar syrup;
   c. a deoxy sugar, including, but not limited to deoxyribose, fucose or rhamnose;
   d. a monosaccharide, including, but not limited to glucose, fructose, galactose, xylose or ribose;
   e. a disaccharide, including, but not limited to sucrose, lactulose, lactose, maltose, trehalose or cellobiose;
   f. a polysaccharide, including, but not limited to starch, glycogen, arabinoxylan, cellulose, chitin or pectin;
   g. a sugar alcohol, including, but not limited to erythritol, threitol, arabitol, xylitol, ribitol, mannitol, sorbitol, dulcitol, iditol, isomalt, maltitol or lactitol; or
   h. an amphiphile, including, but not limited to a sugar amphiphile or a graphene-promoting amphiphile;
2. a sugar substitute, including, but not limited to stevia, aspartame, sucralose, neotame, acesulfame potassium, saccharin, or a sugar alcohol;
3. a hydrocarbon, including, but not limited to naphthalene, diesel fuel, kerosene, gasoline, or an alkane, including, but not limited to methane, ethane, propane, cyclopropane, butane, isobutane, cyclobutane, pentane, isopentane, neopentane, cyclopentane, hexane, octane, kerosene, isoparaffins, liquid paraffins or paraffin waxes;
4. a coal form, including, but not limited to peat, lignite, bituminous coal, sub-bituminous coal, pulverized coal, nano-coal, steam coal, cannel coal, anthracite, charcoal, carbon black, activated charcoal, "activated nano-coal" or sugar char;
5. an alcohol, including, but not limited to ethanol, methanol, or isopropanol; or
6. an oil, including, but not limited to linseed oil, citronella oil, geraniol or mineral oil.

In one embodiment, the essentially non-graphitic carbonaceous material comprises a pyranose, a furanose, a cyclic carbomer, or a benzenoid (see Katritzky et al., "Aqueous High-Temperature Chemistry of Carbo- and Heterocycles. 20.[1] Reactions of some Benzenoid Hydrocarbons and Oxygen-Containing Derivatives in Supercritical Water at 460° C.", *Energy & Fuels*, Vol. 8, pp. 487-497, 1994), including, but not limited to, oxygen-containing benzenoids.

In one embodiment, the essentially non-graphitic carbonaceous material comprises a sugar. In one embodiment, the essentially non-graphitic carbonaceous material comprises sucrose. In one embodiment the sugar comprises a molasses or molasses substitute, which may comprise, but is not limited to, sweet sorghum, sugar beet molasses, pomegranate molasses, mulberry molasses, carob molasses, date molasses, grape molasses, backstrap molasses, black treacle, bee's honey, maple syrup, or corn syrup, including, but not limited to, high-fructose corn syrup. In some embodiments, the sugar comprises an invert sugar, which may comprise, but is not limited to, inverted sugar syrup.

In one embodiment, the sugar comprises a deoxy sugar, which may comprise, but is not limited to, deoxyribose, fucose, or rhamnose.

In one embodiment, the sugar comprises a monosaccharide, which may comprise, but is not limited to, glucose, fructose, galactose, xylose, or ribose.

In one embodiment, the sugar comprises a disaccharide, which may comprise, but is not limited to, sucrose, lactulose, lactose, maltose, trehalose, cellobiose, or sophorose.

In one embodiment, the sugar comprises a polysaccharide, which may comprise, but is not limited to, starch, glycogen, arabinoxylan, cellulose, chitin, or pectin.

In one embodiment, the essentially non-graphitic carbonaceous material comprises a sugar alcohol, which may include, but is not limited to, erythritol, threitol, arabitol, xylitol, ribitol, mannitol, sorbitol, dulcitol, iditol, isomalt, maltitol, or lactitol.

In one embodiment, the essentially non-graphitic carbonaceous material comprises a sugar substitute, which may include, but is not limited to, stevia, aspartame, sucralose, neotame, acesulfame potassium, or saccharin.

In one embodiment, the essentially non-graphitic carbonaceous material comprises a sugar derivative, which may include, but is not limited to, sophoritol, a phenolic glycoside, a steviol glycoside, a saponin, a glycoside, a glucoside, or amygdalin.

In one embodiment, the essentially non-graphitic carbonaceous material comprises a cyclomethicone, which may include, but is not limited to, phenyl trimethicone or cyclopentasiloxane.

In one embodiment, the essentially non-graphitic carbonaceous material comprises a steroid, which may include, but is not limited to, sapogenin or diosgenin.

In one embodiment, the essentially non-graphitic carbonaceous material comprises a cinnamate, which may include, but is not limited to, methyl or ethyl cinnamate. In one embodiment, the essentially non-graphitic carbonaceous material comprises cinnamic acid. In one embodiment, the additive comprises cinnamon oil.

In one embodiment, the essentially non-graphitic carbonaceous material comprises a phenylphopanoid, which may include, but is not limited to, cinnamic acid, coumaric acid, caffeic acid, ferulic acid, 5-hydroxyferulic acid, sinapic acid, cinnamaldehyde, umbelliferone, resveratrol, a monolignol, which may comprise, but is not limited to, coniferyl alcohol, coumaryl alcohol, or sinapyl alcohol, or a phenylpropene, which may comprise, but is not limited to, engenol, chavicol, safrole, or estragole.

In one embodiment, the essentially non-graphitic carbonaceous material comprises a benzoate, which may include, but is not limited to, ferric, benzyl, ethyl, methyl, phenyl, cyclohexanol, 2-phenyl-, pentaerythritol tetra-, sodium, or potassium benzoate. In one embodiment, the additive includes benzoic acid. In one embodiment, the essentially non-graphitic carbonaceous material comprises aminobenzoic acid. In one embodiment, the essentially non-graphitic carbonaceous material comprises 2-hydroxymethyl benzoic acid methyl ester. In one embodiment, the essentially non-graphitic carbonaceous material includes ubiquinone.

In one embodiment, the essentially non-graphitic carbonaceous material comprises a carboxylate, including but not limited to trimethyl cis, cis-1,3,5-cyclohexanetricarboxylate.

In one embodiment, the essentially non-graphitic carbonaceous material comprises a benzopyran, which may include, but is not limited to, chromene, isochromene, or a substituted benzopyran.

In one embodiment, the essentially non-graphitic carbonaceous material comprises a naturally-occurring or synthetic flavone or isoflavone, which may include, but is not limited to, flavan-3-ol or flavanone.

In one embodiment, the essentially non-graphitic carbonaceous material comprises a salicylate, which may include, but is not limited to, ferric, methyl, ethyl, butyl, cinnamyl, cyclohexyl, ethylhexyl, heptyl, isoamyl, octyl, benzyl, phenyl, p-cresol, o-cresol, m-cresol, or sodium salicylate. In one embodiment, the essentially non-graphitic carbonaceous material includes salicylic acid. In one embodiment, the additive includes aminosalicylic acid.

In one embodiment, the essentially non-graphitic carbonaceous material comprises an antioxidant. In one embodiment, the antioxidant is a cyclic antioxidant. In one embodiment, the antioxidant is a phenolic antioxidant, which may include, but is not limited to, 2,6-di-terti-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-1-buty 1-phenol, 2,6-di-cyclopentyl-4-methylphenol, 2-(α-methylcyclohexyl)-4,6-dimethylphenol, 2,6-di-octadecyl-methylphenol, 2,4,6-tri-cyclohexylphenol, 2,6-di-tert-butyl-4-methoxymethylphenol, 2,6-di-tert-butyl-4-methoxyphenol, 2,5-di-tert-butyl-hydroquinone, 2,5-di-tert-amyl-hydroquinone, 2,6-diphenyl-4-octadecyloxyphenol, 2,2'-methylene-bis-(6-tert-butyl-4-methylphenol), 2,2'-methylene-bis-(6-tert-butyl-4-ethylphenol), 2,2'-methylene-bis-[4-methyl-6-α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-[6-(α-methylbenzyl)-4-nonylphenol], 2,2'-methylene-bis-[6-(α,α-dimethylbenzyl)-4-nonylphenol], 2,2'-methylene-bis-(4,6-di-tert-butylphenol), 2,2'-ethylidene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-di-(3-tert-butyl-5-methyl-2-hydroxybenzyl)-4-methylphenol, 1,1,3-tris-(5-tert-butyl-4-hydroxy-2-methylphenyl)-butane, and any naturally-occurring plant-based phenolic antioxidant, which may include, but is not limited to, ascorbic acid, a tocopherol, a tocotrienol, rosemarinic acid, and other phenolic acids and flavonoids, such as those found, for example, in grapes, berries, olives, soy, tea leaves, rosemary, basil, oregano, cinnamon, cumin, and turmeric.

In one embodiment, the essentially non-graphitic carbonaceous material comprises 4-vinylphenol, anthocyanidin, or chromenylium.

In one embodiment, the essentially non-graphitic carbonaceous material comprises a cyclic amino acid, which may include, but is not limited to, phenylalanine, tryptophan, or tyrosine.

In one embodiment, the essentially non-graphitic carbonaceous material comprises a cyclohexane derivative, which may include, but is not limited to, 1,3-cyclohexadiene or 1,4-cyclohexadiene.

In one embodiment, the essentially non-graphitic carbonaceous material comprises a benzene derivative which may include, but is not limited to, a polyphenol, benzaldehyde, benzotriazole, benzyl 1-naphthyl carbonate, benzene, ethyl benzene, toluene, styrene, benzonitrile, phenol, phthalic anhydride, phthalic acid, terephthalic acid, p-toluic acid, benzoic acid, aminobenzoic acid, benzyl chloride, isoindole, ethyl phthalyl ethyl glycolate, N-phenyl benzamine, methoxybenzoquinone, benzylacetone, benzylideneacetone, hexyl cinnamaldehyde, 4-amino-2-hydroxytoluene, 3-aminophenol, or vanillin.

In one embodiment, the benzene derivative comprises a benzenediol, which may include 1,2-dihydroxybenzene (catechol), 1,3-dihydroxybenzene (resorcinol), or 1,4-dihydroxybenzene (hydroquinone).

In one embodiment, the essentially non-graphitic carbonaceous material comprises a naphthoate, including but not limited to methyl 2-methoxy-1-naphthoate or methyl 3-methoxy-2-naphthoate.

In one embodiment, the essentially non-graphitic carbonaceous material comprises an acrylate, including but not limited to benzyl 2-propylacrylate or 2-naphthyl methacrylate.

In one embodiment, the essentially non-graphitic carbonaceous material comprises a phthalate, including but not limited to diallyl phthalate.

In one embodiment, the essentially non-graphitic carbonaceous material comprises a succinate, including but not limited to bis(2-carboxyphenyl)succinate.

In one embodiment, the essentially non-graphitic carbonaceous material comprises a carpate, including but not limited to methyl O-methylpodocarpate.

In one embodiment, the essentially non-graphitic carbonaceous material comprises a fluorophore, which may include, but is not limited to, fluorescein isothiocyanate, rhodamine, phthalocyanine, or copper phthalocyanine.

In one embodiment, the essentially non-graphitic carbonaceous material comprises a pharmaceutical, which may include, but is not limited to, acetylsalicylic acid, acetaminophen, ibuprofen, or a benzodiazepine.

In one embodiment, the essentially non-graphitic carbonaceous material comprises a phosphate, which may include, but is not limited to, a cresyldiphenyl phosphate, a dicresyl phosphate, a triorthocresyl phosphate, a tricresyl phosphate, a paracresyl phosphate, an orthocresyl phosphate, or a metacresyl phosphate.

In one embodiment, the essentially non-graphitic carbonaceous material comprises a compound that degrades to one or more of the above-mentioned additives under the heat of the operating conditions of the engine or mechanical system, such as certain terpenes or certain natural aromatic or non-aromatic cyclic esters, ketones, or aldehydes, which may include, but is not limited to, methyl salicylate (wintergreen oil), cinnamon leaf/bark oil (cinnamaldehyde), limonene (dipentene), pinene, and camphene.

In one embodiment, the essentially non-graphitic carbonaceous material comprises a commercial edible personal/sexual lubricating composition including a sugar or sugar-substitute amphiphile.

In one embodiment, the essentially non-graphitic carbonaceous material comprises a commercial ultraviolet ray sunscreen formulation, which may include octyl methoxycinnamate (oxtinoxate), butyl-methoxydibenzoylmethane (B-MDM, Avobenzone), octyl-dimethyl-para-aminobenzoic acid (OD-PABA), octocrylene, oxybenzone, alkyl benzoate, diethylhexyl 2,6-naphthalate, phenoxy-ethanol, homosalate, ethylhexyl triazone, 4-methyl-benzylidene camphor (4-MBC), or a polysorbate.

In one embodiment, the essentially non-graphitic carbonaceous material comprises a commercial skin cream formulation, which may include, but is not limited to carbomer, ascorbyl palmitate, tocopheryl acetate, ketoconazole, or mineral oil.

In one embodiment, the essentially non-graphitic carbonaceous material comprises a commercial hand sanitizer formulation, which may include carbomer, tocopheryl acetate, or propylene glycol.

In one embodiment, the essentially non-graphitic carbonaceous material comprises a commercial human or animal hair care product, which may include benzophenone, alkyl benzoate, phenoxyethanol, sorbitan oleate, a styrene copolymer, propylene glycol, hydroxyisohexyl-3-cyclohexene carboxaldehyde, butylated hydroxytoluene, ketoconazole, petrolatum, mineral oil, or paraffinum liquidum.

In one embodiment, the commercial hair care product is a curl activating or relaxing solution, which may include carbomer, hexyl cinnamal, benzyl salicylate, trolamine salicylate, benzyl benzoate, limonene, eugenol, 1,3-Bis(hydroxymethyl)-5,5-dimethyl-limidazolidine-2,4-dione (DMDM Hydantoin), para-aminobenzoic acid (PABA), 2-ethylhexyl 4-dimethylaminobenzoate (Padimate O), butylphenyl methylpropional, propylparaben, phenolsulfonphthalein (PSP, phenol red), or a polysorbate.

In one embodiment, the essentially non-graphitic carbonaceous material comprises a commercial hair dye formulation, which may include hydrated iron oxide ($Fe(OH)_3$), para-phenylenediamine, ortho-, meta-, or para-aminophenol, 4-amino-2-hydroxytoluene, trideceth-2 carboxamide MEA, phenyl methylpyrazolone, phenoxyethanol, a polyquaternium, hexyl cinnamal, butylphenyl methylpropional, phenolsulfonphthalein (PSP, phenol red), hydroxyisohexyl 3-cyclohexene carboxaldehyde, titanium dioxide, or iron oxide.

In one embodiment, the essentially non-graphitic carbonaceous material comprises a commercial pesticide, which may include, but is not limited to, ortho-phenylphenol (OPP), phenylhydroquinone (PHQ) or phenylbenzoquinone (PBQ).

The oxidizer may be in any form, including, but not limited to, gaseous, liquefied, powdered solid, or granular solid. The oxidizer may include one or any combination of the following, but is not limited to potassium nitrate, gaseous oxygen, sodium nitrate, ammonium dichromate, ammonium nitrate, ammonium perchlorate, potassium perchlorate, potassium permanganate, calcium nitrate, hydrogen peroxide, sodium bicarbonate, or mercury thiocyanate.

In one embodiment, the reaction mixture includes a solvent. The solvent may include an alcohol, including one or any combination of the following, but is not limited to methanol, ethanol, isopropyl alcohol, n-propanol, or a gelled alcohol formulation, including, but not limited to a jellied, denatured alcohol formulation, such as a formulation including ethanol and methanol as found in Sterno® brand canned heat (The Sterno Group, LLC, Des Plaines, Ill., United States), or a gelled alcohol formulation such as found in hand sanitizers, including formulations containing such thickening agents as polyacrylic acid, or propylene glycol.

In one embodiment, the reaction mixture includes one or more catalysts or other additives. The additive or catalyst may include one or any combination of the following, but is not limited to sodium bicarbonate, aluminum bicarbonate, sodium aluminum phosphate, sodium aluminum sulfate, potassium carbonate, potassium phosphate, potassium hydroxide, aluminum hydroxide, magnesium hydroxide, magnesium sulfate, magnesium phosphate, cream of tartar, citric acid, ascorbic acid, sucrase, invertase, ferrocene, or a transition metal oxide catalyst, which may be in a nanopowder form, the catalyst including one or any combination of the following, but not limited to an iron oxide, including iron(II) oxide, iron(II, III) oxide, iron(III) oxide, iron(II) hydroxide, iron(III) hydroxide, or iron(III) oxide-hydroxide, aluminum oxide, a copper oxide, including, but not limited to copper(I) oxide, or copper(II) oxide, a nickel oxide, including, but not limited to nickel(I) oxide, or nickel(II) oxide, a titanium oxide, including, but not limited to titanium dioxide, titanium (I) oxide, or titanium(II) oxide, or a lead oxide, including, but not limited to lead(II) oxide, lead(IV) oxide, lead tetroxide, or a lead sesquioxide.

In one embodiment, sucrose and sodium bicarbonate are combined in about a 4:1 volume ratio, with ethanol added as a solvent, to form the reaction mixture.

In one embodiment, the reactants are mixed with a flammable solvent such as methanol, ethanol, or isopropanol. In some of these embodiments, the carbon source is dissolved in the flammable solvent. In other embodiments, the reactants form a slurry with the solvent.

In one embodiment, the reaction is performed in the absence of a solvent.

In one embodiment, powdered sugar and sodium bicarbonate powder are combined in a 4-to-1 ratio and mixed with a metal oxide catalyst prior to exposure to heat.

In one embodiment, the reaction mixture may additionally or alternatively include one or more of sodium bicarbonate, naphthalene, and linseed oil.

In one embodiment, sucrose and potassium nitrate are combined in a ratio of about 35:65 to form the reaction mixture (see *Rocket Manual for Amateurs* by B. R. Brinley, Ballantine Books, New York, N.Y., 1960, and *Amateur Experimental Rocketry*, Vol. 7 by Richard Nakka, self-published on CD only, January 2011). In one embodiment, the reaction mixture further includes a metal oxide in the range of about 1% to about 30%, preferably about 5%.

In one embodiment, powdered sugar and an alcohol, preferably ethanol or isopropanol, are placed in a reaction vessel and mixed to form a paste reaction mixture. The reaction mixture is heated to produce a vapor containing vapor-exfoliated graphene/graphene derivative scale. In some embodiments, the reaction mixture further includes iron oxide in the form of BayFerrox® iron oxide powder pigment (Lanxess, Cologne, Germany). In other embodiments, the iron oxide is in the form of high-purity $Fe_3O_4$ (15-20 nm) nanopowder (U.S. Research Nanomaterials, Inc., Houston, Tex., United States).

In one embodiment, powdered sugar and gelled alcohol, in the form of a conventional hand sanitizer, including water, polyacrylic acid, and ~60% isopropyl alcohol, are placed in a reaction vessel and mixed together to form a reaction mixture. The reaction mixture is heated to produce a vapor containing vapor-exfoliated graphene/graphene derivative scales. In some embodiments, the reaction mixture further includes iron oxide in the form of BayFerrox® iron oxide powder pigment (Lanxess, Cologne, Germany). In other embodiments, the iron oxide is in the form of high-purity $Fe_3O_4$ (15-20 nm) nanopowder (U.S. Research Nanomaterials, Inc., Houston, Tex., United States).

In one embodiment, a reaction mixture of powdered sugar and an alcohol, preferably ethanol, is heated in a reaction vessel using a hot plate to a temperature lower than in previously-described embodiments using a direct flame. The reaction mixture is heated to a point causing vapor formation containing vapor-exfoliated graphene/graphene derivative scales. In one embodiment, the reaction mixture further includes iron oxide in the form of BayFerrox® iron oxide powder pigment (Lanxess, Cologne, Germany). In one embodiment, the iron oxide is in the form of high-purity $Fe_3O_4$ (15-20 nm) nanopowder (U.S. Research Nanomaterials, Inc., Houston, Tex., United States).

In one embodiment, the iron oxide source is a substrate onto which the other reactants are placed. In one embodiment, the iron oxide source is a rusted iron-based metal part. The reactants are then heated as in one of the previously-described embodiments.

In one embodiment, the carbonaceous material is coal or a coal derivative. In one embodiment, the coal is a pulverized coal. In one embodiment, the coal is a nano-coal. In one embodiment, the carbonaceous material is one or more of coal, coke, and coal tar. In one embodiment, the coal or coal derivative is heated in a high boiling point temperature solvent to reflux temperatures. In one embodiment, the process is a poor or improper form of a coal tar distillation or coke oven with reaction gases being re-condensed and dripping back into the reaction mixture.

In one embodiment, the carbonaceous material is sucrose. In some embodiments, concentrated sulfuric acid converts the sucrose to graphitic carbon, which may form with a foam morphology from trapped reaction gases, by a dehydration reaction as shown in Equation 4:

$$C_{12}H_{22}O_{11} \xrightarrow{98\% \ sulfuric \ acid} 12 \ C_{graphitic} + 11 \ H_2O \tag{4}$$

In one embodiment, an excess of sulfuric acid is used, such that any water vapor or other gases formed during the dehydration reaction are released from the reaction mixture and the graphitic carbon product is not in the form of a foam. In one embodiment, excess heat is provided to the system to promote the release of all reaction gases.

In one embodiment, heat is used to convert the sucrose to carbon by a dehydration reaction as shown in Equation 5:

$$C_{12}H_{22}O_{11} \xrightarrow{heat} 12 \ C_{graphitic} + 11 \ H_2O \tag{5}$$

In one embodiment, a graphitic carbon source and a liquid are placed in a reaction vessel and mixed together to form a slurry mixture. The graphitic carbon source may be any material including graphitic carbon, including, but not limited to, natural graphite, synthetic graphite, one or more polycyclic aromatic hydrocarbons (PAHs), graphene, activated carbon, biochar, coal phlegm, one or more benzenoids, naphthalene, or any combination of these. In one embodiment, the graphitic carbon source is natural or synthetic graphite. In one embodiment, the graphite is ground into a fine powder. In one embodiment, the graphitic carbon source is an activated carbon. In one embodiment, the liquid includes one or any combination of an alcohol, water, or mineral oil. In one embodiment, the liquid is an acid or a strongly acidic solution. In one embodiment, the alcohol is methanol. The slurry mixture is heated to produce a vapor containing vapor-exfoliated graphene/graphene derivative scales. In one embodiment, the reaction mixture further includes iron oxide in the form of BayFerrox® iron oxide powder pigment (Lanxess, Cologne, Germany). In one embodiment, the iron oxide is in the form of high-purity $Fe_3O_4$ (15-20 nm) nanopowder (U.S. Research Nanomaterials, Inc., Houston, Tex., United States).

In one embodiment, a graphitic carbon product from the dehydration of sucrose and a solvent are placed in a reaction vessel and mixed together to form a slurry mixture. In one embodiment, the solvent may include one or any combination of an alcohol, water, and mineral oil. In one embodiment, the alcohol is methanol, ethanol, or isopropanol. The slurry mixture is heated to produce a vapor containing vapor-exfoliated graphene/graphene derivative scales. In v, the reaction mixture further includes iron oxide in the form of BayFerrox® iron oxide powder pigment (Lanxess, Cologne, Germany). In one embodiment, the iron oxide is in the form of high-purity $Fe_3O_4$ (15-20 nm) nanopowder (U.S. Research Nanomaterials, Inc., Houston, Tex., United States).

In one embodiment, the heat source is a direct open flame. In one embodiment, the heat source is a fuel mixed with the reactants ignited by an ignition source. In one embodiment, the heat source is a hot plate. In one embodiment, an additional reagent is added to promote formation of a reaction gas. In one embodiment, the additional reagent is sodium bicarbonate and the reaction gas is carbon dioxide. In one embodiment, the reactants are heated to autoignition.

In one embodiment, the chemical reaction may purposefully occur under pyrolysis conditions. In one embodiment, a reaction may purposefully occur under conditions of insufficient oxygen for combustion or minimal oxygen or within a partial vacuum chamber. In one embodiment, at least some of the reactants are heated during product formation in a controlled low-oxygen atmosphere. In one embodiment, a reaction may purposefully employ an additive to promote incomplete combustion and formation of soot or other products of incomplete combustion or pyrolysis. In one embodiment, the reaction may be carried out quickly by exposing the reaction mixture to the heat of a direct flame.

In one embodiment, solid reactants are mixed and heated with a direct flame in a reaction container such as a crucible. Although the fuel for the flame may be any fuel within the spirit of the present invention, the fuel in these embodiments is preferably a relatively clean-burning fuel such as methane, ethane, propane, or butane.

In one embodiment, the heat source is direct flame.

In one embodiment, the system is externally heated to a temperature just below an autoignition temperature for the system to initiate product formation.

In one embodiment, the graphene or GO is formed as a product of heating an intumescent. Intumescents are commonly used as fire retardants. An intumescent, as used herein, is any carbonaceous material that swells but does not burn when exposed to heat. The intumescent may include one or any combination of the following, but is not limited to dicresyl phosphates, tricresyl phosphates, including, but not limited to paracresyl phosphates, orthocresyl phosphates, or metacresyl phosphates polymer resin precursors, or certain epoxy resins, including, but not limited to thermosetting resins, including, but not limited to phenol-formaldehyde (PF) resins, melamine resins, cyanate ester resins, or polycyanurates, polyphenylene ether (PPO) resins, ethylene propylene diene monomer (EPDM) resins, or polyolefin plastomer (POP) resins.

In one embodiment, heating the intumescent produces a poor heat-conducting light char. In one embodiment, heating the intumescent produces a heavy char. In one embodiment, the resulting char is subjected to solvent attack and reheated to produce the graphene or GO product. In one embodiment, the resulting char may then serve as the carbonaceous material for addition to, and reaction with, an oxidizer. In one embodiment, the char may be combined with an oil and heated to produce the graphene or GO reaction product.

In one embodiment, as outlined supra, the carbonaceous material carbon source added to the reactants, or additive, may include one or any combination of the following, but is not limited to linseed oil, a light paraffinic oil, a naphthalenic compound, a resin, a resin precursor, an alkyd, an alkyd resin, or an alkyd precursor, including, but not limited to, a polyol, including, but not limited to maltitol, xylitol, sorbitol, isomalt, pentaerythritol, ethylene glycol, glycerin or polyester.

In one embodiment, the reactants include one or more polyols, one or more acid anhydrides, or one or more unsaturated fatty acid triglycerides.

It is envisioned that modifications to the above-described methods may provide for easier collection of the graphene or GO and may produce a higher yield.

In one embodiment, no liquid or gel mixing medium is used. In one embodiment, the mixing medium is methanol. In one embodiment, the mixing medium is water. In one embodiment, the mixing medium is a solid, semi-solid, or gelatinous flammable material, which may be mixed with the carbon source. In one embodiment, the flammable material is a gel fuel made from denatured alcohol, water, and gel, such as Sterno® brand canned heat (The Sterno Group LLC, Des Plaines, Ill., United States). In one embodiment, the denatured alcohol includes ethanol with one or more additives, which may include one or any combination of the following, but is not limited to methanol, isopropanol, acetone, methyl ethyl ketone, methyl isobutyl ketone, or denatonium.

In one embodiment, the gel fuel is made from vinegar, calcium carbonate, and isopropanol. In such embodiments, the gel fuel may be gently heated to become more fluid for mixing with the reactants and then cooled to re-gel. In such an embodiment, a direct flame may be used only initially to ignite the gel fuel and initiate the reaction, with the flame being sustained by the burning of the gel fuel itself.

In one embodiment, the vapor-borne graphene or graphene derivative scales are collected by deposition onto a solid surface contacting the vapor-borne scales.

In one embodiment, the vapor-borne graphene or graphene derivative scales are collected using clean coal technology. In one embodiment, a scrubber (see, for example, Semrau, "Practical process design of particulate scrubbers", Chem. Eng., Vol. 84, pp. 87-91, 1977), preferably a wet scrubber, is used to collect any vapor-borne graphene or GO scales. In one embodiment, flue gases are treated with steam to collect vapor-borne particles including any vapor-borne graphene or GO scales.

In one embodiment, the vapor-borne graphene or graphene derivative scales are collected by bubbling the produced vapor stream through a liquid. In one embodiment, the liquid is water. In other embodiments, the liquid is an oil, which may include, but is not limited to a vegetable oil or a lubricating oil. In one embodiment, a surfactant is added to the water to promote formation of a uniform layer of graphene or graphene derivative at the surface of the water. In one embodiment, the liquid is heated to promote the formation, via self-assembly, of a uniform layer of graphene or graphene derivative at the surface of the liquid. In one embodiment, the liquid is heated to near its boiling temperature. In one embodiment, additives are used to raise the boiling temperature of the liquid. In one embodiment, ultrasound is applied to the liquid to promote graphene or graphene derivative self-assembly on the liquid surface. In one embodiment, ultraviolet light is applied to the liquid to promote graphene or graphene derivative self-assembly on the liquid surface. In one embodiment, an argon atmosphere above the liquid promotes graphene or graphene derivative self-assembly on the liquid surface. In one embodiment, a reduced pressure is used to promote self-assembly of the graphene or graphene derivative (see Putz et al., "Evolution of Order During Vacuum-Assisted Self-Assembly of Graphene Oxide Paper and Associated Polymer Nanocomposites", *ASC Nano*, Vol. 5, pp. 6601-6609, 2001).

In one embodiment, the solvent remaining in the reaction flask containing graphitic material after completion of the pyrolysis step is used as a coating to form a composite reinforced by the graphitic material. In one embodiment, the graphitic-containing solvent is applied by dipping the material to be coated into the graphitic-containing solvent. In one embodiment, individual fibers are coated. In other embodiments, a fiber mesh is coated. In one embodiment, multiple layers are deposited to cover up any cracks in the graphitic material, thereby strengthening the coating.

In one embodiment, the graphitic-containing solvent is mixed with a structural material to form a graphene-reinforced composite. In one embodiment, the graphitic-containing solvent is combined with pre-impregnated composite fibers (pre-preg) to form a graphene-reinforced composite material. In one embodiment, the carbon source for the graphitic material is a resin precursor for the particular resin to be reinforced by the graphitic material.

In one embodiment, the aqueous collecting liquid used to accumulate the combustion product vapor is used in a mould to facilitate the fabrication of solid composite materials that make use of the combustion products.

In one embodiment, the reaction vapors are collected and channeled directly onto the interior or exterior surface of a mould, without the use of a liquid collection medium.

In one embodiment, the reaction vapors are collected and channeled directly onto the surface of a solid substrate. In one embodiment, the solid substrate is a fiber and a graphene-reinforced fiber composite is formed upon deposition. In one embodiment, the fiber is carbon fiber. In one embodiment, the fiber is polymeric. The graphene coating may be applied to the fiber either before or after weaving individual fibers together depending on the application and the desired properties for the graphene-fiber composite. In one embodiment, multiple layers are deposited to cover up cracks in the graphene sheets, thereby strengthening the coating.

In one embodiment, the resulting collected vapor is suspended on a liquid that is later drained, evaporated, or otherwise removed, allowing the graphene, GO, or rGO sheets to coat the inside of a mould or to be deposited on a solid or liquid substrate already in such mould or introduced into the mould, for the purpose of producing a composite material.

Figure 3:
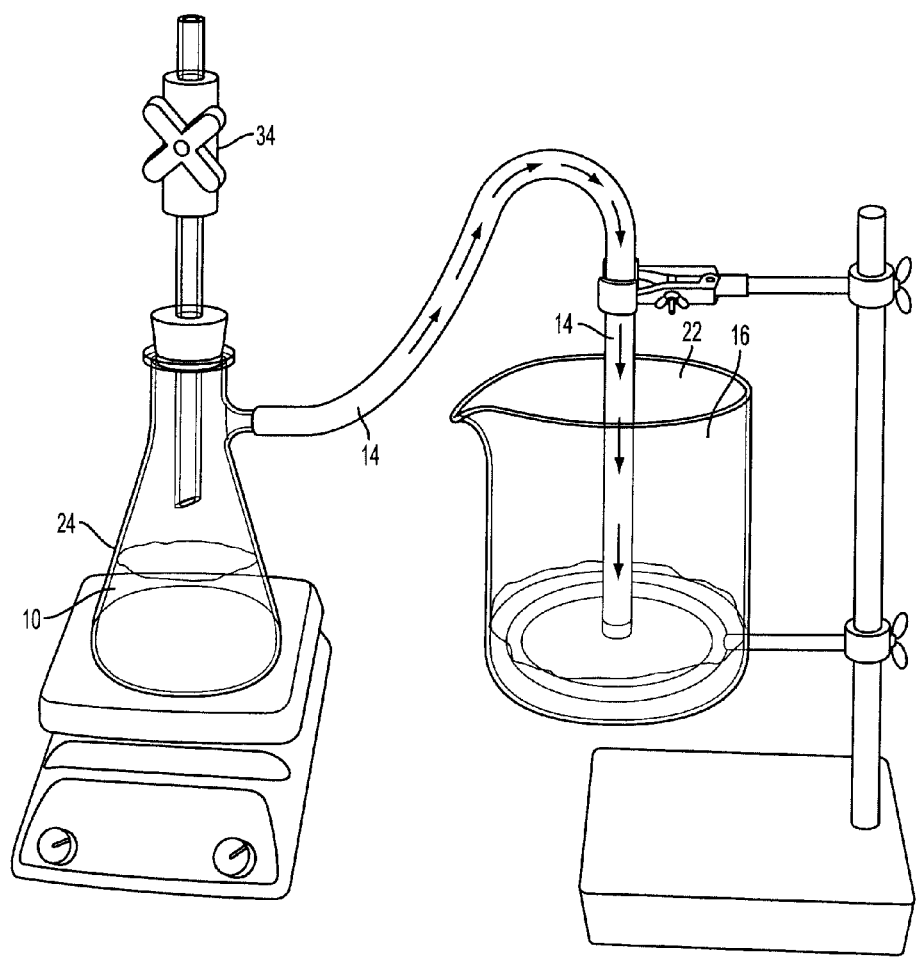
FIG. 3 shows a schematic graphene/GO/SGAN synthesis and collection system in an embodiment of the invention.

In the system of FIG. 3, a reaction mixture is placed in a reaction vessel 10. Heat is applied to the reaction vessel 10 by a heating element 12. Generated reaction gases and gas-borne product build pressure in the reaction vessel 10 and exit the reaction vessel by a conduit 14. The reaction gas stream exits the conduit 14 above the surface of liquid 16. In another embodiment (not shown), conduit 14 directs the vapor below the surface of liquid 16 whereupon it bubbles to the surface 18 of the liquid 16. In one embodiment (not shown), a sparger is attached to the end of conduit 14 provides multiple release points to distribute the reaction gas stream bubbles either under or above the surface the liquid. The reaction gases are released into the atmosphere 22 above the liquid surface 18, while the graphene/graphene derivative product remains in the liquid, primarily accumulating at the liquid surface 18. Alternatively, the conduit 14 may release the reaction gas stream directly into the atmosphere 22 above the liquid surface 18. In some such embodiments, the reaction gas stream is directed toward the liquid surface 18 by the conduit 14.

A temperature control element 24 may be used to control the temperature of the liquid by providing heat or cooling to promote formation of large graphene oxide sheets by hydrophobic self-assembly at the liquid surface. Either the temperature control element 24 or a separate ultrasound element may provide ultrasonic vibration to promote formation of large graphene oxide sheets at the liquid surface. A cover (not shown) can be employed to cover liquid 16 to therefore create a closed controllable environment 22 above the liquid 16. In one embodiment (not shown), an increased pressure is maintained in the environment 22 by a pressure source through a valve. In one embodiment, the pressure source is an inert gas, such as argon, to provide an inert environment above the liquid. In one embodiment (not shown), a release valve enables the release of excess pressure from the atmosphere 22. The reaction vessel 10 preferably includes a pressure equalizing valve 34 to relieve excess vacuum formed in the reaction vessel 10, which prevents liquid from being drawn in to the conduit 14 toward the reaction vessel 10 during refluxing and reaction.

In one embodiment, the reaction vessel is a Büchner flask apparatus. In one embodiment, the top of the flask is stoppered and tubing is connected to the flask's hose barb. In one embodiment, the other end of the tubing is placed under a liquid without any kind of sparger at the end of the tubing. In one embodiment, the pressure equalizing valve is connected to a line extending through the stopper on the top of the Büchner flask.

In one embodiment, the graphene or graphene derivative formed at the surface of the liquid is transferred to a solid substrate by simply contacting such solid substrate with the surface of the liquid, such as by a Langmuir-Blodgett-type deposition (see, for example, Blodgett, "Films built by depositing successive monomolecular layers on a solid surface", *J. Amer. Chem. Soc.*, Vol. 57, pp. 1007-1022, 1935).

In one embodiment, the collected GO or graphene product is further reduced or otherwise treated to remove remaining impurities from the product.

In one embodiment, the GO reaction product is converted to reduced graphene oxide (rGO). In one embodiment, the GO is chemically reduced to rGO, as generically represented in Equation 4:

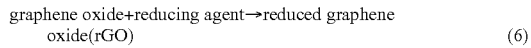

graphene oxide+reducing agent→reduced graphene oxide(rGO)  (6)

In one embodiment, the GO is colloidally dispersed in water or another liquid and chemically reduced to rGO using hydrazine monohydrate (see Stankovich et al., "Synthesis of graphene-based nanosheets via chemical reduction of exfoliated graphite oxide", *Carbon*, Vol. 45, pp. 1558-1565, 2007, Gao et al., "Hydrazine and Thermal Reduction of Graphene Oxide: Reaction Mechanisms", *J. Phys. Chem. C*, Vol. 114, pp. 832-842, 2010), Si et al., "Synthesis of Water Soluble Graphene", *Nano Lett.*, Vol. 9, pp. 1679-1682, 2008). In another embodiment, the GO is chemically reduced to rGO using hydroquinone (see Wang et al., "Facile Synthesis and Characterization of Graphene Nanosheets", *J. Phys. Chem. C*, Vol. 112, pp. 8192-8195, 2008). In another embodiment, the GO is chemically reduced to rGO using gaseous hydrogen (see Wu et al., "Synthesis of high-quality graphene with a predetermined number of layers", *Carbon*, Vol. 47, pp. 493-499, 2009). In other embodiments, the GO is chemically reduced to rGO using a strongly basic solution (see Fan et al., "Deoxygenation of Exfoliated Graphite Oxide under Alkaline Conditions: A Green Route to Graphene Preparation", *Adv. Mater.*, Vol. 20, pp. 4490-4493, 2008, Boehm et al., "Das Adsorptionsverhalten sehr dünner Kohlenstoff-Folien", *Z. Anorg. Allg. Chem.*, Vol. 316, pp. 119-127, 1962).

In one embodiment, heat or an electrical current is used to reduce the GO to rGO. In one embodiment, the GO is thermally exfoliated and reduced to rGO upon heating to 1050° C. and extrusion to remove generated carbon dioxide (see McAllister et al., "Single Sheet Functionalized Graphene by Oxidation and Thermal Expansion of Graphite", *Chem. Mater.*, Vol. 19, pp. 4396-4404, 2007). In one embodiment, the GO is electrochemically reduced to rGO by placing electrodes at opposite ends of a graphene oxide film on a non-conductive substrate and applying an electrical current (see Zhou et al., "Controlled Synthesis of Large-Area and Patterned Electrochemically Reduced Graphene Oxide Films", *Chem.-Eur. J.*, Vol. 15, pp. 6116-6120, 2009).

In one embodiment, the addition of hydrazine monohydrate to the water, through which the produced graphene oxide is bubbled, followed by heating the aqueous solution to ~80° C. converts the graphene oxide product to a self-assembled film of reduced graphene oxide platelets at the air-water interface (see Zhu et al., "Transparent self-assembled films of reduced graphene oxide platelets", *Appl. Phys. Lett.*, Vol. 95, pp. 103, 104-1-103, 104-3, 2009). Additional external forces may be applied to the liquid to encourage self-assembly of the rGO platelets, including, but not limited to, ultrasonic vibrations or ultraviolet light.

In one embodiment, the above-described products are used in combination with polymer resins to form high-strength composites. The polymer resins are preferably epoxy polymer resins. In some embodiments, the composites further include carbon fibers.

In one embodiment, the polymer resin and the graphene/graphene derivative are formed as alternating layers in the composite. In one embodiment, a graphene/graphene derivative layer is deposited as a vapor onto a polymer resin layer. In one embodiment, a graphene/graphene derivative layer is deposited from an aqueous surface onto a polymer resin layer. In one embodiment, a graphene/graphene derivative paste is applied to a polymer resin layer.

In one embodiment, the graphene/graphene derivative is formed directly on the polymer resin layer by dehydration of sucrose using concentrated sulfuric acid, where the polymer resin material is highly resistant to sulfuric acid. Highly sulfuric acid-resistant polymeric materials include, but are not limited to, polyvinyl chloride (PVC), chlorinated PVC (CPVC), polyvinylediene fluoride, polytetrafluoroethylene (PTFE), poly(chlorotrifluoroethylene) (CTFE), epoxy resin fiberglass, and EP21AR epoxy (Master Bond, Inc., Hackensack, N.J., United States).

In one embodiment, the resin is one of the following or a hybrid-type combination of the following polymer resins (1) one or more thermoplastic alkyl phenol resins, typically used in the manufacture of tires, (2) one or more NOVOLAC®-type paraoctylphenol (POP) formaldehyde resins, (3) one or more POLYTONE®-type para-tertiary butylphenol (PTBP) formaldehyde non-heat-reactive tackifying resins, (4) one or more polyphenylene ether (PPE) resins, and (5) one or more polyphenylene oxide (PPO) resins, including, but not limited to, one or more siloxane polyphenylene oxide resins.

In one embodiment, the graphene/graphene derivative is mixed with the polymer resin before the resin sets. In one embodiment, carbon fibers are also mixed with the graphene/graphene derivative and un-set polymer resin. The type of polymer resin and the relative levels of graphene/graphene derivative and carbon fiber are preferably selected to provide an appropriate balance of strength and flexibility preferred for a particular specific use or application for the resulting composite product.

In one embodiment, the resin for the polymer of the composite is also the carbon source for the graphene/graphene derivative part of the composite.

In one embodiment, the graphene/GO-reinforced polymer composite is used in structural applications conventionally restricted to metallic materials, such as the frame of a vehicle. In one embodiment, the polymer composite is re-moldable, and hence recyclable from use in one structure to use in another structure.

In a method of forming gelled graphene or graphene jelly, an aqueous pool containing graphene/graphene derivative scales was allowed to evaporate over time. In one embodiment, the starting materials for producing the reaction mixture to produce the graphene/graphene derivative scales comprise sucrose, baking powder, ethanol, and iron oxide. In one embodiment, the water in the aqueous pool evaporated very slowly and after a period of about one month at about room temperature, half of an original volume of ~800 mL of fluid remained in the beaker. A gooey gel layer, which could be peeled off, formed at the top of the fluid. Under this top layer, there was a cloudy whitish layer about 1½"-thick, having the consistency of a thin jelly. Although the composition and physical characteristics of these graphene jellies were not further tested, it is expected that these forms of graphene have useful physical and chemical properties.

In one embodiment, the aqueous gelled graphene or the aqueous pool with the collected graphene or graphene derivative is used in place of water in the formation of a composite material. In one embodiment, the aqueous gelled graphene or the aqueous pool with the collected graphene or graphene derivative is used in place of water in a cement mixture to form a graphene-reinforced concrete with improved strength relative to convention concrete. In one embodiment, the aqueous gelled graphene or the aqueous pool with the collected graphene or graphene derivative is used in the formation of asphalt concrete to form graphene-reinforced asphalt concrete with improved strength relative to convention asphalt concrete.

In one embodiment, carbon dioxide or carbon monoxide is used as a carbon source in the production of graphene, a graphene derivative, a carbon-encapsulated metallic nanoparticle, or nano-steel, thereby potentially removing excess carbon from the environment. Carbon monoxide and carbon dioxide are convertible into a number of different products suitable as carbonaceous feedstock for the synthesis methods contained herein, such as synthetic methanol (see, for example, Sakakura et al., "Transformation of Carbon Dioxide", *Chem. Rev.*, Vol. 107, pp. 2365-2387, 2007, Yu et al., "Copper- and copper-N-heterocyclic carbene-catalyzed C—H activating carboxylation of terminal alkynes with $CO_2$ at ambient conditions", *PNAS*, Vol. 107, pp. 20184-20189, 2010, Jiang et al., "Turning carbon dioxide into fuel", *Phil. Trans. R. Soc. A*, Vol. 368, pp. 3343-3364, 2010). In one embodiment, the carbon monoxide or carbon dioxide is first converted into one or more intermediate forms of carbonaceous material, capable of combustion or pyrolysis reactions to incorporate the carbon atom from such gasses into a useful carbon-carbon graphitic bond. In one embodiment, the intermediate in such conversion is an alcohol formed by reaction of carbon dioxide with hydrogen gas. In one embodiment, the carbon dioxide is supplied directly to the reflux mixture for reaction with hydrogen gas generated by refluxing of the reflux mixture, thereby forming the synthetic methanol in situ.

Figure 7:
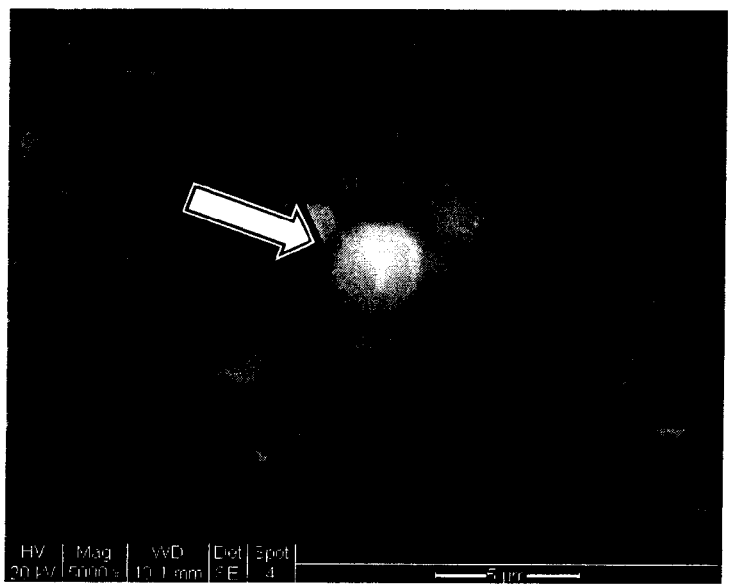
FIG. 7 shows an SEM image of an SGAN spheroid containing nano-steel in an embodiment of the invention.
Figure 8:
FIG. 8 shows an SEM image of an SGAN spheroid on an SEM stub coated by a second vapor deposition method with a sampled area in an embodiment of the invention.
Figure 9:
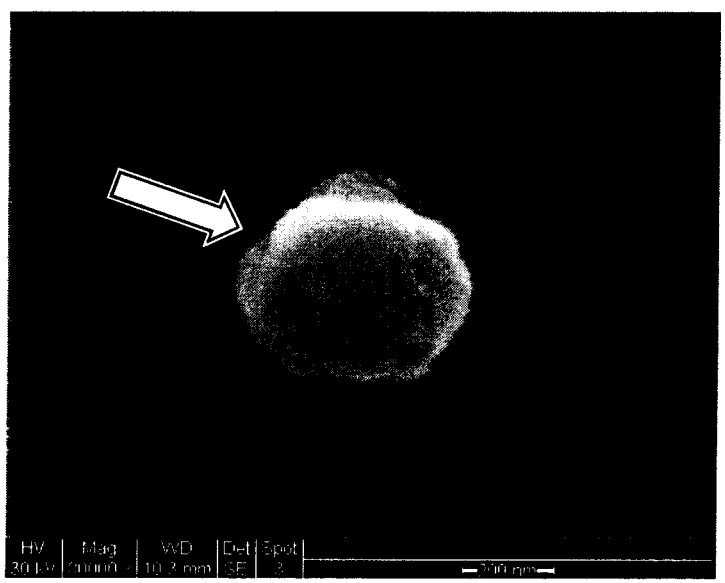
FIG. 9 shows an SEM image of another SGAN spheroid on the SEM stub.

In one embodiment incorporating iron oxide, the process operates like a nano-scale Bessemer furnace to form nano-steel. Referring specifically to FIG. 7, significant charging is observed all over the sample, especially at the edges of the spheroid. Since the sample is charging in general, the probable feature causing this charging is the presence of a non-conductive matter all over the sample. The only possible non-conductive material based on the elemental analysis would be an oxide. Thus it is concluded that there is a layer of oxide all over the stub. Regarding the charging of the spheroids, as a sharp edge is not observed in the images, the spheroids must contain both conductive and non-conductive matter. The most probable cause for this phenomenon would be elemental iron trapped in a non-conductive carbon-oxide matrix.

Elemental iron conducts and glows under the SEM but the non-conductive carbon-oxide matrix is strong enough to prevent the spheroid structure from breaking up in spite of being non-conductive and not being able to pass on the charge to the oxide layer all over the sample. The inference is that the oxide outer layer is graphene oxide and the conductive material is iron, given that the EDS reports the presence of only iron, carbon, and oxygen. If the outer shell of the balls were pure carbon, such as if the structure were graphene or a fullerene, it would have been conductive and no charging of samples would be seen, as is the case for carbon nanotubes or carbon tape materials commonly used as SEM accessories. Since the outer layer is charging, it must be non-conductive, and so the most likely form of carbon is graphene oxide. Also, as mentioned before, the entire stub charges to some extent, as shown in the SEM images. Therefore, it is also concluded that layers of graphene oxide are present all throughout the sample.

In one embodiment, the nano-steel is machined to form a nano-circuit or other nanostructure. In some embodiments, a laser etching nano-beam is used to shape the nano-steel.

Test Results

Several tests were run to create and recover graphene and its derivatives, and to produce SGANs, according to the invention.

Test 1

In a method of synthesis of SGANs, a reaction mixture was heated using a direct flame. BayFerrox® iron oxide powder pigment (Lanxess, Cologne, Germany), powdered sugar, and ethanol were placed in a reaction vessel and mixed into a paste to form a reaction mixture. The reaction mixture was heated with the direct flame of a propane torch, and an SEM stub was held above the heated reaction mixture in the smoke and/or vapor produced by heating the reaction mixture.

Figure 4:
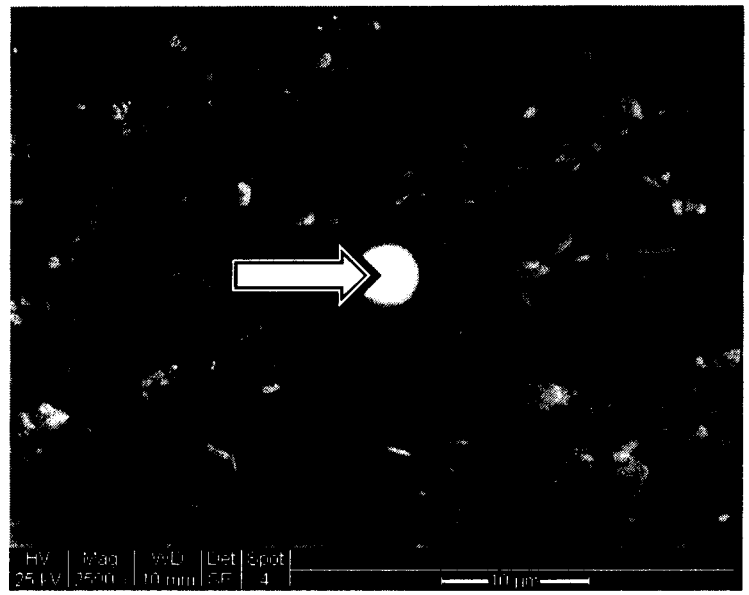
FIG. 4 shows an SEM image of an SGAN spheroid on an SEM stub coated by a first vapor deposition method with a sampled area in an embodiment of the invention.

The surface of the SEM stub was then viewed using a Philips® XL series XL 30 ESEM-FEG (FEI™ Company, Hillsboro, Oreg., United States), using EDAX® Genesis™ version 4.61 software (AMATEK® Inc., Mahwah, N.J., United States) and a Scandium Imaging Platform. The resulting electron microscope images of surfaces of the stub are shown in FIGS. 4 through 7. The accompanying elemental analysis by EDS for the sampled area (with the copper and aluminum readings from the stub itself being removed) showed only carbon, oxygen, and iron in the weight (wt %) and atomic (At %) percentages shown in Table 1 for the areas in the boxes sampled in FIGS. 4 through 7. FIGS. 4 through 6 show spheroid structures with diameters in the range of ~2-5 microns, and all of the figures show non-spheroid, irregularly-shaped structures with lengths in the range of ~1-5 microns.

TABLE 1

Synthesis Structure Elemental Analysis Data

Figure 5A:
FIG. 5A shows an SEM image of another SGAN spheroid on the SEM stub with a first sampled area.
Figure 5B:
FIG. 5B shows a second sampled area of the SGAN spheroid of FIG. 5A.
Figure 5C:
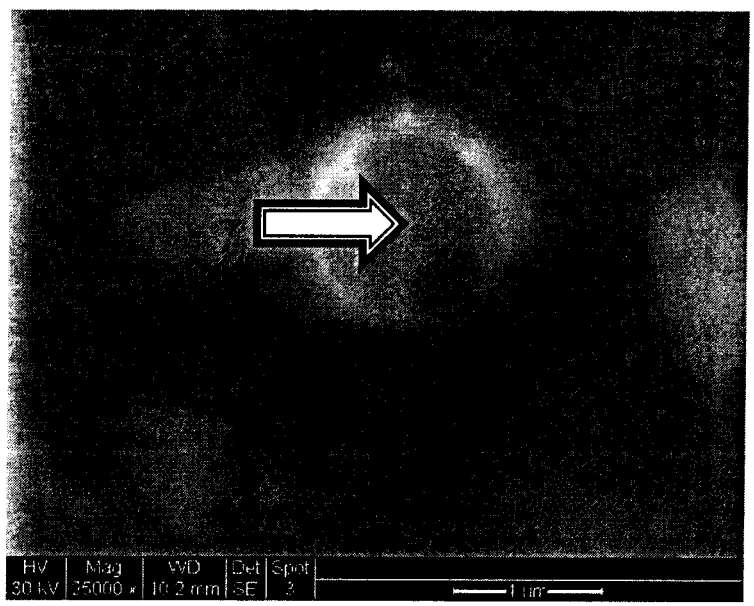
FIG. 5C shows a third sampled area of the SGAN spheroid of FIG. 5A.
Figure 6:
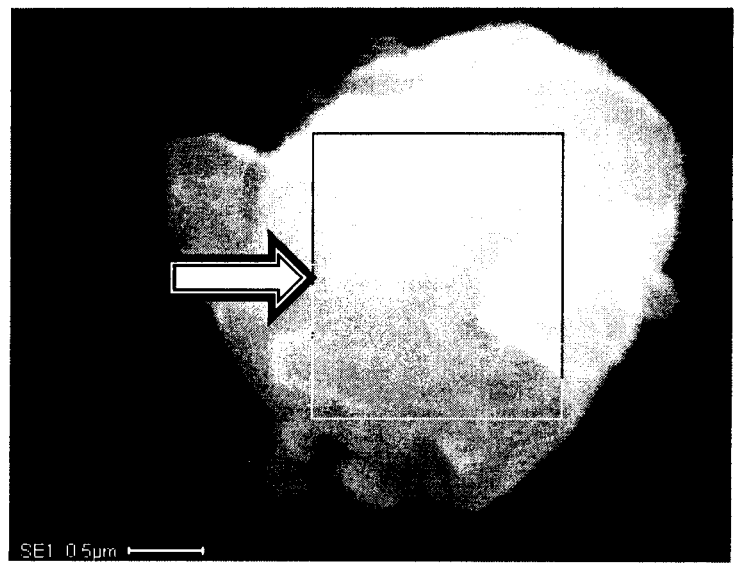
FIG. 6 shows an SEM image of a crystalline structure on the SEM stub with a sampled area in an embodiment of the invention.

| Sampled Area | C (wt %) | O (wt %) | Fe (wt %) | C (At %) | O (At %) | Fe (At %) |
|---|---|---|---|---|---|---|
| FIG. 4 | 69.96 | 28.94 | 1.09 | 76.11 | 23.64 | 0.26 |
| FIG. 5A | 78.79 | 19.65 | 1.56 | 83.93 | 15.71 | 0.36 |
| FIG. 5B | 74.72 | 24.11 | 1.17 | 80.28 | 19.45 | 0.27 |
| FIG. 5C | 79.04 | 19.51 | 1.45 | 84.09 | 15.58 | 0.33 |
| FIG. 6 | 34.19 | 55.07 | 10.74 | 43.92 | 53.11 | 2.97 |

The sampled areas of the spheroids of FIGS. 4 through 5C all show primarily carbon and oxygen with similar low values of iron. Referring specifically to FIG. 4, the EDAX® beam is aimed at a large area of a spheroid structure having a diameter of almost 5 µm. Referring specifically to FIG. 5A, the EDAX® point beam is aimed at a divot on the surface of a spheroid having a diameter between 2 and 3 µm. Referring specifically to FIG. 5B, the EDAX® beam is aimed at a small white area on the surface of the spheroid of FIG. 5A, with this image clearly showing the spheroid nature of the structure and the presence of surface imperfections. Referring specifically to FIG. 5C, the EDAX® beam is aimed on a wider portion of the spheroid of FIG. 5A. This structure is believed to contain significantly higher internal iron levels than those measured by EDS, with the low reading of iron by EDS indicating low EDAX® beam penetration of the outer shell into the spheroid cortex. The spheroid structures are believed to be multi-layer graphene oxide nano-onions, with the multiple graphene oxide layers shielding the internal iron from detection by EDS.

FIG. 6 shows the irregular structure of one of the non-spheroid features observed on the surface of the stub. The morphology of these structures is believed to be graphene oxide paper. The brighter areas of this image indicate higher concentrations of iron. The amount of iron in this structure, as measured by EDS, is almost ten times greater than what is measured in the spheroid structures. It is believed that the electron beam is able to penetrate this thin graphene oxide paper more than it is able to penetrate into the multi-layer spheroids, so that more iron is reported in this sample.

The observed spheroid structures were determined to be highly stable, as focusing of the EDAX® beam on the structure for more than 20 minutes had no observable effect on the structure.

In some SEM images, a square area of shade on the stem was observed, indicating electron excitation and a non-conductive surface, presumably coated with a graphene oxide film.

Test 2

In another method of synthesis of SGANs, a reaction mixture was heated using a direct flame. BayFerrox® iron oxide powder pigment (Lanxess, Cologne, Germany), powdered sugar, and gelled alcohol, in the form of a common hand sanitizer formulation including water, polyacrylic acid, and ~60% isopropyl alcohol, were placed in a reaction vessel and mixed together to form a reaction mixture. The reaction mixture was heated with the direct flame of a propane torch and an SEM stub was held above the heated reaction mixture in the smoke and/or vapor produced by heating the reaction mixture.

Figure 10:
FIG. 10 shows an SEM image of an area with numerous SGAN spheroids on the SEM stub.

The surface of the SEM stub was studied using a Philips® XL series XL 30 ESEM-FEG (FEI™ Company, Hillsboro, Oreg., United States), using EDAX® Genesis™ version 4.61 software (AMATEK® Inc., Mahwah, N.J., United States) and a Scandium Imaging Platform. The resulting electron microscope images of surfaces of the stub are shown in FIGS. 8 through 11. The accompanying elemental analysis by EDS (with the copper and aluminum readings from the stub itself being removed) showed only carbon (64.40 wt %/79.37 At %), oxygen (16.95 wt %/15.68 At %), and iron (18.65 wt %/4.94 At %) for the sampled area of FIG. 8. The observed structures on the SEM stub were generally smaller than those observed from the previous synthesis using ethanol rather than gelled alcohol. The number of spheroid structures in relation to flake structures was observed to be much higher than in the synthesis using ethanol. FIG. 10 shows an area of high concentration of spheroid structures.

Figure 11:
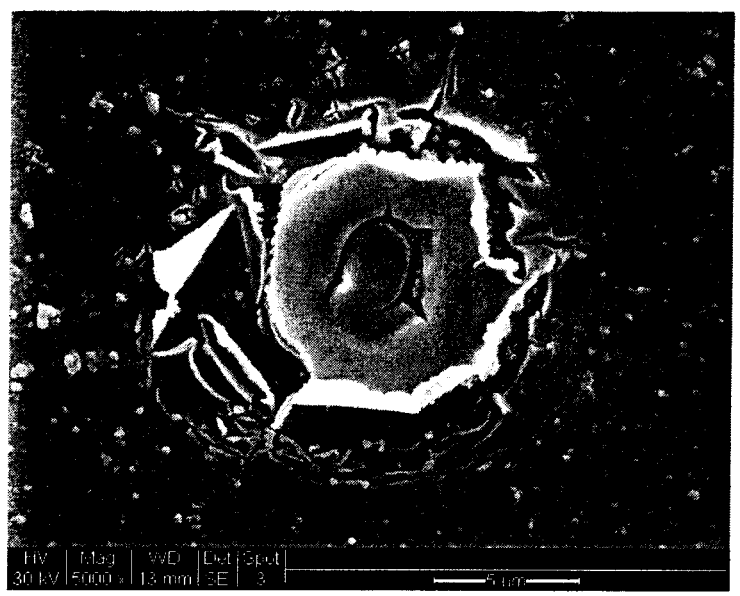
FIG. 11 shows an SEM image of a gold/palladium coated area of the SEM stub.

FIG. 11 shows a larger area of the SEM stub at a lower magnification. The image shows that a very thin film has been deposited continuously over a large area of the SEM stub. For imaging purposes, a gold/palladium coating was vapor-deposited onto the sample. The gold/palladium coating, however, was observed to be much thicker than the graphene oxide vapor coating, leading to the complete masking of any graphene oxide vapor coating detail by the gold/palladium coating. It is also significant to note that the gold/palladium coating shows that the graphene oxide vapor coating was unbroken on the whole stub.

Test 3

In another method of synthesis of SGANs, a reaction mixture was heated using a direct flame. BayFerrox® iron oxide powder pigment (Lanxess, Cologne, Germany), activated charcoal, methanol, and mineral oil were placed in a reaction vessel and mixed together to form a reaction mixture. The reaction mixture was heated with the direct flame of a propane torch and an SEM stub was held above the heated reaction mixture in the smoke and/or vapor formed from heating the reaction mixture.

The surface of the SEM stub was studied using a Philips® XL series XL 30 ESEM-FEG (FEI™ Company, Hillsboro, Oreg., United States), using EDAX® Genesis™ version 4.61 software (AMATEK® Inc., Mahwah, N.J., United States) and a Scandium Imaging Platform. The resulting electron microscope images of surfaces of the stub revealed structures similar in appearance to those from the above-described experiments, including spheroids in the range of 5-15 µm in diameter and larger irregular crystalline structures having minimum width dimensions in the range of 10-50 µm. The accompanying elemental analysis by EDS (with the copper and aluminum readings from the stub itself being removed) showed, in addition to carbon, oxygen, and iron, a number of impurities including calcium, copper, sodium, silicon, and lead, all of which can form face-centered cubic (FCC) crystals.

Test 4

In another method of synthesis of nanoparticles, a reaction mixture was heated using a hot plate to a lower temperature than in the previously described method using a direct flame. Iron oxide powder, powdered sugar, and ethanol were placed in a Büchner flask. The top of the flask was stoppered and plastic tubing was connected to the hose barb. The other end of the plastic tubing was placed under water in a beaker of distilled water. The reaction mixture was heated, causing vapor formation, which bubbled through the distilled water. After completion of the reaction, the water was allowed to evaporate slowly in the beaker, with the surface of the water having a gelatinous consistency and with a white residue being deposited on the walls of the beaker above the water surface as the water evaporated. Although the white residue was not characterized, it is believed to be made of SGANs.

Test 5

In another method of synthesis of nanoparticles, powdered sugar ("365 Organic Powdered Sugar" from Whole Foods Market, LP (Austin, Tex., United States). Ingredients: Organic Cane Sugar, Organic Tapioca Starch), hand sanitizer ("Instant Hand Sanitizer" from Greenbrier International, Inc. (Chesapeake, Va., United States). Ingredients: Ethyl Alcohol 62%, Water, Triethanolamine Glycerin, Proplyene Glycol, Tocopheryl Acetate, Aloe Barbadensis Gel, Carbomer, Fragrance), isopropanol ("99% Isopropyl Alcohol" from Meijer Distributing Inc. (Grand Rapids, Mich., United States)), baking powder ("Dr. Oetker Baking Powder" from Dr. Oetker Canada, Ltd. (Mississauga, Ontario, Canada). Ingredients: Sodium Acid Pyrophosphate, Sodium Bicarbonate, Corn Starch), and mineral oil ("Walgreens Mineral Oil Intestinal Lubricant" from Walgreen Co. (Deerfield, Ill., United States)) were combined in a flask. The flask was heated with a direct flame to convert the sugar to graphitic carbon. The top of the flask was stoppered and tubing directed the reaction gas stream containing the vapor-exfoliated graphene scales to bubble into a water bath. Mineral oil was added to the flask as needed to maintain liquid in the flask.

A metal spatula was contacted to the surface of the water bath to collect the reaction product which had formed there after being transported by the vapor stream. A visible film was observed on the metal spatula after the spatula was allowed to dry overnight. Although the metal spatula was dipped into the liquid at an angle, reaction product may alternatively be transferred to a solid surface by dipping the solid surface parallel or perpendicular to the liquid surface depending on the solid surface and the desired surface coating. Alternatively, the solid surface may be drawn up through the interface from below the liquid surface or by draining the liquid to deposit the product onto the solid surface in the liquid.

Figure 12:
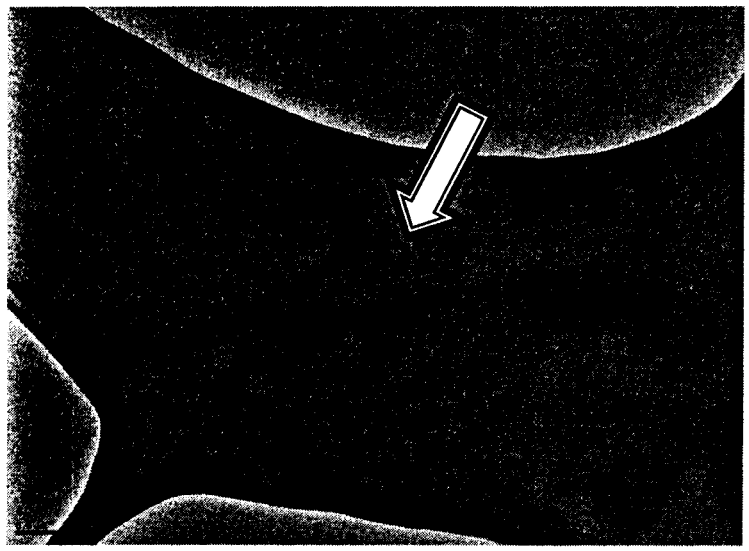
FIG. 12 shows a TEM image of a first area of a graphene product on a carbon TEM grid in an embodiment of the invention.
Figure 13:
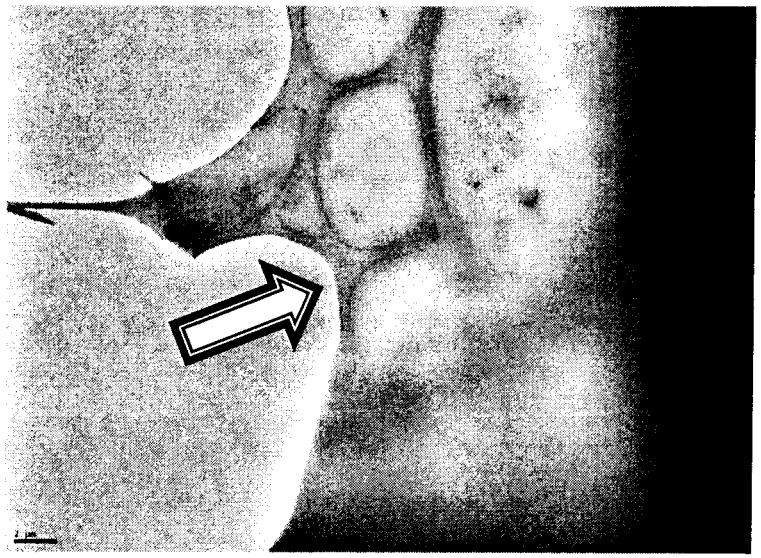
FIG. 13 shows a TEM image of a second area of the graphene product of FIG. 12.
Figure 14:
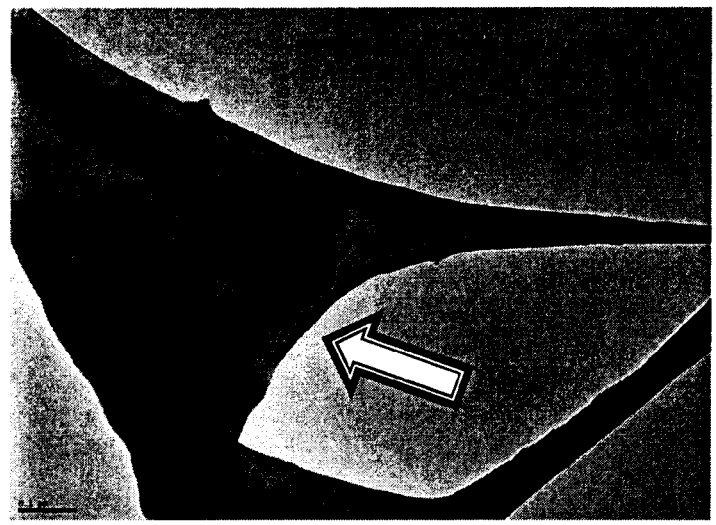
FIG. 14 shows a TEM image of a third area of the graphene product of FIG. 12.
Figure 15:
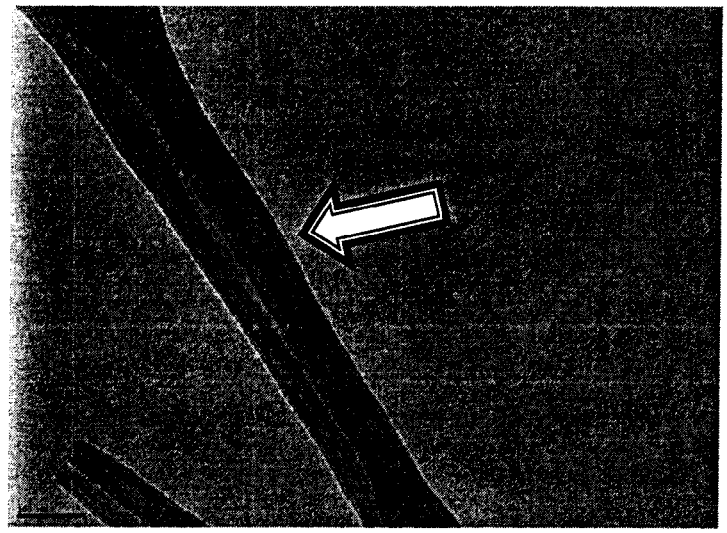
FIG. 15 shows a TEM image of a fourth area of the graphene product of FIG. 12.
Figure 16:
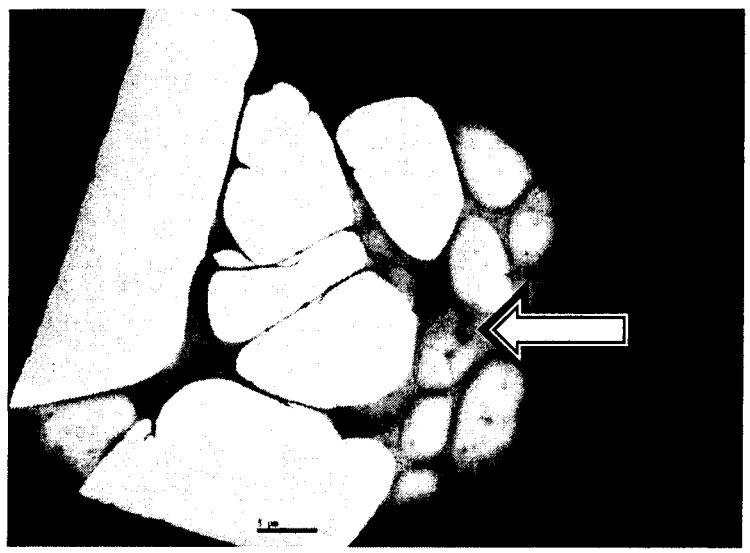
FIG. 16 shows a TEM image of a fifth area of the graphene product of FIG. 12.
Figure 17:
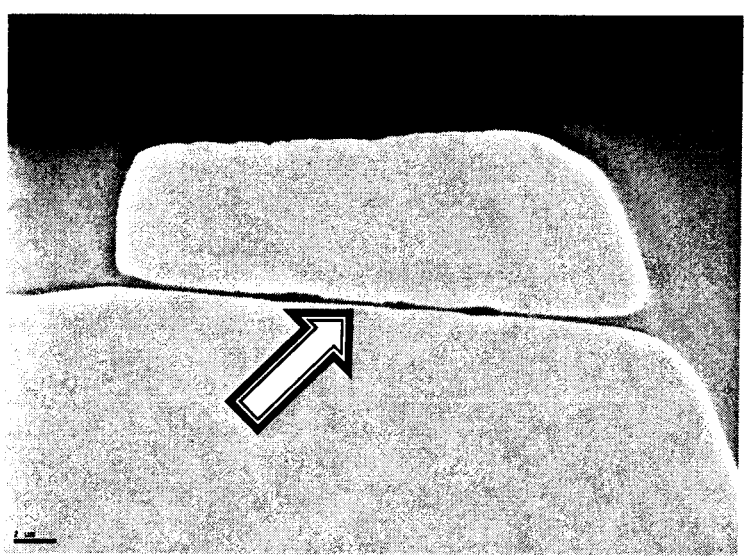
FIG. 17 shows a TEM image of a sixth area of the graphene product of FIG. 12.

The coated metal surface was then wiped against a carbon TEM grid to transfer some of the graphene coating to the TEM grid. The coating on the TEM grid was observed using a Philips® TEM (FEI™ Company, Hillsboro, Oreg., United States), serial number D609, and the images in FIGS. 12 through 17 were recorded. These structures are similar in composition and morphology to structures referred to as holey carbon or lacey carbon. FIG. 12 shows a fairly large, uniform graphene sheet morphology. FIG. 13 shows a large graphene sheet morphology with a tendril extending to the left of the image. FIG. 14 shows folded multilayer graphene sheets. FIGS. 16 and 17 show thin strands of graphene connecting larger sheet areas, with FIG. 15 showing a higher magnification of the multiple layers of such a strand. In addition to the images in FIGS. 12 through 17, portions of the TEM grid appeared completely black under the TEM, because the deposited layer was too thick for the electron beam to pass through. In several other areas, the film appeared not to be completely dry and the graphene coating was observed to change shape under the electron beam.

Test 6

In a method of forming graphene sheets, activated charcoal, water, mineral oil, and isopropanol were heated in a capped Büchner flask. As soon as the mixture began to boil and reflux, a white smoke began to be generated with the vapor. The whitish smoke was carried with the vapor out of the flask through plastic tubing and applied to the surface of an aqueous pool, where an opaque film formed on the surface.

After waiting several minutes after the film had formed, portions of the film were transferred to copper TEM grids for further study.

Figure 18:
FIG. 18 shows a TEM image of an area of a graphene product on a copper TEM grid in an embodiment of the invention.
Figure 19:
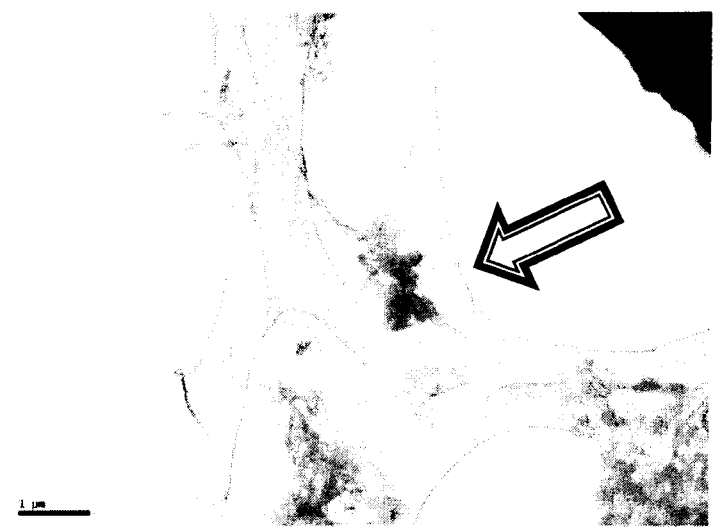
FIG. 19 shows a TEM image of an area of another graphene product on a copper TEM grid in an embodiment of the invention.

The copper TEM grids were studied using a Philips® Tecnai F20 (S)TEM (FEI™ Company, Hillsboro, Oreg., United States). Representative images of the samples are shown in FIGS. 18 and 19. For elemental analysis, the EDAX® beam was used to determine the carbon-to-oxygen ratios at eight different points in the sample. The resulting analysis showed that the carbon-to-oxygen ratio in the samples was between 97.4:2.6 atomic % to 99.1:0.9 atomic % with an average of 98.4:1.6 atomic % from the eight samples. In comparison to the experiments with iron oxide in the reaction mixture, in the absence of iron oxide the resulting product was almost pure carbon in the form of graphene.

In Situ Production of Tribologically-Effective Amounts of Beneficial Carbonaceous Deposits in Lubricating Compositions.

Embodiments of the invention employ cyclic-carbon containing additives for base lubricants intended to pyrolyze quickly in situ and produce tribologically-effective amounts of beneficial carbonaceous deposits and molecules within an engine or mechanical system. In one embodiment, the additive forms beneficial abrasive graphitic particles in situ in the lubrication composition that serve as nanopolishing agents to nano-polish friction surfaces and remove asperities before the base lubricant begins to degrade significantly. Once the friction surfaces are nano-polished to near atomic-level perfection, there are no longer asperities on the friction surfaces to harbor harmful deposits. Thus, harmful deposit formation on internal system parts and the need for conventional detergent additives in lubricating compositions are drastically reduced or even eliminated.

The additives disclosed herein are not selected to improve or protect the underlying base lubricant. Instead, the additives are selected to promote rapid in situ preferential formation of polycyclic aromatic hydrocarbons or other graphitic carbon forms that are tribologically-useful graphitic carbon-containing nanoparticles or microparticles in tribologically-effective amounts. In one embodiment, the additive includes a carbon ring-containing additive consisting of only carbon, hydrogen, and oxygen atoms. In one embodiment, the carbon ring-containing additive is a hydrocarbon. Any radicals in the lubricating composition preferably aid in the formation of the useful graphitic carbon particles. In one embodiment, the nanoparticles act as nano-polishing agents to nano-polish friction surfaces to a high smoothness by reduction or removal of asperities, thereby reducing the friction between the wear surfaces. Over time, conventional base lubricants tend to lose viscosity, putting friction surfaces at risk for damage. With use of embodiments of the current invention, friction surfaces become increasingly nano-polished, so any thinning of the base lubricant through continued use actually allows the mechanical system to run more efficiently through reduction in the viscosity of the base lubricant. In one embodiment, the base lubricant starts as a heavier weight oil and progressively thins to a lighter weight oil over time as the friction surfaces become nano-polished. In one embodiment, the lubricating composition effectively lubricates despite extended drain or replacement intervals as compared to conventional base lubricants.

Instead of promoting degradation over time to form compounds that turn into amorphous carbon sludge, at least one of the additives preferentially promotes formation of one or more tribologically-useful graphitic carbon forms described herein.

Lubricating compositions of the present invention preferably include an additive selected to serve as a sacrificial carbon source for in situ formation of graphitic carbon, while the base lubricant continues to lubricate an operating engine or other mechanical system. The base lubricant may be a petroleum-refined or a synthetic oil, grease or liquid. The additive can be pyrolyzed to form graphitic carbon under the conditions of the operating engine or other mechanical system. In one embodiment, the additive can be pyrolyzed at a temperature of between ~50° C. and ~550° C. In one embodiment, the additive can be pyrolyzed at a temperature less than ~50° C. or a temperature greater than ~550° C. In an operating engine, such conditions may be reached locally at friction surfaces or on internal engine, turbo, turbine or gear surfaces.

The additive is provided in a tribologically-effective amount such that in situ structures are formed and present in the lubricating composition to initially provide a sufficiently efficacious tribological coating on the friction surfaces of a lubricated system. The amount of additive to be added to the lubricant can be varied according to the desired rate of change of performance of the operating engine or other mechanical system, and the quantity of base lubricant to remain undiluted. Addition of a higher amount of additive increases the rate of formation of the in situ structures but will also dilute the base lubricant. An effective amount of additive may therefore comprise from ~10 mg per liter of base lubricant to ~500 g per liter of base lubricant. These amounts are not intended to limit the invention in any manner and can be determined on a case by case basis by the formulator.

In one embodiment, the tribologically-effective amount of additive decreases friction in the lubricated system relative to lubrication by the conventional lubricant to which it is added. In one embodiment, the tribologically-effective amount of additive decreases friction in the lubricated system by at least 1% relative to lubrication by the conventional lubricant to which it is added. In one embodiment, the tribologically-effective amount of additive decreases friction in the lubricated system by at least 2% relative to lubrication by the conventional lubricant to which it is added. In one embodiment, the tribologically-effective amount of additive decreases friction in the lubricated system by at least 3% relative to lubrication by the conventional lubricant to which it is added. In one embodiment, the tribologically-effective amount of additive decreases friction in the lubricated system by at least 4% relative to lubrication by the conventional lubricant to which it is added. In one embodiment, the tribologically-effective amount of additive decreases friction in the lubricated system by at least 5% relative to lubrication by the conventional lubricant to which it is added. In one embodiment, the tribologically-effective amount of additive decreases friction in the lubricated system by at least 10% relative to lubrication by the conventional lubricant to which it is added.

In one embodiment, a tribologically-effective amount of additive decreases negative horsepower in the lubricated system relative to lubrication by the conventional lubricant to which it is added. In one embodiment, the tribologically-effective amount of additive increases measured horsepower in the lubricated system by at least 1% relative to lubrication by the conventional lubricant to which it is added. In one embodiment, the tribologically-effective amount of additive increases measured horsepower in the lubricated system by at least 2% relative to lubrication by the conventional lubricant to which it is added. In one embodiment, the tribologically-effective amount of additive increases measured horsepower in the lubricated system by at least 5% relative to lubrication by the conventional lubricant to which it is added. In one embodiment, the tribologically-effective amount of additive increases measured horsepower in the lubricated system by at least 10% relative to lubrication by the conventional lubricant to which it is added. In one embodiment, the tribologically-effective amount of additive increases measured horsepower in the lubricated system by at least 20% relative to lubrication by the conventional lubricant to which it is added. In one embodiment, the tribologically-effective amount of additive increases measured horsepower in the lubricated system by at least 50% relative to lubrication by the conventional lubricant to which it is added.

In one embodiment, a tribologically-effective amount of additive increases torque output in the lubricated system relative to lubrication by the conventional lubricant to which it is added. In one embodiment, the tribologically-effective amount of additive increases torque output in the lubricated system by at least 1% relative to lubrication by the conventional lubricant to which it is added. In one embodiment, the tribologically-effective amount of additive increases torque output in the lubricated system by at least 2% relative to lubrication by the conventional lubricant to which it is added. In one embodiment, the tribologically-effective amount of additive increases torque output in the lubricated system by at least 5% relative to lubrication by the conventional lubricant to which it is added. In one embodiment, the tribologically-effective amount of additive increases torque output in the lubricated system by at least 10% relative to lubrication by the conventional lubricant to which it is added. In one embodiment, the tribologically-effective amount of additive increases torque output in the lubricated system by at least 20% relative to lubrication by the conventional lubricant to which it is added. In one embodiment, the tribologically-effective amount of additive increases torque output in the lubricated system by at least 50% relative to lubrication by the conventional lubricant to which it is added.

In one embodiment, a tribologically-effective amount of additive decreases the surface roughness of an internal friction surface in the lubricated system relative to lubrication by the conventional lubricant to which it is added. In one embodiment, the tribologically-effective amount of additive decreases the surface roughness of an internal friction surface in the lubricated system by at least 5% relative to lubrication by the conventional lubricant to which it is added. In one embodiment, the tribologically-effective amount of additive decreases the surface roughness of an internal friction surface in the lubricated system by at least 10% relative to lubrication by the conventional lubricant to which it is added. In one embodiment, the tribologically-effective amount of additive decreases the surface roughness of an internal friction surface in the lubricated system by at least 20% relative to lubrication by the conventional lubricant to which it is added. In one embodiment, the tribologically-effective amount of additive decreases the surface roughness of an internal friction surface in the lubricated system by at least 50% relative to lubrication by the conventional lubricant to which it is added. In one embodiment, the tribologically-effective amount of additive decreases the surface roughness of an internal friction surface in the lubricated system by at least 75% relative to lubrication by the conventional lubricant to which it is added. In one embodiment, the tribologically-effective amount of additive decreases the surface roughness of an internal friction surface in the lubricated system by at least 90% relative to lubrication by the conventional lubricant to which it is added.

In one embodiment, the measurable change in friction, reduction in negative horsepower, or reduction in surface roughness occurs within 100 operating hours of the lubricated system after adding the tribologically-effective amount of the additive. In one embodiment, the measurable change in friction, reduction in negative horsepower, or reduction in surface roughness occurs within 80 operating hours of the lubricated system after adding the tribologically-effective amount of the additive. In one embodiment, the measurable change in friction, reduction in negative horsepower, or reduction in surface roughness occurs within 60 operating hours of the lubricated system after adding the tribologically-effective amount of the additive. In one embodiment, the measurable change in friction, reduction in negative horsepower, or reduction in surface roughness occurs within 40 operating hours of the lubricated system after adding the tribologically-effective amount of the additive. In one embodiment, the measurable change in friction, reduction in negative horsepower, or reduction in surface roughness occurs within 20 operating hours of the lubricated system after adding the tribologically-effective amount of the additive. In one embodiment, the measurable change in friction, reduction in negative horsepower, or reduction in surface roughness occurs within 10 operating hours of the lubricated system after adding the tribologically-effective amount of the additive. In one embodiment, the measurable change in friction, reduction in negative horsepower, or reduction in surface roughness occurs within 5 operating hours of the lubricated system after adding the tribologically-effective amount of the additive. In one embodiment, the measurable change in friction, reduction in negative horsepower, or reduction in surface roughness occurs within 2 operating hours of the lubricated system after adding the tribologically-effective amount of the additive. In one embodiment, the measurable change in friction, reduction in negative horsepower, or reduction in surface roughness occurs within one operating hour of the lubricated system after adding the tribologically-effective amount of the additive. In one embodiment, the measurable change in friction, reduction in negative horsepower, or reduction in surface roughness occurs within 30 operating minutes of the lubricated system after adding the tribologically-effective amount of the additive. In one embodiment, the measurable change in friction, reduction in negative horsepower, or reduction in surface roughness occurs within 10 operating minutes of the lubricated system after adding the tribologically-effective amount of the additive. In one embodiment, the measurable change in friction, reduction in negative horsepower, or reduction in surface roughness occurs within 5 operating minutes of the lubricated system after adding the tribologically-effective amount of the additive. In one embodiment, the measurable change in friction, reduction in negative horsepower, or reduction in surface roughness occurs substantially instantaneously after adding the tribologically-effective amount of the additive.

Lubricating compositions including at least one additive, as described, improve engine performance and nano-polish lubricated metal surfaces. At least one of the additives is chemically modified in situ to form lubricating and nano-polishing particles, which have been observed on lubricated metal surfaces both by scanning electron microscopy (SEM) and transmission electron microscopy (TEM). Observed spheroid structures on non-friction surfaces are generally in the 1-10 micron size range and are determined to be made primarily of carbon, oxygen, and iron. These microparticle structures are separated down to a basic particle no larger than ~3 nm in dimension and hard enough to nano-polish steel surfaces to the measured surface roughness ($R_a$) of 3.44 nm.

For one embodiment, this basic particle has been analytically determined to be an SGAN and, more specifically, a metallic SGAN. In some embodiments, the metallic SGAN is a ferric SGAN. The core of the SGAN can be a cubic close-packed crystal structure with a face-centered cubic metal. The cubic close-packed crystal can be of a metal oxide of the spinel family, which may include, but is not limited to, magnetite ($Fe_3O_4$), spinel ($MgAl_2O_4$), gahnite ($ZnAl_2O_4$), hercynite ($FeAl_2O_4$), cuprospinet ($CuFe_2O_4$), franklinite, galaxite, jacobsite ($MnFe_2O_4$), trevorite ($NiFe_2O_4$), ulvöspinet ($TiFe_2O_4$), zinc ferrite, chromite ($FeCr_2O_4$), and magnesiochromite ($MgCr_2O_4$). In other embodiments, the core can be a non-spinel cubic crystal structure.

The cubic crystal structure can include at least one iron atom. In some embodiments, the crystal core can be ferric hydroxide in spinel form (Belleville et al., "Crystallization of ferric hydroxide into spinel by adsorption on colloidal magnetite", *Journal of Colloid and Interface Science*, Vol. 150, pp. 453-460, 1992). In one embodiment, the crystal core can be $Fe_xCu_{1-x}Rh_2Se_4$, where $0<x\leq0.3$, in spinel form (Kim et al., "Magnetic properties of the spinel phase for $Fe_xCu_{1-x}Rh_2Se_4$", *J. Appl. Phys.*, Vol. 64, 342190, 1988).

In one embodiment, the crystal core forms in situ. In one embodiment, the additive includes a crystal core. In some embodiments, the crystal core can be formed by one or more mechanisms described by Dekker ("Chapter 5: Deoxidation in Low Carbon Steel Killed with Aluminum" in Ph.D. Thesis, Katholieke Universiteit Leuven, Leuven, pp. 43-65, Belgium, 2002), Botta et al. ("Mechanochemical synthesis of hercynite", *Materials Chemistry and Physics*, Vol. 76, pp. 104-109), or Chen et al. ("Synthesis of hercynite by reaction sintering", *Journal of the European Ceramic Society*, Vol. 31, pp. 259-263, 2011).

In one embodiment, the shell of the SGAN is believed to be a carbon fullerene or fullerene-like structure. In some embodiments, the carbon source is believed to be converted to PAHs in situ as disclosed by Bohme ("PAH and Fullerene Ions and Ion/Molecule Reactions in Interstellar and Circumstellar Chemistry", *Chem. Rev.*, Vol. 92, pp. 1487-1508, 1992), Mansurov ("Formation of Soot from Polycyclic Aromatic Hydrocarbons as well as Fullerenes and Carbon Nanotubes in the Combustion of Hydrocarbon", *Journal of Engineering Physics and Thermodynamics*, Vol. 84, pp. 125-159, 2011), or Ravindra et al. ("Atmospheric polycyclic aromatic hydrocarbons: Source attribution, emission factors and regulation", *Atmospheric Environment*, Vol. 42, pp. 2895-2921, 2008) to form graphene sheets, wherein the graphene is then converted to a fullerene in the presence of iron by a mechanism such as the one disclosed by Chuvilin et al. ("Direct transformation of graphene to fullerene", *Nature Chemistry*, Vol. 2, pp. 450-453, 2010). In one embodiment, the carbon deposits on the surface of an iron particle are believed to be in the form of coke such as disclosed by Meima et al. ("Catalyst deactivation phenomena in styrene production", *Applied Catalysis A: General*, Vol. 212, pp. 239-245, 2001). In one embodiment, the SGAN is believed to be surface graphitized.

In one embodiment, the carbon may be deposited on the surface of an iron particle in the form of a cross-linked styrene sphere, such as the process of Friedel-Crafts alkylation, cross-linking and polymerization described by Barar et al. ("Freidel-Crafts Cross-Linking for Polystyrene Modification", *Ind. Eng. Chem. Prod. Res. Dev.*, Vol. 22, pp. 161-166, 1983).

In the observed SGANs, at least some of the measured iron is expected to be in the form of magnetite, which would make SGANs ferrimagnetic. In other embodiments, the SGAN or crosslinked styrene spheres may include one or more ferromagnetic, paramagnetic, or superparamagnetic particles. In one embodiment, the SGANs are believed to form in situ, agglomerate, and are coated with graphitic carbon in the form of one or any combination of polycyclic aromatic hydrocarbons (PAHs), graphene, graphene oxide (GO), microtubule, and fullerene to form larger microparticles. Under sheer, these agglomerates are believed to break down into smaller units or shed surface layers but re-agglomerate once removed from the high-sheer environment.

The magnetic nature of the SGANs or iron-containing crosslinked styrene spheres makes them attractive to each other, to graphitic carbon, and to iron-containing surfaces and iron-containing particles suspended in the lubricating composition. When a ferric SGAN or larger aggregate nears a steel friction surface, the particle would then be attracted to the surface and serve both to aid in lubrication and to micropolish the friction surface. The core supporting the shell of the SGAN would provide the strength required to polish steel parts.

The disclosed SGANs are superior nano-polishers to nano-diamonds. Since the core of the SGAN is not believed to be chemically bonded to its shell, the shell is believed to be able to spin independently of the core, so as to act as a nano-ball bearing. Additionally, the unbound shell of the SGAN is believed to be less rigid than nanodiamond and thus more able to diffuse impact forces.

In one embodiment, rather than the crystalline metal-containing cores described above, the SGAN may have an aromatic carbon ring-containing core. In one embodiment, the aromatic carbon ring-containing core may be a styrene- or styrene derivative-containing core. In one embodiment, the aromatic carbon ring-containing core may form in situ in the lubricating composition by self-assembly of aromatic carbon ring-containing amphiphilic molecules. In one embodiment, the aromatic carbon ring-containing amphiphilic molecules may be styrene or styrene derivative amphiphilic molecules. In one embodiment, the self-assembled core may contain reactive groups that allow the molecules to chemically cross-link to each other once self-assembled. In one embodiment, a fullerene shell may form around the self-assembled core to form a nanoparticle similar to the above-described SGANs to form a nano-polishing agent.

In addition to the tested additives, many other classes of additives may be used in lubricating compositions to achieve similar results. The additive preferably has a structure with at least one cyclic ring, which may be aromatic or non-aromatic, and at least one functional group extending from the ring or from a chain extending from the ring. In one embodiment, the structure includes fused rings. The additive preferably has a structure including at least one oxygen atom in addition to carbon and hydrogen. In one embodiment, other heteroatoms may be present in the chemical structure, although they may not be required to achieve the desired results and may be disfavored.

In one embodiment, the additive is dissolved in the lubricating composition. In one embodiment, the additive is a liquid that is miscible with the lubricant. In one embodiment, the additive includes a particulate. Since conventional engine oil filters are designed to filter out substantially all particles greater than ~40 μm in size, about half of the particles ~20 μm in size, and about 10-20% of particles ~10 μm in size, the particulate additives to the engine oil preferably have an average particle size less than ~10 μm to prevent clogging of an oil filter. In one embodiment, substantially all of the particles have a size less than ~10 μm. In one embodiment, the particulate additives have an average particle size less than ~5 μm. In one embodiment, substantially all of the particles have a size less than ~5 μm. In one embodiment, the particulate additives have an average particle size less than ~1 μm. In one embodiment, substantially all of the particles have a size less than ~1 μm.

In one embodiment, the additive comprises powdered sugar (sucrose). Powdered sugars are commercially available in a variety of fineness and are commonly used for baking. 6× powdered sugars have an average particle size of less than ~200 μm. 10× powdered sugars have an average particle size of less than ~150 μm. Fondant sugars are powdered sugars with an average particle size under ~50 μm. Commercially available fondant sugars include "Celebration" (British Sugar, Peterborough, UK, Great Britan), a superfine sugar with an average particle size of ~11 μm, "Silk Sugar" (British Sugar, Peterborough, United Kingdom, Great Britain), an ultrafine sugar with an average particle size of ~8 μm, and C&H Baker's Drivert (C&H Sugar Company, Inc., Crockett, Calif., United States) with an average particle size of ~5-7 μm.

In one embodiment, the powdered sugar has an average particle size less than ~5 μm. In one embodiment, substantially all of the particles have a size less than ~5 μm. In some embodiments, the powdered sugar has an average particle size less than ~1 μm. In one embodiment, substantially all of the particles have a size less than ~1 μm. In one embodiment, the powdered sugar is formed to the predetermined particle size by grinding crystalline sucrose in a dry environment. In one embodiment, the powdered sugar is ground using a known dry micro-milling technique of grinding crystals to micron or sub-micron particle sizes. In one embodiment, the powdered sugar is formed to the predetermined particle size by evaporative techniques such as evaporation of solvent from microdroplets of a dissolved sugar solution or lyophilization (freeze-drying) of a dissolved sugar solution.

In one embodiment, sugar, preferably micro-powdered or nano-powdered sucrose, is added to a conventional lubricating fluid to serve as the carbon source for in situ formation of graphitic carbon while the lubricating composition lubricates an operating engine. In one embodiment, only sugar is added to a conventional base lubricant. In one embodiment, sugar and Marvel Mystery Oil (original formula, Turtle Wax, Inc., Westmont, Ill., United States, naphthenic hydrocarbon and terpene source) are added to a conventional base lubricant. In one embodiment, sugar and mineral oil are added to a conventional base lubricant. In one embodiment, sugar is combined with an oil surfactant to compatibilize the sugar prior to addition to the base lubricant (see Hiteshkumar et al., "Self-assembly in sugar-oil complex glasses", *Nature Materials*, 6, pp. 287-290, 2007). In one embodiment, compatibilization of the sugar prevents the sugar from clogging a filter in the lubricated system as a gel or solid. In one embodiment, the oil surfactant is a terpene. In one embodiment, the terpene is limonene. In one embodiment, the sugar and oil surfactant are combined in a ratio less than about 1:1. In one embodiment, the sugar-oil surfactant mixture is in a liquid state at the time of being added to the lubricating fluid. In one embodiment, the sugar is a sugar amphiphile.

In one embodiment, the additive comprises a pyranose, a furanose, a cyclic carbomer, or a benzenoid (see Katritzky et al., "Aqueous High-Temperature Chemistry of Carbo- and Heterocycles. 20.[1] Reactions of some Benzenoid Hydrocarbons and Oxygen-Containing Derivatives in Supercritical Water at 460° C.", *Energy & Fuels*, Vol. 8, pp. 487-497, 1994), including, but not limited to, oxygen-containing benzenoids.

In one embodiment, the additive comprises a sugar other than sucrose. In one embodiment the sugar comprises a molasses or molasses substitute, which may comprise, but is not limited to, sweet sorghum, sugar beet molasses, pomegranate molasses, mulberry molasses, carob molasses, date molasses, grape molasses, backstrap molasses, black treacle, bee's honey, maple syrup, or corn syrup, including, but not limited to, high-fructose corn syrup. In some embodiments, the sugar comprises an invert sugar, which may comprise, but is not limited to, inverted sugar syrup.

In one embodiment, the sugar comprises a deoxy sugar, which may comprise, but is not limited to, deoxyribose, fucose, or rhamnose.

In one embodiment, the sugar comprises a monosaccharide, which may comprise, but is not limited to, glucose, fructose, galactose, xylose, or ribose.

In one embodiment, the sugar comprises a disaccharide, which may comprise, but is not limited to, sucrose, lactulose, lactose, maltose, trehalose, cellobiose, or sophorose.

In one embodiment, the sugar comprises a polysaccharide, which may comprise, but is not limited to, starch, glycogen, arabinoxylan, cellulose, chitin, or pectin.

In one embodiment, the additive comprises a sugar alcohol, which may include, but is not limited to, erythritol, threitol, arabitol, xylitol, ribitol, mannitol, sorbitol, dulcitol, iditol, isomalt, maltitol, or lactitol.

In one embodiment, the additive comprises a sugar substitute, which may include, but is not limited to, stevia, aspartame, sucralose, neotame, acesulfame potassium, or saccharin.

In one embodiment, the additive comprises a sugar derivative, which may include, but is not limited to, sophoritol, a phenolic glycoside, a steviol glycoside, a saponin, a glycoside, a glucoside, or amygdalin.

In one embodiment, the additive comprises a cyclomethicone, which may include, but is not limited to, phenyl trimethicone or cyclopentasiloxane.

In one embodiment, the additive comprises a steroid, which may include, but is not limited to, sapogenin or diosgenin.

In one embodiment, the additive comprises a cinnamate, which may include, but is not limited to, methyl or ethyl cinnamate. In one embodiment, the additive comprises cinnamic acid. In one embodiment, the additive comprises cinnamon oil.

In one embodiment, the additive comprises a phenylphopanoid, which may include, but is not limited to, cinnamic acid, coumaric acid, caffeic acid, ferulic acid, 5-hydroxyferulic acid, sinapic acid, cinnamaldehyde, umbelliferone, resveratrol, a monolignol, which may comprise, but is not limited to, coniferyl alcohol, coumaryl alcohol, or sinapyl alcohol, or a phenylpropene, which may comprise, but is not limited to, engenol, chavicol, safrole, or estragole.

In one embodiment, the additive comprises a benzoate, which may include, but is not limited to, ferric, benzyl, ethyl, methyl, phenyl, cyclohexanol, 2-phenyl-, pentaerythritol tetra-, sodium, or potassium benzoate. In one embodiment, the additive includes benzoic acid. In some embodiments, the additive comprises aminobenzoic acid. In one embodiment, the additive comprises 2-hydroxymethyl benzoic acid methyl ester. In one embodiment, the additive includes ubiquinone.

In one embodiment, the additive comprises a carboxylate, including but not limited to trimethyl cis, cis-1,3,5-cyclohexanetricarboxylate.

In one embodiment, the additive comprises a benzopyran, which may include, but is not limited to, chromene, isochromene, or a substituted benzopyran.

In one embodiment, the additive comprises a naturally-occurring or synthetic flavone or isoflavone, which may include, but is not limited to, flavan-3-ol or flavanone.

In one embodiment, the additive comprises a salicylate, which may include, but is not limited to, ferric, methyl, ethyl, butyl, cinnamyl, cyclohexyl, ethylhexyl, heptyl, isoamyl, octyl, benzyl, phenyl, p-cresol, o-cresol, m-cresol, or sodium salicylate. In one embodiment, the additive includes salicylic acid. In one embodiment, the additive includes aminosalicylic acid.

In one embodiment, the additive comprises an antioxidant. In one embodiment, the antioxidant is a cyclic antioxidant. In one embodiment, the antioxidant is a phenolic antioxidant, which may include, but is not limited to, 2,6-di-terti-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-1-butylphenol, 2,6-di-cyclopentyl-4-methylphenol, 2-(α-methylcyclohexyl)-4,6-dimethylphenol, 2,6-di-octadecyl-methylphenol, 2,4,6-tri-cyclohexylphenol, 2,6-di-tert-butyl-4-methoxymethylphenol, 2,6-di-tert-butyl-4-methoxyphenol, 2,5-di-tert-butyl-hydroquinone, 2,5-di-tert-amyl-hydroquinone, 2,6-diphenyl-4-octadecyloxyphenol, 2,2'-methylene-bis-(6-tert-butyl-4-methylphenol), 2,2'-methylene-bis-(6-tert-butyl-4-ethylphenol), 2,2'-methylene-bis-[4-methyl-6-α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-[6-α-methylbenzyl)-4-nonylphenol], 2,2'-methylene-bis [6-(α,α-dimethylbenzyl)-4-nonylphenol], 2,2'-methylene-bis-(4,6-di-tert-butylphenol), 2,2'-ethylidene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-di-(3-tert-butyl-5-methyl-2-hydroxybenzyl)-4-methylphenol, 1,1,3-tris-(5-tert-butyl-4-hydroxy-2-methylphenyl)-butane, and any naturally-occurring plant-based phenolic antioxidant, which may include, but is not limited to, ascorbic acid, a tocopherol, a tocotrienol, rosemarinic acid, and other phenolic acids and flavonoids, such as those found, for example, in grapes, berries, olives, soy, tea leaves, rosemary, basil, oregano, cinnamon, cumin, and turmeric.

In one embodiment, the additive comprises 4-vinylphenol, anthocyanidin, or chromenylium.

In one embodiment, the additive comprises a cyclic amino acid, which may include, but is not limited to, phenylalanine, tryptophan, or tyrosine.

In one embodiment, the additive comprises a cyclohexane derivative, which may include, but is not limited to, 1,3-cyclohexadiene or 1,4-cyclohexadiene.

In one embodiment, the additive comprises a benzene derivative which may include, but is not limited to, a polyphenol, benzaldehyde, benzotriazole, benzyl 1-naphthyl carbonate, benzene, ethyl benzene, toluene, styrene, benzonitrile, phenol, phthalic anhydride, phthalic acid, terephthalic acid, p-toluic acid, benzoic acid, aminobenzoic acid, benzyl chloride, isoindole, ethyl phthalyl ethyl glycolate, N-phenyl benzamine, methoxybenzoquinone, benzylacetone, benzylideneacetone, hexyl cinnamaldehyde, 4-amino-2-hydroxytoluene, 3-aminophenol, or vanillin.

In one embodiment, the benzene derivative additive comprises a benzenediol, which may include 1,2-dihydroxybenzene (catechol), 1,3-dihydroxybenzene (resorcinol), or 1,4-dihydroxybenzene (hydroquinone).

In one embodiment, the additive comprises a naphthoate, including but not limited to methyl 2-methoxy-1-naphthoate or methyl 3-methoxy-2-naphthoate.

In one embodiment, the additive comprises an acrylate, including but not limited to benzyl 2-propylacrylate or 2-naphthyl methacrylate.

In one embodiment, the additive comprises a phthalate, including but not limited to diallyl phthalate.

In one embodiment, the additive comprises a succinate, including but not limited to bis(2-carboxyphenyl) succinate.

In one embodiment, the additive comprises a carpate, including but not limited to methyl O-methylpodocarpate.

In one embodiment, the additive comprises a fluorophore, which may include, but is not limited to, fluorescein isothiocyanate, rhodamine, phthalocyanine, or copper phthalocyanine.

In one embodiment, the additive comprises a pharmaceutical, which may include, but is not limited to, acetylsalicylic acid, acetaminophen, ibuprofen, or a benzodiazepine.

In one embodiment, the additive comprises a phosphate, which may include, but is not limited to, a cresyldiphenyl phosphate, a dicresyl phosphate, a triorthocresyl phosphate, a tricresyl phosphate, a paracresyl phosphate, an orthocresyl phosphate, or a metacresyl phosphate.

In one embodiment, the additive comprises a compound that degrades to one or more of the above-mentioned additives under the heat of the operating conditions of the engine or mechanical system, such as certain terpenes or certain natural aromatic or non-aromatic cyclic esters, ketones, or aldehydes, which may include, but is not limited to, methyl salicylate (wintergreen oil), cinnamon leaf/bark oil (cinnamaldehyde), limonene (dipentene), pinene, and camphene.

In one embodiment, the additive comprises a commercial edible personal/sexual lubricating composition including a sugar or sugar-substitute amphiphile.

In one embodiment, the additive comprises a commercial ultraviolet ray sunscreen formulation, which may include octyl methoxycinnamate (oxtinoxate), butyl-methoxy-dibenzoylmethane (B-MDM, Avobenzone), octyl-dimethyl-para-aminobenzoic acid (OD-PABA), octocrylene, oxybenzone, alkyl benzoate, diethylhexyl 2,6-naphthalate, phenoxyethanol, homosalate, ethylhexyl triazone, 4-methylbenzylidene camphor (4-MBC), or a polysorbate.

In one embodiment, the additive comprises a commercial skin cream formulation, which may include, but is not limited to carbomer, ascorbyl palmitate, tocopheryl acetate, ketoconazole, or mineral oil.

In one embodiment, the additive comprises a commercial hand sanitizer formulation, which may include carbomer, tocopheryl acetate, or propylene glycol.

In one embodiment, the additive comprises a commercial human or animal hair care product, which may include benzophenone, alkyl benzoate, phenoxyethanol, sorbitan oleate, a styrene copolymer, propylene glycol, hydroxyisohexyl-3-cyclohexene carboxaldehyde, butylated hydroxytoluene, ketoconazole, petrolatum, mineral oil, or paraffinum liquidum.

In one embodiment, the commercial hair care product is a curl activating or relaxing solution, which may include carbomer, hexyl cinnamal, benzyl salicylate, trolamine salicylate, benzyl benzoate, limonene, eugenol, 1,3-Bis(hydroxymethyl)-5,5-dimethyl-limidazolidine-2,4-dione (DMDM Hydantoin), para-aminobenzoic acid (PABA), 2-ethylhexyl 4-dimethylaminobenzoate (Padimate O), butylphenyl methylpropional, propylparaben, phenolsulfonphthalein (PSP, phenol red), or a polysorbate.

In one embodiment, the additive comprises a commercial hair dye formulation, which may include hydrated iron oxide $(Fe(OH)_3)$, para-phenylenediamine, ortho-, meta-, or para-aminophenol, 4-amino-2-hydroxytoluene, trideceth-2 carboxamide MEA, phenyl methyl pyrazolone, phenoxyethanol, a polyquaternium, hexyl cinnamal, butylphenyl methylpropional, phenolsulfonphthalein (PSP, phenol red), hydroxyisohexyl 3-cyclohexene carboxaldehyde, titanium dioxide, or iron oxide.

In one embodiment, the additive comprises a commercial pesticide, which may include, but is not limited to, orthophenylphenol (OPP), phenylhydroquinone (PHQ) or phenylbenzoquinone (PBQ).

In one embodiment, the additive comprises a compound with a two-dimensional structure, which may include, but is not limited to, lignin, graphene, or graphene oxide.

In one embodiment, the additive comprises a carbon form, which may include, but is not limited to, peat, lignite, bituminous coal, sub-bituminous coal, pulverized coal, nano-coal, steam coal, cannel coal, anthracite, charcoal, carbon black, activated charcoal, black liquor, graphite, graphene, graphene oxide, or sugar char. In one embodiment, the carbon form serves as a heat transfer agent in the lubricating composition.

In one embodiment, the carbon form comprises a nanopowder. In one embodiment, the carbon form has an increased surface area. In one embodiment, the carbon form comprises a nano-activated charcoal. The nano-activated charcoal may comprise particles of activated charcoal that have been ground from a conventional activated charcoal to nanoparticle size. The activated charcoal may be ground using any conventional method to produce nanometer-sized particles. In one embodiment, the activated charcoal is ground using known wet or dry nano-milling techniques of grinding solids to sub-micron particle sizes. In one embodiment, the nano-activated charcoal has an average particle size less than ~100 nm. In one embodiment, substantially all of the particles have a size less than ~100 nm. In some one embodiment, the nano-activated charcoal has an average particle size less than ~50 nm. In one embodiment, substantially all of the particles have a size less than ~50 nm.

In one embodiment, the carbon form comprises graphitic carbon. In one embodiment, the graphitic carbon comprises at least one PAH, which may include, but is not limited to, naphthalene, acenaphthylene, acenaphthene, fluorine, phenanthrene, anthracene, fluoranthene, pyrene, benzo[a]anthracene, chrysene, benzo[b]fluoranthene, benzo[k]fluoranthene, benzo[j]fluoranthene, benzo[a]pyrene, benzo[e]pyrene, dibenz[a,h]anthracene, benzo[g,h,i]perylene, indeno[1,2,3-c,d]pyrene, tetracene, coronene, corannulene, pentacene, triphenylene, and ovalene.

In one embodiment, the carbon form comprises a biochar or biocoal product of a hydrothermal carbonization process.

In one embodiment, the additive provides the same benefits provided by tricresyl phosphate (TCP) to the lubricating system. TCP is considered a carcinogen and a factor in aerotoxic syndrome and is being phased out of use in many lubricating systems.

In some embodiments, the additive comprises a "dirty" or poorly-refined form of mineral oil with high levels of PAH contamination. Industrially-produced white mineral oil includes very low levels of PAHs, which must be essentially completely removed in order to sell the mineral oil as "USP" or "food grade". In one embodiment, the separated waste mineral oils from these processes (having the highest concentrations of PAHs) are used unprocessed and directly as additives or in combination with other additives. The white mineral oil component in this waste product serves as a wetting agent in the lubricating composition and the PAHs serve as a heat transfer agent and graphitic carbon source in the formation of SGANs and SGAN-containing microsphere agglomerates.

In one embodiment, the additive comprises a compatibilizer. A compatibilizer, as used herein, refers to a compound that aids in the dispersal of a carbon source in a lubricant or lubricating composition. In some embodiments, the compatibilizer is an amphiphile. In some embodiments, the compatibilizer comprises a surfactant. In some embodiments, the compatibilizer comprises a lipid. In some embodiments, the compatibilizer comprises a polymer. In some embodiments, the compatibilizer also serves as a carbon source.

In some embodiments, the compatibilizer comprises a sugar amphiphile. A sugar amphiphile or a sugar-like amphiphile may be any molecule with a hydrophilic sugar portion and a hydrophobic portion, including, but not limited to, those described by Fenimore ("Interfacial Self-assembly of Sugar-based Amphiphiles: Solid- and Liquid-core Capsules", University of Cincinnati Ph.D. thesis dated Oct. 16, 2009), Jadhav et al. ("Sugar-Derived Phase-Selective Molecular Gelators as Model Solidifiers for Oil Spills", *Angew. Chem. Int. Ed.*, Vol. 49, pp. 7695-7698, 2010), Jung et al. ("Self-Assembling Structures of Long-Chain Sugar-Based Amphiphiles Influenced by the Introduction of Double Bonds", *Chem. Eur. J.*, Vol. 11, pp. 5538-5544, 2005), Paleta et al. ("Novel amphiphilic fluoroalkylated derivatives of xylitol, D-glucose and D-galactose for medical applications: hemocompatibility and co-emulsifying properties", *Carbohydrate Research*, Vol. 337, pp. 2411-2418, 2002), Germaneau ("Amphiphilic Sugar Metal Carbenes: From Fischer Type to N-Heterocyclic Carbenes (NHCs)", Rheinische Friederich-Wilhems-Universitat Bonn Ph.D. thesis, 2007), and Ye et al. ("Synthesis of Sugar-Containing Amphiphiles for Liquid and Supercritical Carbon Dioxide", *Ind. Eng. Chem. Res.*, Vol. 39, pp. 4564-4566, 2000). Sugar amphiphiles may also include, but are not limited to, sophorolipids (Zhang et al., "Synthesis and interfacial properties of sophorolipid derivatives", *Colloids and Surfaces A: Physicochem. Eng. Aspects*, Vol. 240, pp. 75-82, 2004), or rhamnolipids (Christova et al., "Rhamnolipid Biosurfactants Produced by *Renibacterium salmoninarum* 27BN During Growth on n-Hexadecane", *Zeitschrift fur Naturforschung Teil C Biochemie Biophysik Biologie Virologie*, Vol. 59, pp. 70-74, 2004).

In one embodiment, the compatibilizer comprises a non-sugar graphene-promoting amphiphile. A graphene-promoting amphiphile may be any molecule with a hydrophilic graphene-promoting portion and a hydrophobic portion, which may include, but is not limited to, cetyltrimethylammonium bromide or those marketed by Dow Chemical Company (Midland, Mich., United States) under the trademarks TRITON™ or TERGITOL™, including, but not limited to, the TRITON™ X series of octylphenol ethoxylates and the TERGITOL™ NP series of nonylphenol ethoxylates. In some embodiments, the graphene-promoting amphiphile is a non-ionic amphiphile. Graphene-promoting amphiphiles may also comprise, but are not limited to, glycerol monostearate and nonoxyphenol surfactant.

In one embodiment, the compatibilizer comprises polyethylene glycol.

In one embodiment, the compatibilizer is used in combination with a particulate additive. In one embodiment, the compatibilizer promotes solubilization of the particulate additive in the base lubricant.

In one embodiment, the additive comprises a metal oxide, which may comprise, but is not limited to, iron oxide, aluminum oxide, copper oxide, nickel oxide, titanium oxide, and lead oxide.

In one embodiment, the additive comprises a form of iron. In some lubricating systems, such as many jet engine turbines, little or no iron is inherently present in the system. Carbon-encapsulated iron particles formed in situ, however, are believed to provide the nano-polishing ability to lubricating compositions of the invention. Therefore, in one embodiment, the lubricating fluid is supplemented with an iron-containing additive.

In one embodiment, the iron-containing additive comprises an iron oxide. In one embodiment, the iron oxide is BayFerrox® iron oxide powder pigment (Lanxess, Cologne, Germany). In one embodiment, the iron-containing additive comprises an iron oxide nanopowder. In one embodiment, the iron source comprises an iron complex molecule.

In one embodiment, the additive comprises a cyclic iron-containing compound, including, but not limited to, ($\eta^2$-trans-Cyclooctene)$_2$Fe(CO)$_3$; (benzylideneacetone)iron tricarbonyl, ferric enterochelin, tricarbonylbis[(1,2-h)-cycloctene]-iron, iron(4+) cyclooctane-1,2-diide—carbon monoxide, sodium ferrate(1-); sodium bis(3-(4,5-dihydro-4-((2-hydroxy-5-nitrophenyl)azo)-3-methyl-5-oxo-1H-pyrazol-1-yl)benzene-1-sulphonamidato(2-)) ferrate(1-); ferritin; (cyclo-1,3-C$_4$H$_8$—S$_2$)Fe(CO)$_4$; iron 2,4-dinitrobenzene-1,3-diol; iron phthalocyanine; ferrocene; ferric benzoate; ferric salicylate; cyclic ferrates; or iron protein succinylate.

In one embodiment, the additive comprises an acyclic iron-containing compound, including, but not limited to, diiron nonacarbonyl, iron pentacarbonyl, acyclic ferrates, liquid iron, iron oxalate, hydrated iron oxide (Fe(OH)$_3$), or an iron-containing nutritional supplement. In one embodiment, the iron-containing nutritional supplement comprises carbonyl iron. In one embodiment, the iron-containing complex is a catecholate-iron complex.

In one embodiment, the additive comprises a siderophore, which may include, but is not limited to, 2,3-dihydroxybenzoic acid (2,3'-DHB), N,N',N"-((3S,7S,11S)-2,6,10-trioxo-1,5,9-trioxacyclododecane-3,7,11-triyl)tris(2,3-dihydroxybenzamide) (enerobactin), or 2,4-dihydroxybenzoic acid (2,4'-DHB).

In one embodiment, the additive comprises an anthelmintic, including, but not limited to, 2-deoxy-paraherquamide (PHQ).

In one embodiment, the additive comprises an aromatic amino acid precursor, including, but not limited to, (3R,4R)-3-[(1-carboxyvinyl)oxy]-4-hydroxycyclohexa-1,5-diene-1-carboxylic acid (chorismic acid).

In one embodiment, the additive comprises a molecule capable of sequestering iron, which may include, but is not limited to, ethylenediaminetetraacetic acid, 2-aminophenol (see Pulgarin et al., "Iron Oxide-Mediated Degradation, Photodegradation, and Biodegradation of Aminophenols", *Langmuir*, Vol. 11, pp. 519-526, 1995 and Andreozzi et al., "Iron (III) (hydr)oxide-mediated photooxidation of 2-aminophenol in aqueous solution: a kinetic study", *Water Research*, Vol. 37, pp. 3682-3688, 2003), or tetraphenyl oxo-metalloporphyrins.

In one embodiment, the additive comprises nanodiamond intended to serve as the nucleating core of nanoparticles or microparticles incorporating the graphitic carbon formed in situ in the lubricating composition.

The ex situ pyrolytic synthesis of SGANs and SGAN-containing agglomerates also accommodates the use of such molecules in non-lubricating applications. In one embodiment, the particles or agglomerates can be applied to the surface of a material as a coating to strengthen the material or increase the heat shielding or heat absorption of the material. In one embodiment, the coating can be a thermal coating, a drill coating, or a torch-resistant coating. In one embodiment, the material can be a ballistic projectile, which may include, but is not limited to, bullets and missiles. In one embodiment, the material can be an anti-ballistic device, including, but not limited to, military tank armor or personal armor, including, but not limited to, bullet-resistant vests or plates. In one embodiment, the material can be a tool, including, but not limited to, a cutting bit, a tunneling device, an abrasive polish, an abrasive paper, or a boring device. In one embodiment, the material can be a thermal shield, such as a re-entry heat shield panel, a nosecone, or a rocket engine cone for a spacecraft. In one embodiment, the particles or agglomerates can be combined with a material to form a composite material with greater strength or greater heat shielding or heat absorption properties than the base material itself. In some embodiments, the material can be a tire, fireproofing, firefighting equipment, or firefighting apparel.

In one embodiment, the SGANs or SGAN-containing agglomerates of the invention can be used in electrochemical systems. In one embodiment, the SGANs or SGAN-containing agglomerates of the invention can be used as nano-batteries to hold an electrical charge.

Test Results

Several lubricating compositions, including sacrificial carbon sources with structures expected to promote graphitic carbon formation under engine operating conditions, were tested in a series of motor scooters or motorized dirt bikes. These tests were conducted to test the efficacy of the compositions in small internal combustion engines, engines of a size and configuration such that improvements in friction reduction would be sufficiently obvious to a mechanic or operator without employing an external dynamometer to measure the changes.

Test 7

The conventional Valvoline® (Ashland Inc., Lexington, Ky., United States) 10W-40 motor oil of a poorly functioning 8,850 mile 1999 Honda Elite 80 (Model CH80) (Honda de Mexico, S. A. de C.V., Guadalajara, Jalisco-Mexico) motor scooter was replaced with a lubricating composition of the invention. Prior to addition of the lubricating composition, the engine of the motor scooter would barely maintain idle. When tested, the scooter would start, but soon after, would stall. When the motor scooter did operate, the top indicated speed was approximately 30 miles per hour.

The lubricating composition tested included several hundred milligrams of Whole Foods Market (Austin, Tex., United States) Organic Powdered Sugar (powdered sucrose and tapioca) mixed with Walgreens (Deerfield, Ill., United States) Intestinal Lubricant (USP mineral oil) mixed into Motul (Aubervilliers, France) 5100 10W-40 semi-synthetic motor oil. The lubricating composition had an opaque appearance due to the large presence of sugar suspended in the solution.

Upon addition of the lubricating composition to the motor scooter, the engine was started and was then able to maintain an idle. Immediately thereafter, the motor scooter was taken for a performance evaluation test ride. The lubricating composition was found to almost instantly increase the top speed of the motor scooter from 30 to 35 MPH indicated. A distinct difference in the sound of the engine was also noted, with the engine sounding much smoother and quieter with use of the lubricating composition. After the test ride, the lubricating composition was drained from the engine when a characteristic epoxy-like smell was noted in the oil. This characteristic epoxy-like odor was expected and is believed to indicate the presence of epoxy-type precursor compounds in the oil, having formed from the incomplete pyrolysis of some of the remaining sugar molecules in the lubricating composition.

Test 8

Another lubricating composition tested in the same 1999 Honda Elite 80 motor scooter (Model CH80) (Honda de Mexico, S. A. de C.V., Guadalajara, Jalisco-Mexico) consisted of one individual serving packet (one gram) of Sweet'n Low (Cumberland Packing Corp., Brooklyn, N.Y., United States) zero calorie sweetener (dextrose, saccharin, cream of tartar, calcium silicate) in a few milliliters of CitraSolv® (Danbury, Conn., United States) natural cleaner and degreaser (d-limonene source), that was then combined with a Valvoline® (Ashland Inc., Lexington, Ky., United States) 10W-40 conventional motor oil.

The motor scooter operated similarly on the saccharin-containing lubricating composition to the sugar-containing lubricating composition described above. After testing, this lubricating composition was drained from the motor scooter with little visible particulate noted. The drained oil was otherwise unremarkable, save the strong citrus smell from the limonene-containing CitraSolv® cleaner and degreaser.

Test 9

Yet another lubricating composition was tested in the same 1999 Honda Elite 80 (Model CH80) (Honda de Mexico, S. A. de C.V., Guadalajara, Jalisco-Mexico) motor scooter, that included Whole Foods Market (Austin, Tex., United States) Organic Powdered Sugar (powdered sucrose and tapioca) mixed with activated charcoal as an additive to Valvoline® (Ashland Inc., Lexington, Ky., United States) 10W-40 conventional motor oil.

According to the Valvoline® motor oil's Material Safety Data Sheet, the oil has a reported flash point of 204° C. (399.2° F.) and a reported boiling point of 299° C. (570.2° F.). The normal operating temperature of the air-cooled engine's cylinder head was measured to be ~80° C. (176° F.).

During the test, the engine cowling was modified to completely block all air flow from the cooling fan to the cylinder head. This meant that as the engine ran, the air surrounding the cylinder head was trapped and began to heat-up. The rising temperature of the cylinder head was monitored by a Cen-Tech (Zhangzhou Eastern Intelligent Meter Co. Ltd., Zhangzhou, Fujian, China) 96451 Non-Contact Infrared Thermometer with Laser Targeting.

The engine was run in this condition until the cylinder head reached a measured temperature of approximately 225° C. (437° F.). At this point in temperature, smoke was observed billowing from the crankcase breather valve and the plastic cowling around the engine was seen to begin melting. While in this condition and at this temperature, the engine was again run WOT (wide-open throttle) and the engine continued to run without seizing. A short time thereafter, the engine was turned off and allowed to cool down. Then the motor scooter was test ridden for a few miles during which it was observed to run perfectly smoothly with no noted degradation in performance.

Test 10

In yet another lubricating composition, ~200 mL of Whole Foods Market, LP (Austin, Tex., United States) apricot kernel oil (amygdalin source) was combined with ~550 mL of Valvoline® (Ashland Inc., Lexington, Ky., United States) 10W-40 conventional motor oil. This lubricating composition was placed in a 125 mile 2011 JMStar (Shanghai JMStar Motorcycle Co., Ltd., Shanghai, China) 150 cubic centimeter displacement GY6-style engine motor scooter.

Although no measured increase in indicated top speed of the motor scooter was discernible during the evaluation test ride, the engine sounded qualitatively better and smoother using the lubricating composition, than with the conventional oil alone.

Test 11

In another lubricating composition, several ounces of Roddenberry's Cane Patch Invert Sugar Cane Syrup (Bay Valley Foods, LLC, Green Bay, Wis., United States) and ~100 mL of Marvel® Mystery Oil (Turtle Wax, Inc., Westmont, Ill., United States, naphthenic carbon source) were combined with Valvoline® (Ashland Inc., Lexington, Ky., United States) 10W-40 conventional motor oil. This lubricating composition was placed in a Baja Motor Sports (Phoenix, Ariz., United States) Dirt Runner 125 cubic centimeter displacement motorized dirt bike.

Prior to the test, the dirt bike ran, but not particularly well. Once the lubricating composition was added to the engine, the engine sounded qualitatively better and ran smoother than with the conventional lubricant. At the conclusion of the performance evaluation test rides, the oil was drained from the dirt bike's engine and the anticipated and characteristic epoxy-like smell was again noted, indicating the presence of phenolic resin/epoxy precursors in the lubricant.

Test 12

In another lubricating composition, approximately 50 mL of Spectrum USP-grade benzyl benzoate (Spectrum Chemical Mfg. Corp., New Brunswick, N.J., United States) was mixed with 50 mL of 5W-30 G-Oil® (Green Earth Technologies, Celebration, Fla., United States) Ultimate Biodegradable green motor oil, a conventional tallow-based motor oil. The approximately 100 mL of lubricating composition was then added to the existing engine oil in a 125 mile 2011 JMStar (Shanghai JMStar Motorcycle Co., Ltd., Shanghai, China) 150 cubic centimeter displacement GY6-style engine motor scooter. This lubricating composition qualitatively seemed to perform the best of all the lubricating compositions tested.

A significant change in engine noise was observed after addition of the lubricating composition and the maximum engine RPMs were later noted to have increased by 1000 RPM from approximately 10,000 RPM to 11,000 RPM.

Test 13

In another lubricating composition, approximately 20 drops of Aura Cacia Organic Cinnamon Leaf Oil (Frontier Natural Products Co-Op, Norway, Iowa, United States, methyl cinnamate source) and approximately 10 mL of Walgreens (Deerfield, Ill., United States) Intestinal Lubricant (USP mineral oil), were combined with ~200 mL of Green 5W-30 G-Oil® (Green Earth Technologies, Celebration, Fla., United States) Ultimate Biodegradable green motor oil. This lubricating composition was placed in a Baja Motor Sports (Phoenix, Ariz., United States) Dirt Runner 125 cubic centimeter displacement motorized dirt bike. This lubricating composition performed similarly to the previous lubricating composition including benzyl benzoate, yet a pungent cinnamon-like odor was noted while operating.

Test 14

In another lubricating composition, approximately 100 mL of a mixture of Spectrum® USP-grade benzyl benzoate (Spectrum Chemical Manufacturing Corp., New Brunswick, N.J., United States), Walgreens (Deerfield, Ill., United States) Intestinal Lubricant (USP mineral oil), and Lucas Automatic Transmission Fluid Conditioner (Lucas Oil Products, Inc., Corona, Calif., United States, antioxidant source) was added to the engine base lubricant of a new (2-mile) 2011 50 cc-engine scooter, model GMW-M2 (Taizhou Zhongneng Motorcycle Company, Ltd., Taizhou, China) with a modified transmission and exhaust system. An almost instant increase in horsepower of the engine was noted and the top speed of the scooter almost instantly increased from 33 to 39 MPH, indicated, an 18% increase.

Test 15

In another lubricating composition, a formulation comprising three quarts of a ZDDP-containing high grade synthetic motorcycle motor oil mixed with about one quart of a mixture comprising Marvel Mystery Oil original formula, Turtle Wax, Inc., Westmont, Ill., United States), Lucas Synthetic Oil Stabilizer (Lucas Oil Products, Inc., Corona, Calif., United States), Lucas Automatic Transmission Fluid Conditioner (Lucas Oil Products, Inc., Corona, Calif., United States), and zMAX® (Oil-Chem Research Corporation, Bedford Park, Ill., United States), in a volume ratio of about 60:17:70:30 was used to replace the existing motor oil in a 1999 Yamaha R1 (Yamaha Motor Co., Ltd., Iwata, Japan) test motorcycle with a 1000 cc engine. Engine performance testing with this formulation was accomplished using a Dynojet 250i dynamometer (Dynojet Research Inc., Las Vegas, Nev., United States) to measure the power and torque output at the rear wheel of the test motorcycle both 10 minutes after the oil change and again one week after the oil change. A summary of the dynamometer test results for these two test runs is shown in Table 2(a) and Table 2(b):

TABLE 2(a)

Dynamometer test results - maximum output

| Power Output | Original | 10 Minutes | 1 Week |
| --- | --- | --- | --- |
| Maximum Horsepower | 135.14 | 136.08 | 138.49 |
| Maximum Torque (ft/lbs) | 73.06 | 74.04 | 75.31 |

TABLE 2(b)

Dynamometer test results - largest measured increase

| Power Output | 10 Minutes | 1 Week |
| --- | --- | --- |
| Horsepower @ 7,500 RPM | 102.96 | 107.90 |

As can be seen in Table 2(a), an increased output of about 1 horsepower and about 1 ft-lb of torque is observed in the 10-minute test, in comparison to the horsepower and torque previously measured on the motorcycle using another commercially-available high grade motorcycle motor oil. The effect of the new lubrication composition was even more dramatic after 7 days of use. At the subsequent 1-week test, an additional increase in registered horsepower and torque output of 3% to 4% over the 10-minute test values was observed. Specifically, the registered horsepower increased by about 3 to 5 HP across the entire range of engine speeds tested (4500 RPM to about 11,000 RPM). As seen in Table 2(b), a horsepower output of 102.96 was measured at 7500 RPM during the 10-minute test, compared to a horsepower output of 107.90 measured at 7500 RPM during the subsequent 1-week test. The maximum torque increased from about 74.04 to about 75.3 ft-lbs from the 10-minute test to the 1-week test.

Test 16

In another lubricating composition, about three to about four ounces of a mixture of Marvel Mystery Oil (original formula, Turtle Wax, Inc., Westmont, Ill., United States), Lucas Synthetic Oil Stabilizer (Lucas Oil Products, Inc., Corona, Calif., United States), Lucas Automatic Transmission Fluid Conditioner (Lucas Oil Products, Inc., Corona, Calif., United States), zMAX® micro-lubricant (Oil-Chem Research Corporation, Bedford Park, Ill., United States), were combined with Marvel Air Tool Oil (Turtle Wax, Inc., Westmont, Ill., United States), in a volume ratio of about 12:3:14:10:9 and then added to the existing engine lubricant in a 2006 Audi A4 2.0 liter Turbo (Audi AG, Ingolstadt, Germany) test automobile, producing phenomenal performance and fuel economy results. This additive package, as well as similar additive concentrate formulations, may be added directly to the motor oil already in a vehicle to improve engine performance without the need for replacing the existing motor oil.

Test 17

In yet another lubricating composition, a concentrated additive package not intended to influence the performance of any existing base motor oil or its additives, was accomplished by using about one quart of a mixture of Marvel Mystery Oil (original formula, Turtle Wax, Inc., Westmont, Ill., United States), Lucas Synthetic Oil Stabilizer (Lucas Oil Products, Inc., Corona, Calif., United States), Lucas Automatic Transmission Fluid Conditioner (Lucas Oil Products, Inc., Corona, Calif., United States), and Marvel Air Tool Oil (Turtle Wax, Inc., Westmont, Ill., United States), in a volume ratio of about 12:3:14:16.

This concentrated additive package was added to a high-quality, non-ZDDP-containing, synthetic motor oil and introduced into a 2006 Audi A4 2.0 liter Turbo (Audi AG, Ingolstadt, Germany) test automobile, producing phenomenal performance and fuel economy results. This additive package, as well as similar additive concentrate formulations, may be added directly to the motor oil already in a vehicle to improve engine performance without the need for replacing the existing motor oil.

Lubricating Composition Experimental Observations for Tests 16 and 17

Subsequently, metal engine components from the Audi A4 test automobile (Audi AG, Ingolstadt, Germany) were removed and subjected to non-destructive scientific analyses. In this case, a machined steel camshaft cam follower and cam follower retaining ring were removed from the test automobile after 150,000 miles of use with various incarnations of the lubricating composition. According to the manufacturer, these parts are made of stainless steel. The results of those analyses follow.

The first of the scientific analyses of the engine components was a surface roughness analysis using a NewView™ 7300 white light optical surface profiling interferometer (Zygo® Corporation, Middlefield, Conn., United States). The removed cam follower's friction and non-friction surfaces were evaluated and compared using the interferometer. The arithmetic mean ($R_a$), peak-valley (PV), and root-mean-squared (RMS) average surface roughnesses were determined. The results and findings are summarized in FIG. 20, FIG. 21, and Table 3.

TABLE 3

Optical Surface Profiling Results

| Cam Follower Section | Ave. Roughness ($R_a$, nm) | PV (μm) | RMS (nm) |
|---|---|---|---|
| Original/Unworn Surface | 221.6 | 2.27 | 284.51 |
| Polished/Friction Surface | 3.44 | 0.11 | 5.51 |

As can be seen, an almost two order of magnitude improvement in surface smoothness was achieved using formulations of the present invention. Average surface roughness ($R_a$) was reduced from a minimum starting value of at least $R_a$=221.6 nm to a measured end value of $R_a$=3.44 nm.

Figure 20:
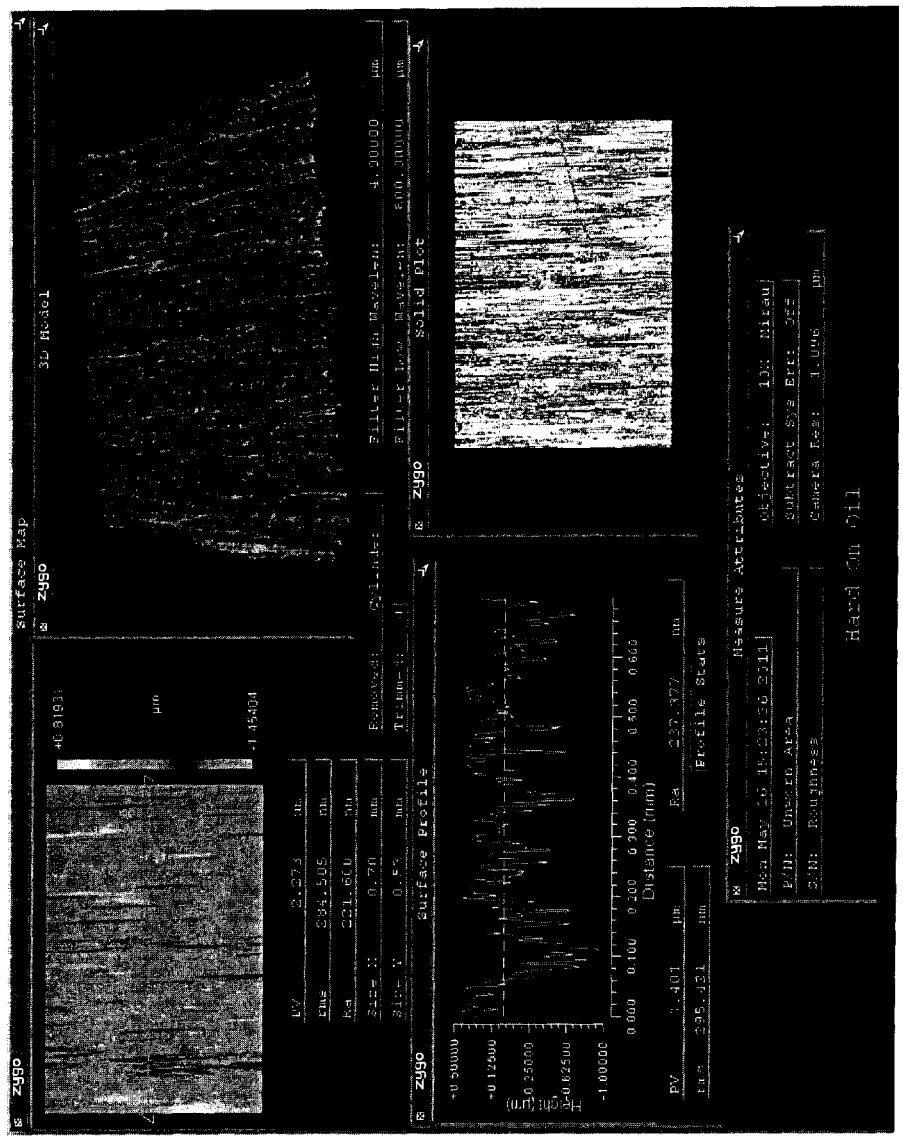
FIG. 20 shows the results of surface roughness measurements on a non-wear surface of a machined stainless steel cam follower after exposure to a lubricating composition in an embodiment of the invention.

FIG. 20 shows that the non-wear surface, which did not make repeated close contact with the walls of the cylinder head during operation of the automobile, was measured to have an $R_a$ value of 221.6 nm, which is typical for such an engine part in a high-quality automobile (average automobile cam follower tolerances $R_a$=300 to 400 nm). The graphical representation in the bottom left quadrant of FIG. 20 shows what can be considered an estimation of the approximate beginning surface roughness measurements for the cam follower section evaluated, that is to say, its estimated relative condition upon assembly into the test automobile's engine.

Figure 21:
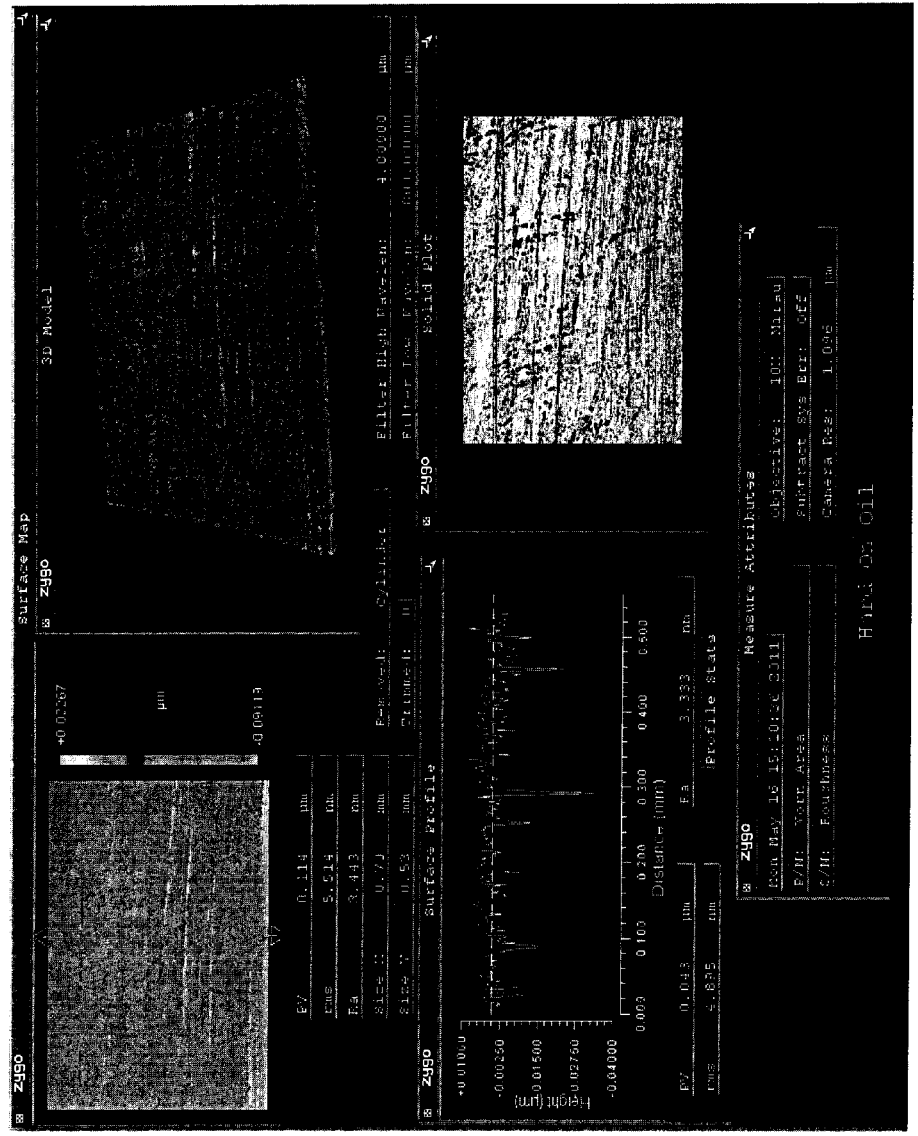
FIG. 21 shows the results of surface roughness measurements on a wear surface of a machined stainless steel cam follower after exposure to a lubricating composition in an embodiment of the invention.

FIG. 21, however, shows that the wear surface, which was in constant frictional contact with the walls of the cylinder head during operation of the engine, was measured to have an $R_a$ value of 3.44 nm, almost two orders of magnitude lower than the measured roughness of the non-wear surface, which indicates the approximate and estimated original state of the cam follower at time of manufacture and assembly of the engine. The original machining asperities observed in FIG. 20 are oriented perpendicularly to the asperities observed in FIG. 21, indicating that the original machining asperities in the wear surface were completely removed at one point in the polishing process.

These data indicate that the wear surface of the cam follower has been super-polished during operation of the engine. While super-polishing of surfaces of materials such as fused silica, silicon, and silicon carbide down to a surface roughness $R_a$ value of 0.4 nm is possible under highly controlled laboratory circumstances, polished metal surfaces typically have a much higher $R_a$ value in the range of hundreds of nanometers. Liu et al. (*SIMTech Technical Reports*, Vol. 8, No. 3, pp. 142-148, July-September 2007) report a two-step super-polishing process capable of producing (under laboratory conditions) a stainless steel lens mould insert with a surface roughness $R_a$ value of 8.5 nm.

Since two pieces of metal in contact are not capable of producing surfaces of the smoothness observed in FIG. 21 without a polishing agent, the wear surface of the cam follower was tested further to try to determine the polishing agent in the lubricating composition capable of producing a surface as smooth as surface achieved in the test of the invention. The wear surface of a cam follower is typically made of surface-hardened steel, and the nanoparticle polishing agents, one of which is referenced herein as an SGAN, in order to be able to polish a surface, is expected to be harder than the surface being polished. The 2-dimensional surface topology of the wear surface in FIG. 21 shows a number of circular features in the size range of one or two nanometers in diameter, which is on the scale of the expected size of the SGAN or other abrasive nanoparticles that would be necessary in order to achieve such a low surface roughness $R_a$ value.

The non-wear surface from a retaining ring of the cam follower was studied using a Philips® XL series XL 30 ESEM-FEG (FEI™ Company, Hillsboro, Oreg., United States), using EDAX® Genesis™ version 4.61 software (AMATEK® Inc., Mahwah, N.J., United States) and a Scandium Imaging Platform. The resulting electron microscope images of surfaces of the retaining ring are shown in FIGS. 22 through 41. The accompanying elemental analysis from energy-dispersive x-ray spectroscopy (EDS) for the four surfaces showed only carbon, oxygen, and iron in the weight (wt %) and atomic (At %) percentages shown in Table 4(a) for the areas in the black boxes sampled in FIGS. 22 through 25, respectively, except for FIG. 22, which showed traces (<1 At %) of potassium and chromium. The images show spheroid structures on the non-wear surface with diameters in the range of ~2-3 microns.

TABLE 4(a)

Preliminary Elemental Analysis Data

Figure 22:
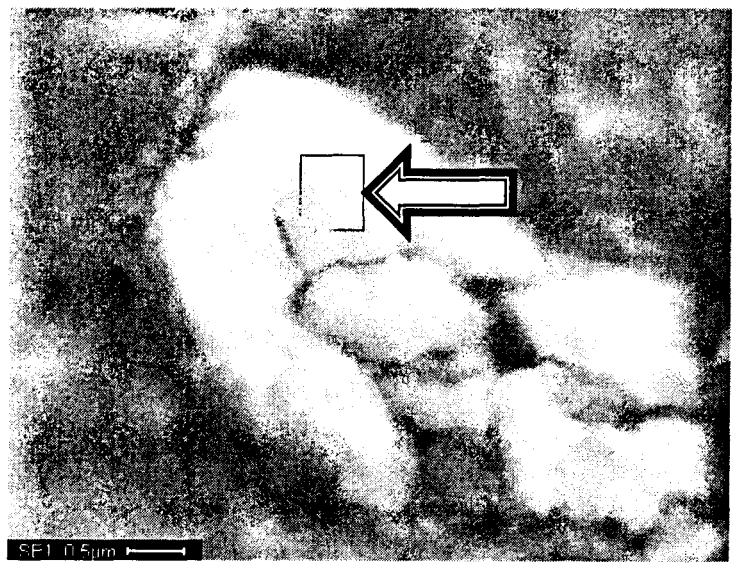
FIG. 22 shows an SEM image of a first portion of a non-wear surface of a cam follower retaining ring after exposure to a lubricating composition in an embodiment of the invention.
Figure 23:
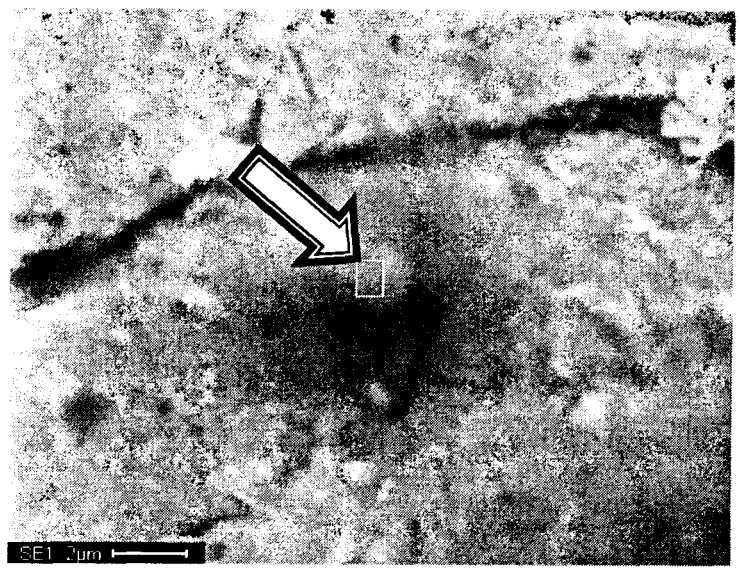
FIG. 23 shows an SEM image of a second portion of the non-wear surface of the cam follower retaining ring.
Figure 24:
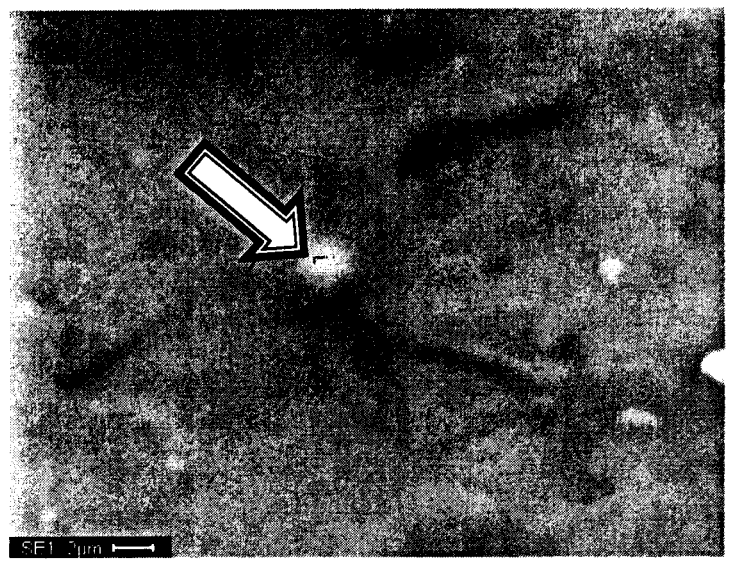
FIG. 24 shows an SEM image of a third portion of the non-wear surface of the cam follower retaining ring.
Figure 25:
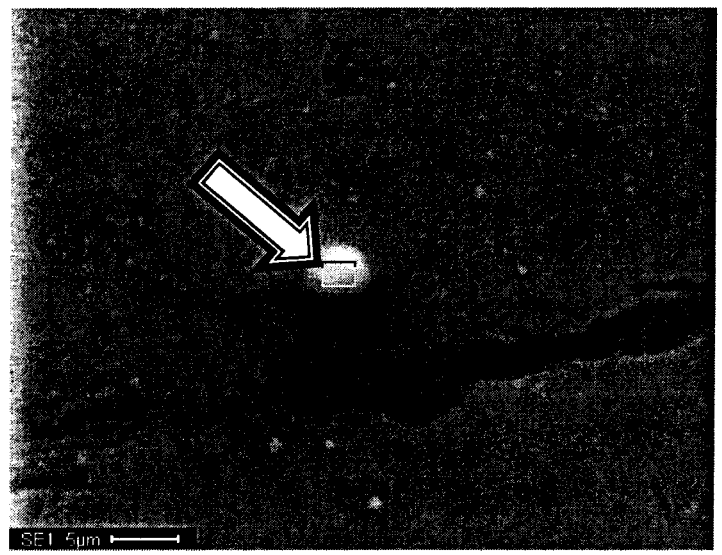
FIG. 25 shows an SEM image of a fourth portion of the non-wear surface of the cam follower retaining ring.
Figure 26:
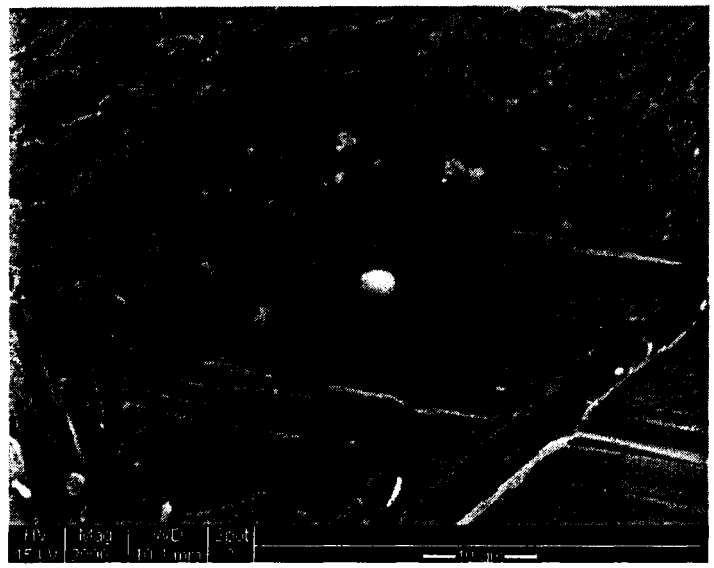
FIG. 26 shows an SEM electron micrograph of a fifth portion of the non-wear surface of the cam follower retaining ring.
Figure 27:
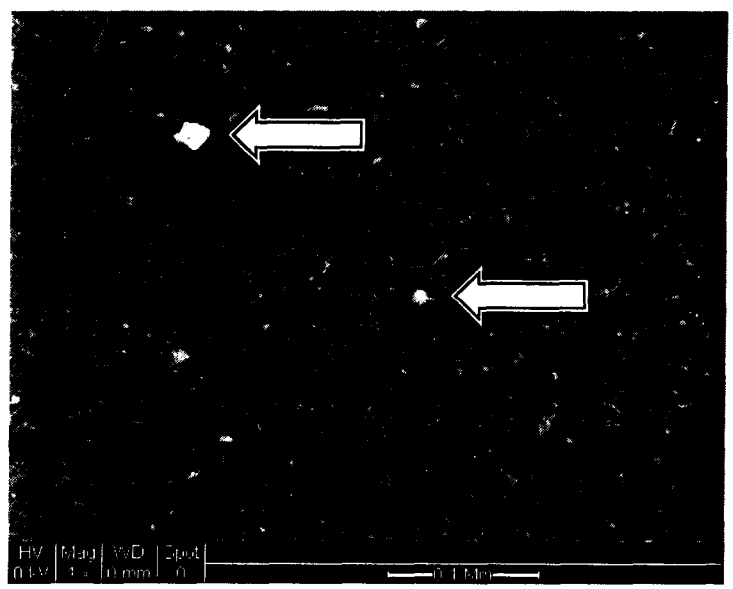
FIG. 27 shows an SEM image of a sixth portion of the non-wear surface of the cam follower retaining ring.
Figure 28:
FIG. 28 shows an SEM image of a seventh portion of the non-wear surface of the cam follower retaining ring.
Figure 29:
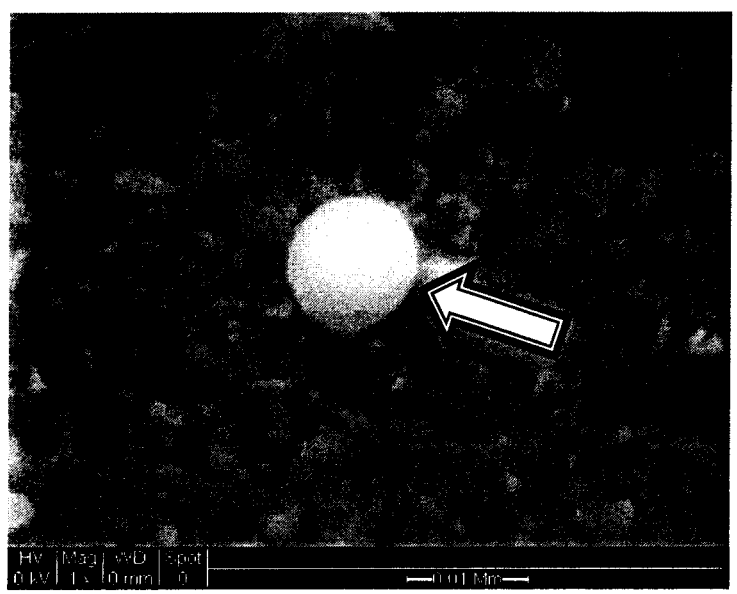
FIG. 29 shows an SEM image of an eighth portion of the non-wear surface of the cam follower retaining ring.
Figure 30:
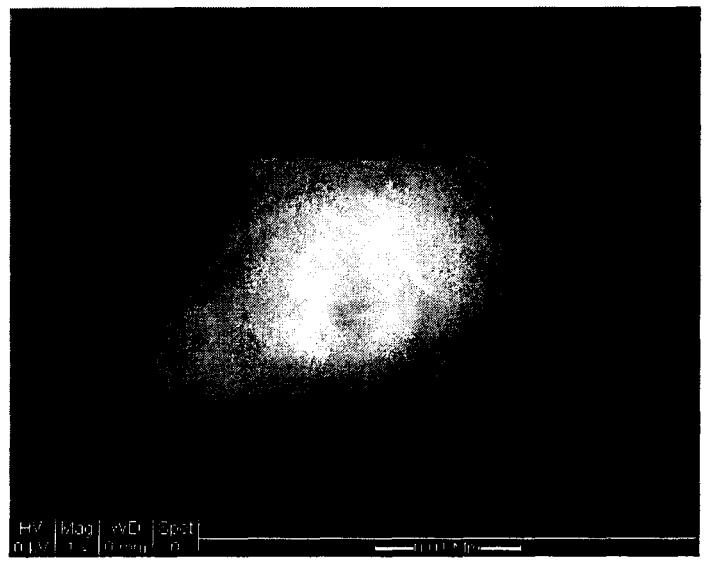
FIG. 30 shows an SEM image of a ninth portion of the non-wear surface of the cam follower retaining ring.
Figure 31:
FIG. 31 shows an SEM image of a tenth portion of the non-wear surface of the cam follower retaining ring.
Figure 32:
FIG. 32 shows an SEM image of an eleventh portion of the non-wear surface of the cam follower retaining ring.
Figure 33:
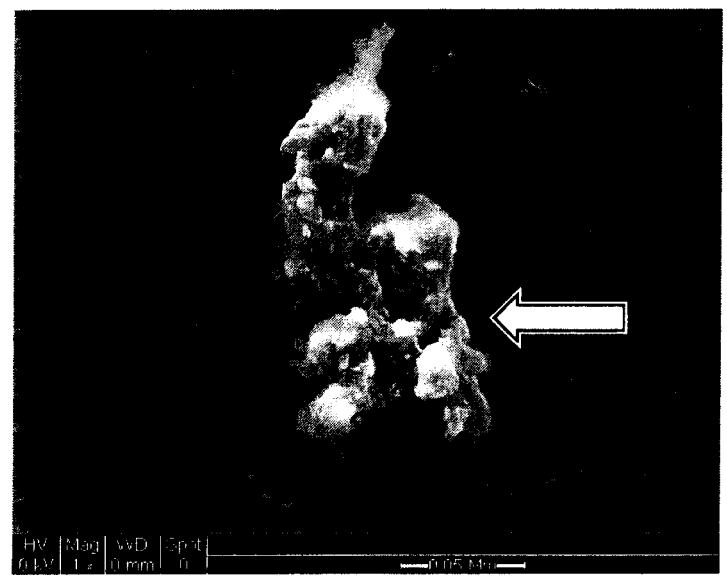
FIG. 33 shows an SEM image of a first close up of the crystalline structure on the left side of FIG. 32.
Figure 34:
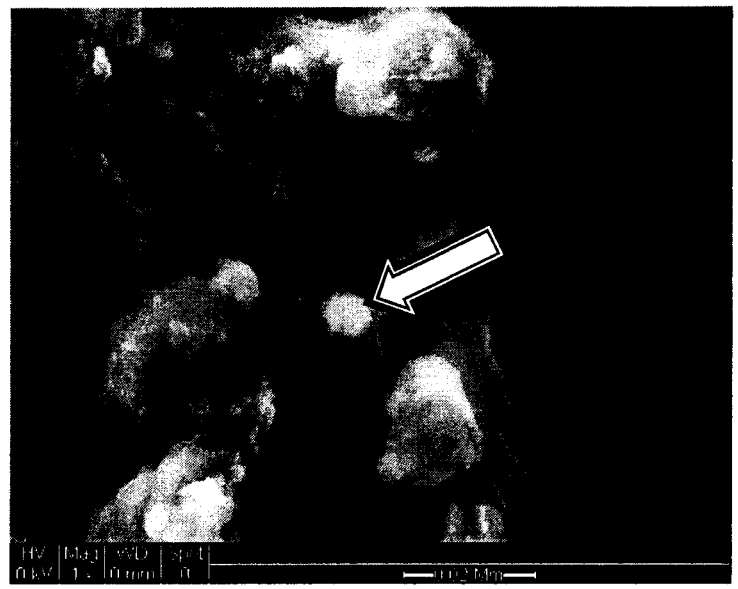
FIG. 34 shows an SEM image of a twelfth portion of the non-wear surface of the cam follower retaining ring.
Figure 35:
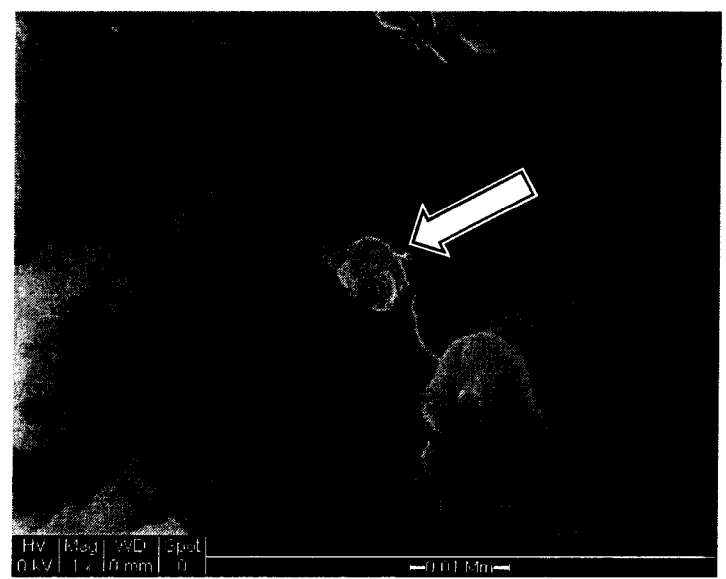
FIG. 35 shows an SEM image of the crystalline structure on the left side of FIG. 32.
Figure 36:
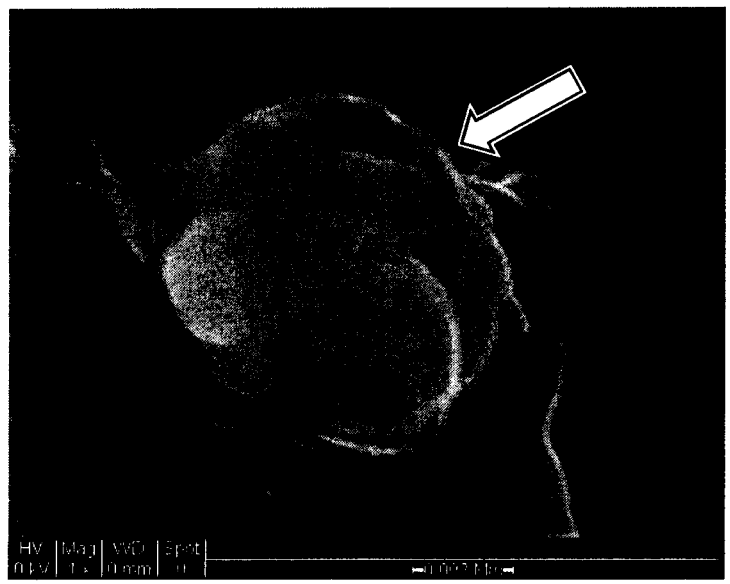
FIG. 36 shows an SEM image of a second close up of the crystalline structure on the left side of FIG. 32.
Figure 37:
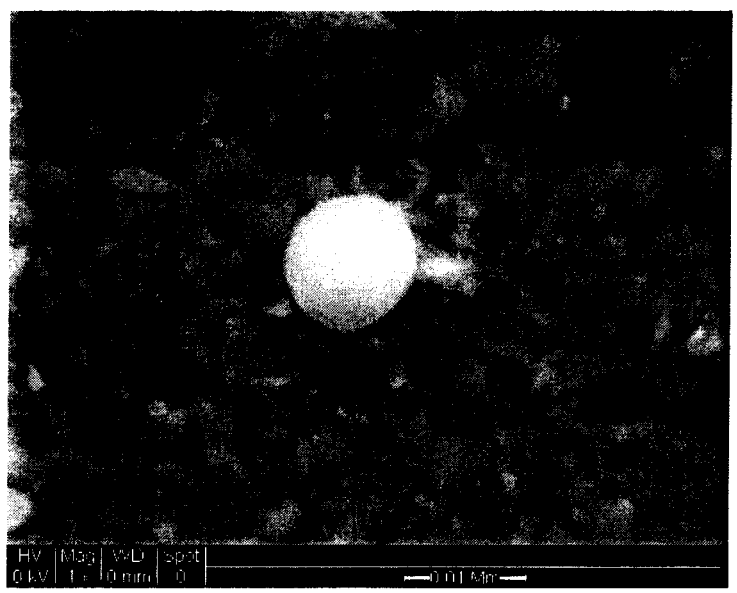
FIG. 37 shows an SEM image of a thirteenth portion of the non-wear surface of the cam follower retaining ring.

| Sampled Area | C (wt %) | O (wt %) | Fe (wt %) | C (At %) | O (At %) | Fe (At %) |
|---|---|---|---|---|---|---|
| FIG. 22 | 22.87 | 15.51 | 57.44 | 46.76 | 26.88 | 25.26 |
| FIG. 23 | 82.18 | 7.22 | 10.60 | 91.43 | 6.03 | 2.54 |
| FIG. 24 | 84.89 | 11.18 | 3.93 | 90.19 | 8.92 | 0.90 |
| FIG. 25 | 83.47 | 13.68 | 2.85 | 88.47 | 10.88 | 0.65 |

FIGS. 26 through 37 show additional SEM images of the cam follower retaining ring surface. In FIGS. 29 through 37, the length scale "Mm" in the figures is actually in micrometers. During the lubrication process, these larger structures are broken down into smaller nanostructures.

Since the sampled areas from FIGS. 22 through 25 showed varying ratios of carbon, oxygen, and iron, subsequent experiments were run to sample different areas of the same structure to determine whether the structures were homogeneous. FIGS. 38A-C, FIGS. 39A-G, and FIGS. 40A-C show the structures with the areas in the black boxes being the sampled areas.

TABLE 4(b)

First Spheroid Elemental Analysis Data

Figure 38A:
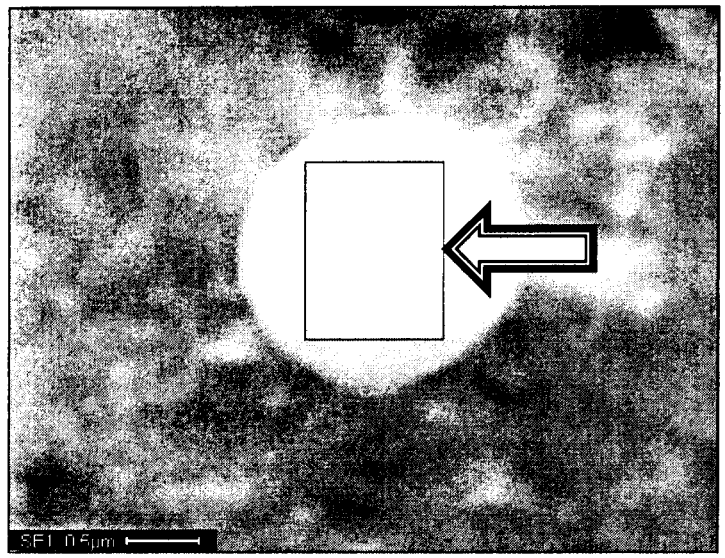
FIG. 38A shows an SEM image of a spheroid on the non-wear surface of the cam follower retaining ring with a first sampled area.
Figure 38B:
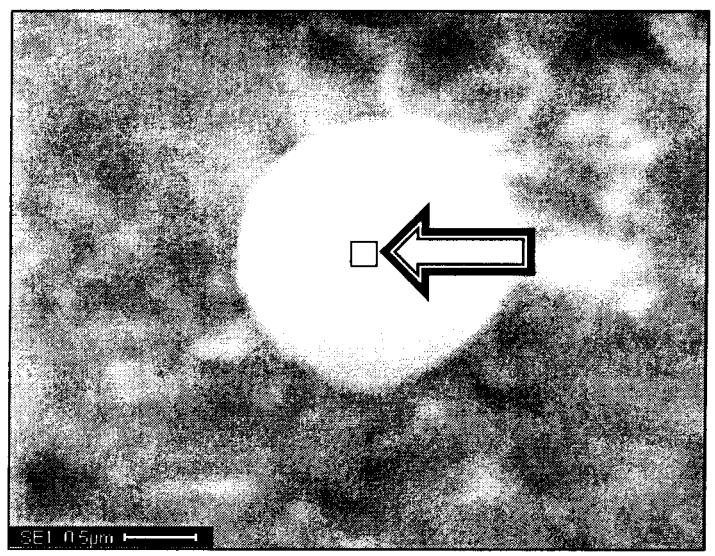
FIG. 38B shows a second sampled area of the SGAN spheroid of FIG. 38A.
Figure 38C:
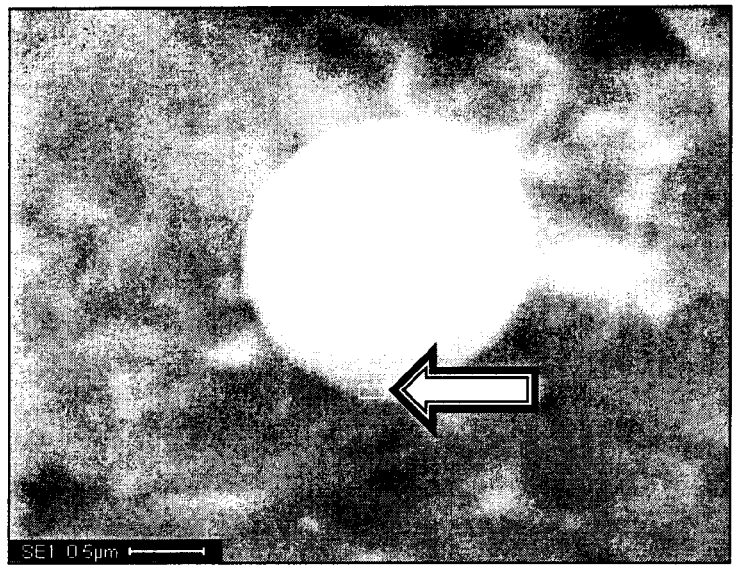
FIG. 38C shows a third sampled area of the SGAN spheroid of FIG. 38A.

| Sampled Area | C (wt %) | O (wt %) | Fe (wt %) | C (At %) | O (At %) | Fe (At %) |
|---|---|---|---|---|---|---|
| FIG. 38A | 73.41 | 11.36 | 15.23 | 86.15 | 10.01 | 3.84 |
| FIG. 38B | 76.91 | 12.12 | 10.97 | 87.03 | 10.30 | 2.67 |
| FIG. 38C | 37.57 | 5.57 | 56.87 | 69.60 | 7.74 | 22.66 |

FIGS. 38A, 38B, and 38C show three different sampled areas from a single large spheroid, that is ~2 microns in diameter. As shown in Table 4(b), only carbon, oxygen, and iron were detected. In FIG. 38A, an average of most of the surface was taken, whereas in FIG. 38B, a smaller portion of the surface was sampled with similar results. Finally, a small protrusion extending from the bottom of the spheroid was sampled as shown in FIG. 38C. This small protrusion has almost ten times the amount of iron as in the other two sampled areas.

TABLE 4(c)

Crystalline Structures Elemental Analysis Data

Figure 39A:
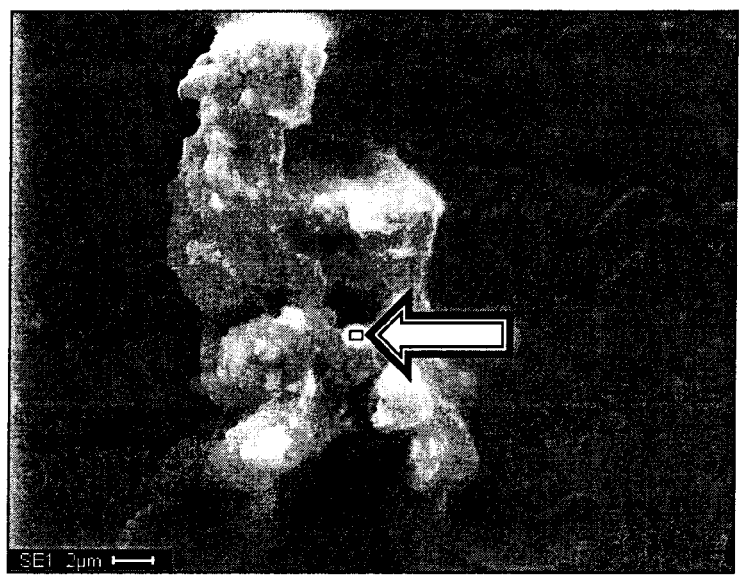
FIG. 39A shows a first sampled area of the crystalline structure of FIG. 35.
Figure 39B:
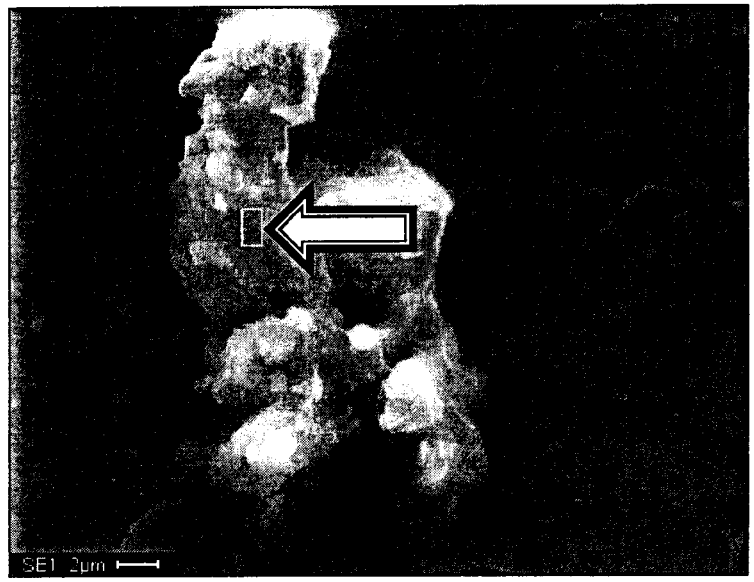
FIG. 39B shows a second sampled area of the crystalline structure of FIG. 35.
Figure 39C:
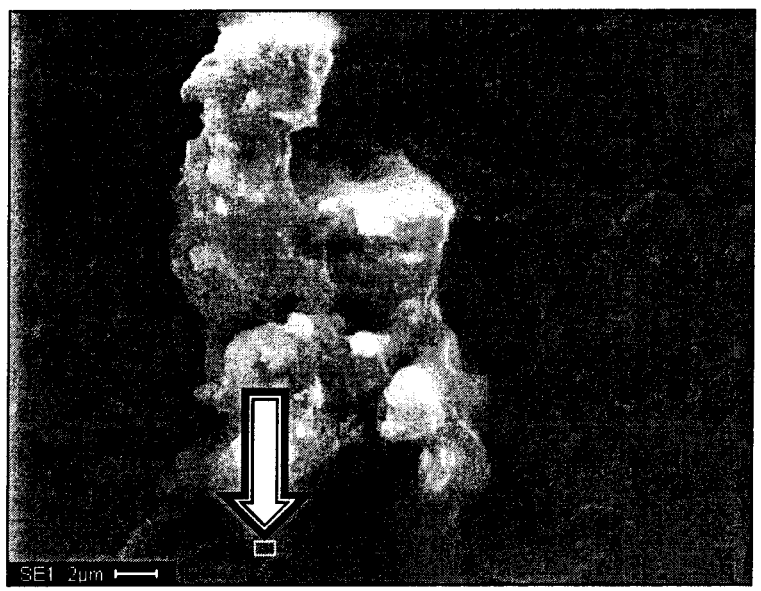
FIG. 39C shows a third sampled area of the crystalline structure of FIG. 35.
Figure 39D:
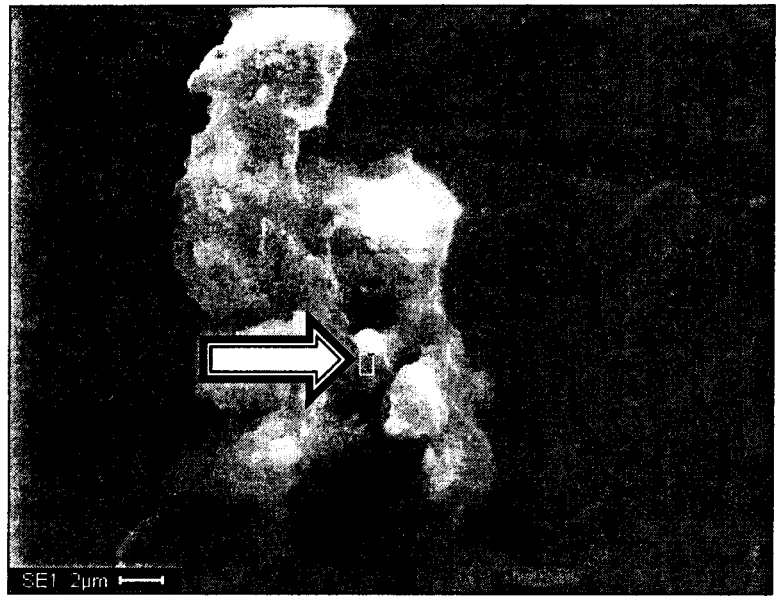
FIG. 39D shows a fourth sampled area of the crystalline structure of FIG. 35.
Figure 39E:
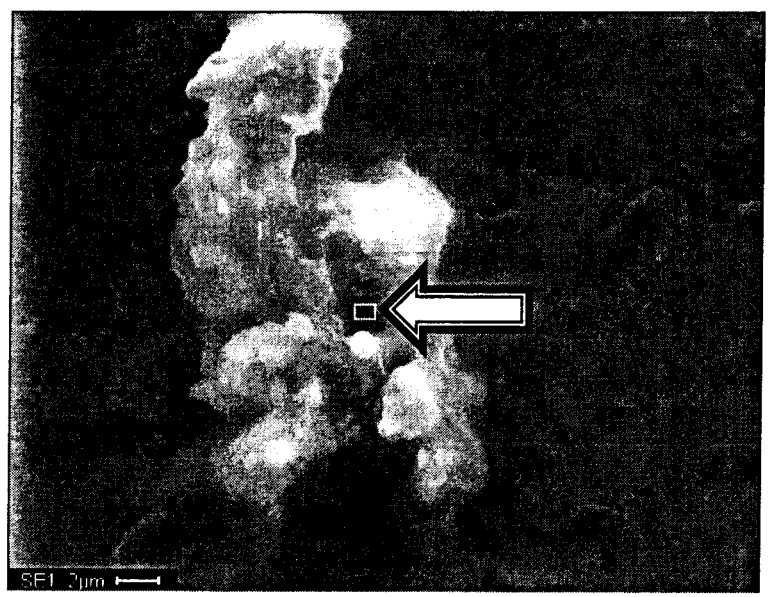
FIG. 39E shows a fifth sampled area of the crystalline structure of FIG. 35.
Figure 39F:
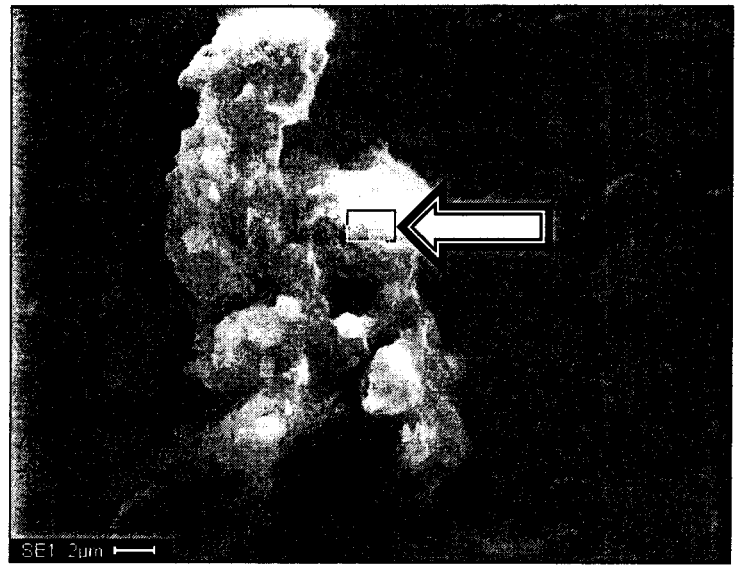
FIG. 39F shows a sixth sampled area of the crystalline structure of FIG. 35.
Figure 39G:
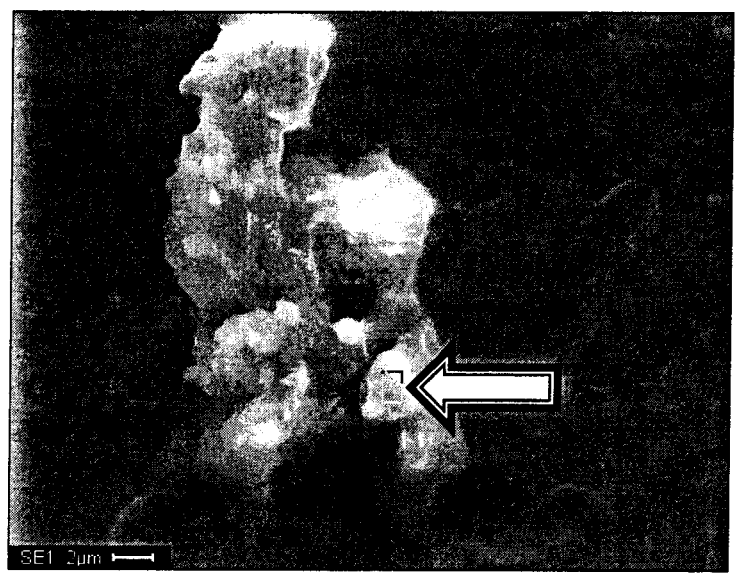
FIG. 39G shows a seventh sampled area of the crystalline structure of FIG. 35.
Figure 41:
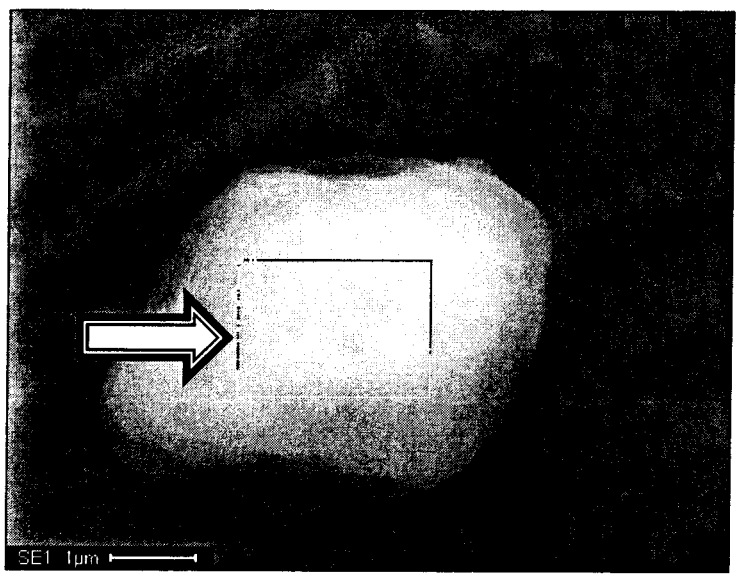
FIG. 41 shows an SEM image of another crystalline structure on the non-wear surface of the cam follower retaining ring with a sampled area.

| Sampled Area | C (wt %) | O (wt %) | Ca (wt %) | Fe (wt %) | C (At %) | O (At %) | Ca (At %) | Fe (At %) |
|---|---|---|---|---|---|---|---|---|
| FIG. 39A | 62.25 | 26.50 | 8.62 | 1.17 | 72.83 | 23.28 | 3.02 | 0.30 |
| FIG. 39B | 68.72 | 20.30 | 6.81 | 1.74 | 78.81 | 17.48 | 2.34 | 0.43 |
| FIG. 39C | 52.37 | 5.33 | 1.91 | 38.83 | 79.56 | 6.08 | 0.87 | 12.69 |
| FIG. 39D | 83.38 | 8.94 | 3.94 | 0.74 | 90.19 | 7.26 | 1.28 | 0.17 |
| FIG. 39E | 81.26 | 5.92 | 7.92 | ND | 90.55 | 4.95 | 2.65 | ND |
| FIG. 39F | 75.62 | 8.54 | 10.89 | 1.75 | 87.17 | 7.39 | 3.76 | 0.43 |
| FIG. 39G | 84.67 | 8.96 | 3.62 | 1.07 | 90.77 | 7.21 | 1.16 | 0.25 |
| FIG. 41 | 85.31 | 12.10 | ND | 2.59 | 89.84 | 9.57 | ND | 0.59 |

FIGS. 39A, 39B, 39C, 39D, 39E, 39F, and 39G show seven different sampled areas of a large, irregular crystalline structure that is more than 13 microns wide. As shown in Table 4(c), carbon, oxygen, calcium, and iron were detected in all of the samples except for FIG. 39E, which had no iron. Additionally, chlorine was detected in each of these samples in an amount to bring the totals to 100%. The ratio of calcium to chlorine ranged from about 1:1 to about 6:1. Within this range, ratios of calcium to chlorine of about 1.5:1, about 2:1, and about 3:1 were also observed. The amount of iron detected was fairly minimal in comparison to the FIG. 38 series, except for the 12.69 At % for the sampled area of FIG. 39C.

TABLE 4(d)

Second Spheroid Elemental Analysis Data

Figure 40A:
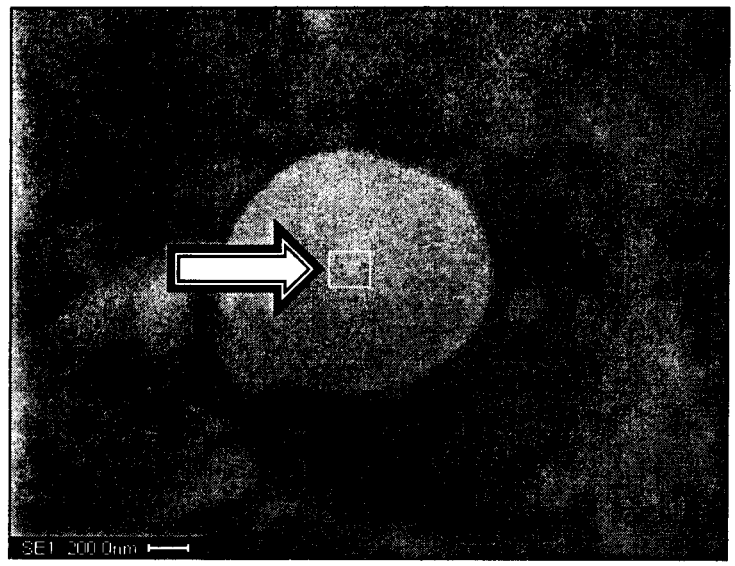
FIG. 40A shows a first sampled area of another spheroid on the non-wear surface of the cam follower retaining ring.
Figure 40B:
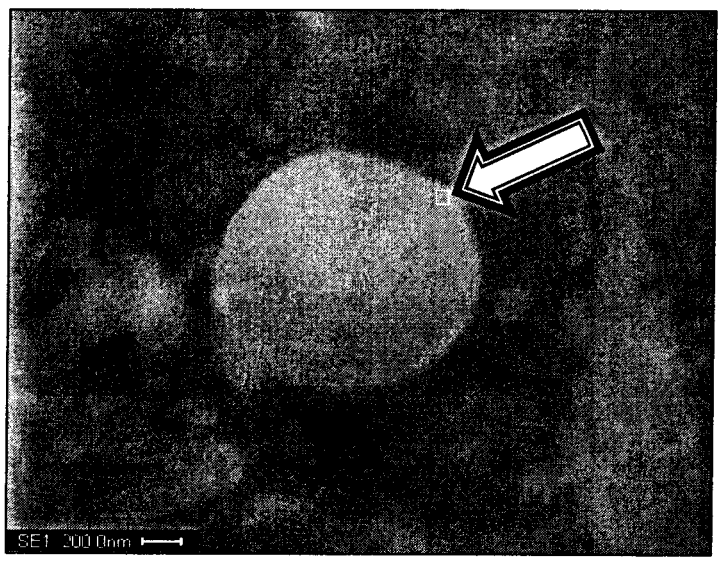
FIG. 40B shows a second sampled area of the SGAN spheroid of FIG. 40A.
Figure 40C:
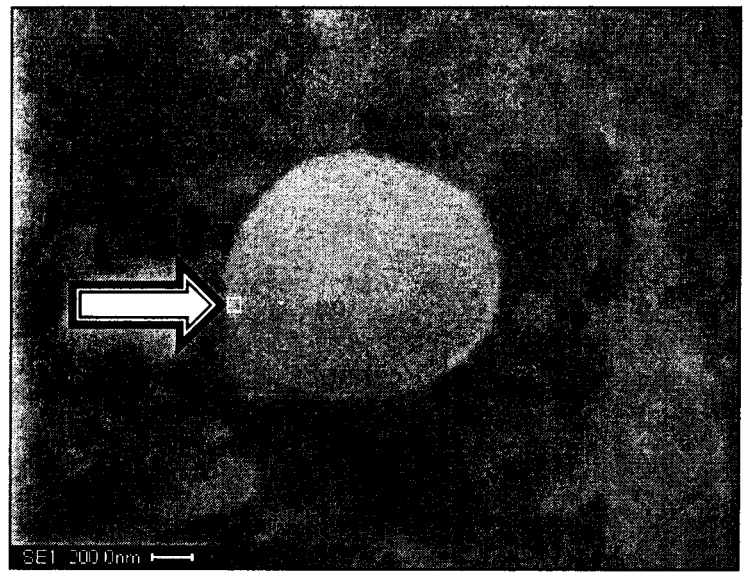
FIG. 40C shows a third sampled area of the SGAN spheroid of FIG. 40A.

| Sampled Area | C (wt %) | O (wt %) | Fe (wt %) | C (At %) | O (At %) | Fe (At %) |
|---|---|---|---|---|---|---|
| FIG. 40A | 69.94 | 9.27 | 20.79 | 85.95 | 8.55 | 5.50 |
| FIG. 40B | 34.41 | 4.47 | 61.12 | 67.59 | 6.59 | 25.82 |
| FIG. 40C | 61.14 | 6.91 | 31.95 | 83.52 | 7.09 | 9.39 |

FIGS. 40A, 40B, and 40C show three different sampled areas from a single smaller spheroid that is ~1.3 microns in diameter. As shown in Table 4(d), only carbon, oxygen, and iron were detected. As shown in FIG. 40A, the spheroid was sampled in the middle with results similar to that of the sampled area of FIG. 38A, although the iron content was higher and the oxygen content was lower. As shown in FIG. 40B, the spheroid was sampled at the upper right edge with an iron content almost five times higher than the area shown in FIG. 40A, similar to what was observed for the area in FIG. 38C. Finally, as shown in FIG. 40C, the spheroid was sampled at the left edge with an iron content almost twice as high as in the area of FIG. 40A but much lower than the area of FIG. 40B.

Finally, FIG. 41 shows a large sampled area of a large, rhombus-shaped crystalline structure that is between 4 and 5 microns wide. As shown in Table 4(c), only carbon, oxygen, and iron were detected. The ratios were similar to those of the low-iron areas of the spheroids, except the iron content was even lower in this case.

Subsequently, hexane was added to a sample of the used lubrication composition. The mixture was centrifuged, and a sediment fraction and a fluid fraction of the centrifuged mixture were tested with time-of-flight (TOF) secondary ion mass spectrometry (SIMS) and transmission electron microscopy (TEM) with an FEI™ CM20 TEM with EDAX® Genesis™ software. Although these tests did not identify any particular structures in the lubricating composition, interestingly, no measurable iron was detected in either the sediment fraction or the fluid fraction of the oil. Only carbon, oxygen, and in some cases, zinc, calcium, or chromium were detected in the sample. From these tests, as evidenced by the lack of iron, it became clear that the features observed by SEM on the surfaces of the cam follower retaining ring are not present in detectable levels in the fluid itself.

Figure 42:
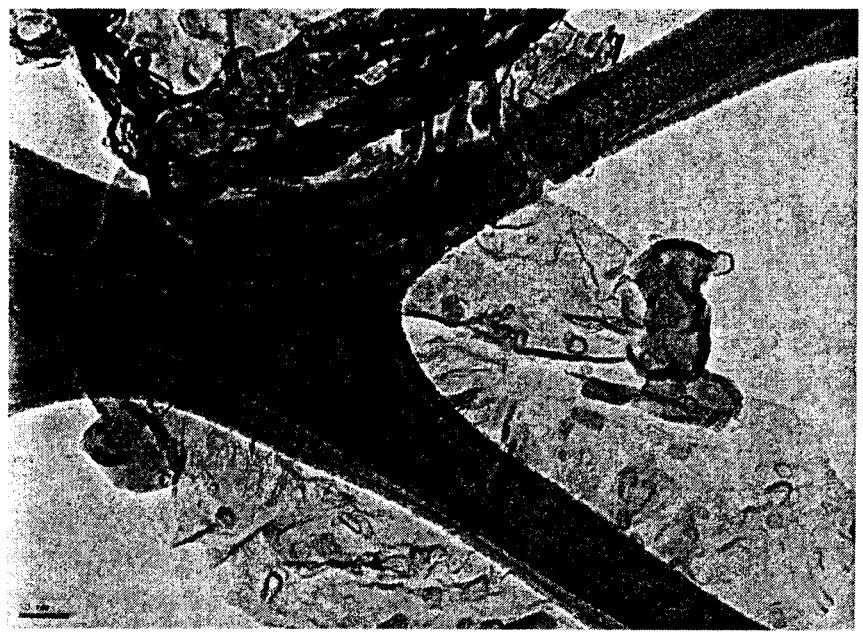
FIG. 42 shows a first TEM image of material from the surface of the cam follower.
Figure 43:
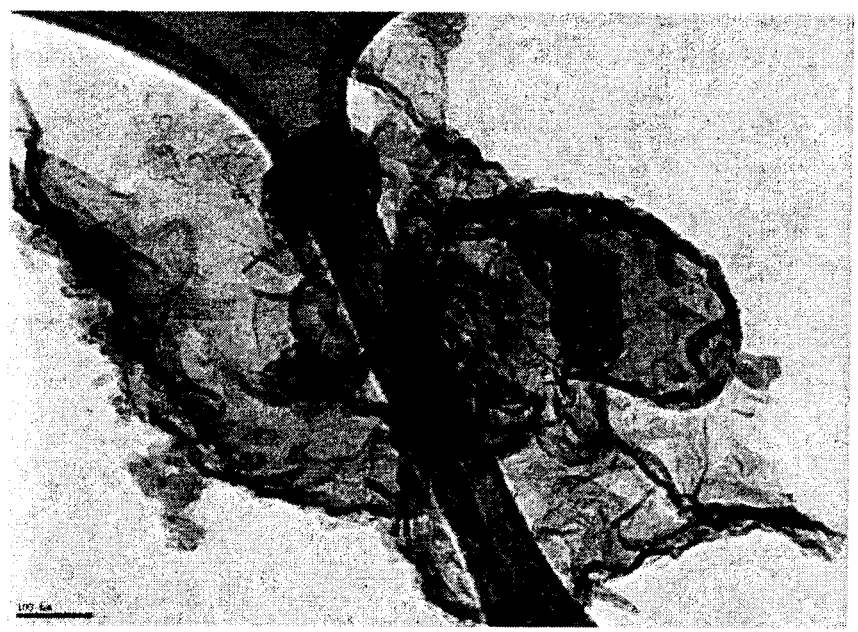
FIG. 43 shows a second TEM image of material from the surface of the cam follower.

A sample of the material on the cam follower surface was obtained for TEM observation by gently rubbing the TEM mesh grid on the surfaces of the cam follower and then viewing the features on the grid with the TEM. Representative images of the observed features are shown in FIGS. 42 through 49B, revealing a number of different morphologies and structures. The images confirm the presence of graphene or graphene oxide sheets, carbon nanotubes, carbon nanospheroids, carbon nano-onions, and other fullerene structures and precursors. The dark areas in the images are believed to represent higher concentrations of iron, based on elemental analysis. Graphene is known to encapsulate iron particles (see, for example, Cao et al., "Synthesis and characterization of graphene encapsulated iron nanoparticles", *Nanoscience*, vol. 12, no. 1, pp. 35-39, 2007). FIG. 42 shows a relatively flat sheet morphology in the lower part of the image and a more crumpled sheet in the upper part of the image. Smaller spheroid structures in the range of ~5 nm to ~50 nm in diameter are also visible on the image. FIG. 43 shows primarily a moderately-crumpled sheet morphology with nanotubular structures near folds of the sheets.

Figure 44:
FIG. 44 shows a third TEM image of material from the surface of the cam follower.
Figure 45:
FIG. 45 shows a fourth TEM image of material from the surface of the cam follower.
Figure 46:
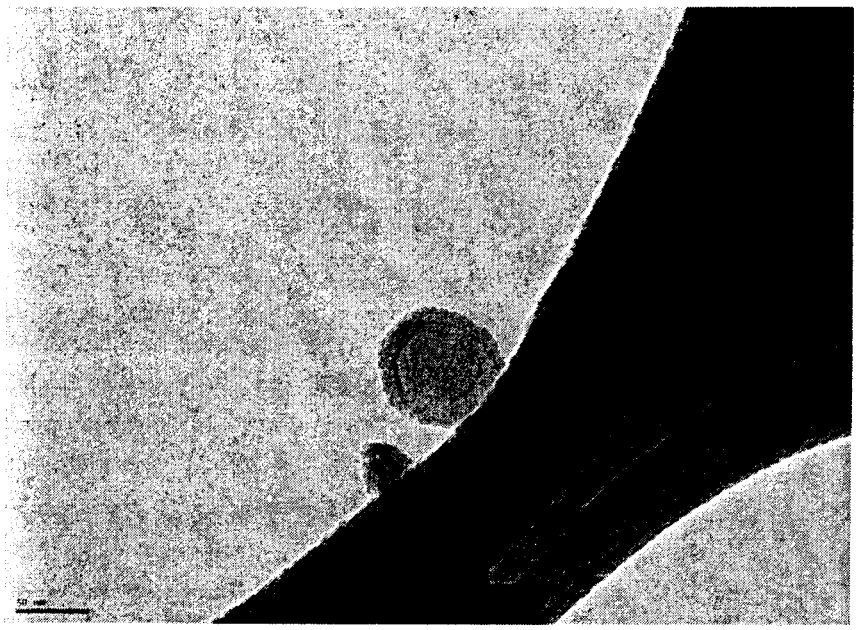
FIG. 46 shows a fifth TEM image of material from the surface of the cam follower.
Figure 47:
FIG. 47 shows a sixth TEM image of material from the surface of the cam follower.
Figure 48:
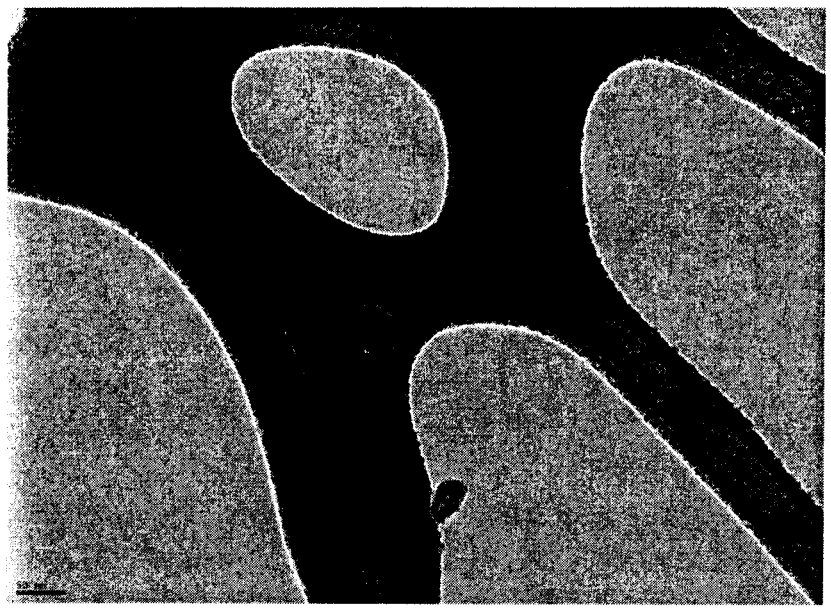
FIG. 48 shows a seventh TEM image of material from the surface of the cam follower.
Figure 49A:
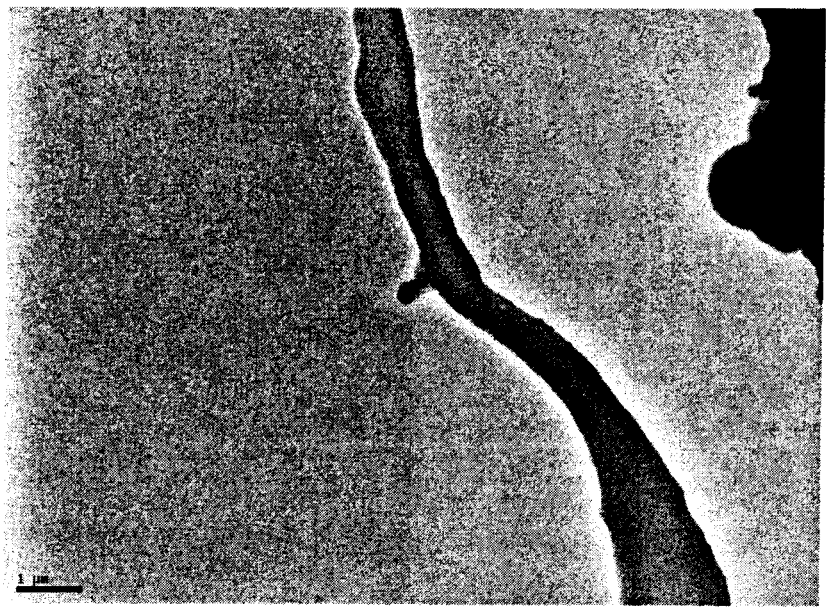
FIG. 49A shows an eighth TEM image of material from the surface of the cam follower.
Figure 49B:
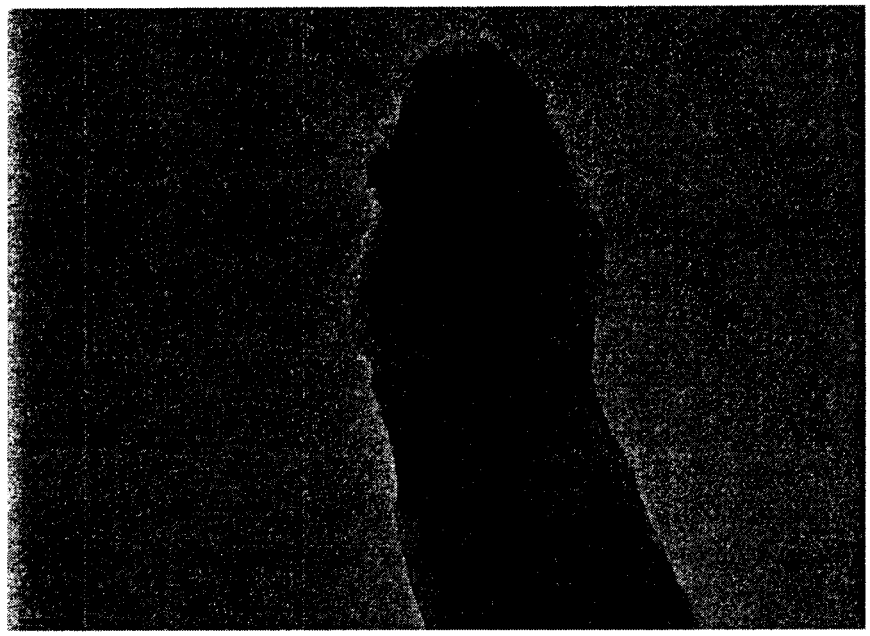
FIG. 49B shows a magnified view of an upper left portion of the image of FIG. 49A.

FIG. 44 shows a higher magnification of an area with similar morphology to FIG. 43. In FIG. 44, spheroid, tubular, and sheet morphologies are visible. FIG. 45 shows some tortuous tubular structures at high magnification. FIG. 46 shows a dark globular mass with an indistinct morphology at high magnification, which may be an aggregation of SGANs based on the dark interior of the structure. FIG. 47 shows a large carbon nanotube structure. FIG. 48 shows two carbon nano-onion structures. Finally, FIGS. 49A and 49B show a crystalline-looking mass with tubular and spheroid morphologies but no apparent sheet morphology.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of synthesizing graphene comprising:
    a) refluxing a reaction mixture comprising at least one solvent and at least one carbonaceous material promoting polycyclic aromatic hydrocarbon formation under conditions that inhibit complete combustion of the carbonaceous material;
    b) thereafter collecting vapors produced by the reflux of the reaction mixture;
    c) directing the vapors to a substrate, whereupon graphene is deposited on the surface of the substrate; and
    d) recovering graphene from the surface of the substrate.

2. The method of claim 1, wherein the at least one carbonaceous material promoting polycyclic aromatic hydrocarbon formation comprises pyranose, a furanose, a cyclic carbomer, a benzenoid, a sugar, a sugar alcohol, a sugar substitute, a sugar derivative, a cyclomethicone, a steroid, a cinnamate, a phenylphopanoid, a benzoate, a carboxylate, a benzopyran, a naturally-occurring or synthetic flavone or isoflavone, a salicylate, an antioxidant, a cyclic antioxidant, 4-vinylphenol, anthocyanidin, or chromenylium, a cyclic amino acid, a cyclohexane derivative, a benzene derivative 1,2-dihydroxybenzene (catechol), 1,3-dihydroxybenzene (resorcinol), 1,4-dihydroxybenzene (hydroquinone), a naphthoate, an acrylate, a phthalate, a succinate, a carpate, a fluorophore, a pharmaceutical, a phosphate, a commercial edible personal/sexual lubricating composition including a sugar or sugar-substitute amphiphile, a commercial ultraviolet ray sunscreen formulation, a commercial skin cream formulation, a commercial hand sanitizer formulation, a commercial human or animal hair care product, a commercial hair dye formulation, a commercial pesticide, a compound that degrades to one or more of the above-mentioned additives during refluxing of the reaction mixture, or combinations thereof.

3. The method of claim 2, wherein the at least one carbonaceous material promoting polycyclic aromatic hydrocarbon formation comprises a compound that promotes the formation of at least one C1 to C5 hydrocarbon radical.

4. The method of claim 2, wherein the solvent comprises mineral oil, water, an alcohol, methanol, synthetic methanol, ethanol, isopropanol or combinations thereof.

5. The method of claim 2, wherein the reaction mixture further comprises at least one supplemental carbon source.

6. The method of claim 5, wherein the supplemental carbon source comprises natural graphite, synthetic graphite, one or more polycyclic aromatic hydrocarbons, graphene, activated carbon, nano-coal, "activated nano-coal", biochar, sugar char, coal phlegm, one or more benzenoids, naphthalene, an alcohol, methanol, synthetic methanol, ethanol, isopropanol, sugar, sucrose, a starch, cellulose, an olefin, an acetate, one or more non-graphitic hydrocarbons, an alkane, an alkene, an alkyne, a ketone, toluene, gasoline, diesel fuel, kerosene, coal, coal tar, coke, or combinations thereof.

7. The method of claim 1, wherein the substrate comprises a hydrophilic substrate.

8. The method of claim 1, wherein the conditions comprise pyrolysis.

9. The method of claim 1, wherein the reaction mixture further comprises a metal-containing compound.

10. The method of claim 9, wherein the metal-containing compound comprises a metal oxide.

11. The method of claim 10, wherein the metal oxide comprises iron oxide, aluminum oxide, copper oxide, nickel oxide, titanium oxide, or lead oxide.

12. The method of claim 1, wherein the reaction mixture further comprises nanodiamonds.

13. The method of claim 1, wherein the substrate comprises an aqueous pool, wherein the graphene comprises aqueous gelled graphene.

14. A method of graphene oxide production comprising:
    a) refluxing a reaction mixture comprising at least one solvent, at least one oxidizer and at least one compound promoting polycyclic aromatic hydrocarbon formation under conditions to prevent the complete combustion of the carbon source into carbon dioxide or carbon monoxide;
    b) thereafter collecting a vapor stream produced by the reflux of the reaction mixture;
    c) thereafter directing the vapor stream to a substrate, whereupon graphene oxide is deposited on the surface of the substrate; and
    d) recovering graphene oxide from the surface of the substrate.

15. The method of claim 14, wherein the conditions comprise pyrolysis.

16. The method of claim 14, wherein the reaction mixture further comprises a metal-containing compound.

17. The method of claim 16, wherein the metal-containing compound comprises a metal oxide.

18. The method of claim 17, wherein the metal oxide comprises iron oxide, aluminum oxide, copper oxide, nickel oxide, titanium oxide, or lead oxide.

19. The method of claim 14, wherein the reaction mixture further comprises nanodiamonds.

20. The method of claim 14, wherein the substrate comprises an aqueous pool, wherein the graphene oxide comprises aqueous gelled graphene oxide.

* * * * *